United States Patent
Cavallo et al.

(10) Patent No.: US 10,588,953 B2
(45) Date of Patent: Mar. 17, 2020

(54) COMPOSITIONS AND METHODS RELATED TO XCT PEPTIDES

(71) Applicant: AGILVAX, INC., Albuquerque, NM (US)

(72) Inventors: Federica Cavallo, Turin (IT); Stefania Lanzardo, Turin (IT); Laura Conti, Turin (IT); John P. O'Rourke, Alburuerque, NM (US); Federica Pericle, Albuquerque, NM (US)

(73) Assignee: AGILVAX, INC., Albuquerque, NM (US)

( * ) Notice: Subject to any disclaimer, the term of this patent is extended or adjusted under 35 U.S.C. 154(b) by 0 days.

(21) Appl. No.: 16/063,040

(22) PCT Filed: Dec. 18, 2016

(86) PCT No.: PCT/US2016/067412
§ 371 (c)(1),
(2) Date: Jun. 15, 2018

(87) PCT Pub. No.: WO2017/106806
PCT Pub. Date: Jun. 22, 2017

(65) Prior Publication Data
US 2018/0360935 A1    Dec. 20, 2018

Related U.S. Application Data

(60) Provisional application No. 62/269,181, filed on Dec. 18, 2015, provisional application No. 62/330,844, filed on May 2, 2016, provisional application No. 62/357,779, filed on Jul. 1, 2016.

(51) Int. Cl.

| | | |
|---|---|---|
| *A61K 39/385* | (2006.01) | |
| *C12N 7/00* | (2006.01) | |
| *A01N 63/00* | (2020.01) | |
| *A61K 39/00* | (2006.01) | |
| *C07K 17/00* | (2006.01) | |
| *A61K 35/76* | (2015.01) | |
| *C12N 15/86* | (2006.01) | |
| *A61P 35/00* | (2006.01) | |
| *A61K 39/12* | (2006.01) | |
| *A61K 38/00* | (2006.01) | |
| *C12N 15/62* | (2006.01) | |

(52) U.S. Cl.
CPC .......... *A61K 39/0011* (2013.01); *A61K 35/76* (2013.01); *A61K 39/12* (2013.01); *A61P 35/00* (2018.01); *C12N 15/86* (2013.01); *A61K 38/00* (2013.01); *A61K 2039/5256* (2013.01); *A61K 2039/5258* (2013.01); *A61K 2039/572* (2013.01); *A61K 2039/585* (2013.01); *A61K 2039/812* (2018.08); *C12N 15/62* (2013.01); *C12N 2795/00023* (2013.01); *C12N 2795/00034* (2013.01); *C12N 2795/00041* (2013.01)

(58) Field of Classification Search
CPC .... A61K 2039/5258; A61K 2039/6075; A61K 39/39; C07K 14/005; C12N 2730/10122
See application file for complete search history.

(56) References Cited

U.S. PATENT DOCUMENTS

| | | | |
|---|---|---|---|
| 6,306,393 B1 | 10/2001 | Goldenberg | |
| 6,329,503 B1 | 12/2001 | Afar et al. | |
| 2003/0224454 A1* | 12/2003 | Ryseck | C07K 14/47 435/7.1 |
| 2008/0292652 A1 | 11/2008 | Bachmann et al. | |
| 2009/0054246 A1 | 2/2009 | Peabody et al. | |
| 2014/0105924 A1* | 4/2014 | Chackerian | A61K 39/12 424/186.1 |

FOREIGN PATENT DOCUMENTS

| | | |
|---|---|---|
| JP | 2011-050355 | 3/2011 |
| WO | WO 2011/116226 | 9/2011 |
| WO | WO 2013/003353 | 1/2013 |

OTHER PUBLICATIONS

Briggs et al., "Paracrine Induction of HIF by Glutamate in Breast Cancer: EgIN1 Senses Cysteine," *Cell*, 2016, 166(1):126-139.
Chen et al., "Disruption of xCT inhibits cancer cell metastasis via the caveolin-1/β-catenin pathway," *Oncogene*, 2009, 28(4):599-609.
Guan et al., "The $x_c-$ cystine/glutamate antiporter as a potential therapeutic target for small-cell lung cancer: use of sulfasalazine." *Cancer Chemother Pharmacol.*, 2009, 64(3):463-472.
Guo et al., "Disruption of xCT inhibits cell growth via the ROS/autophagy pathway in hepatocellular carcinoma," *Cancer Lett.*, 2011, 312(1):55-61.
Gyorffy et al., "An online survival analysis tool to rapidly assess the effect of 22,277 genes on breast cancer prognosis using microarray data of 1,809 patients" *Breast Cancer Res. Treat.*, 2010, 123(3):725-731.
Hasegawa et al., "Functional interactions of the cysteine/glutamate antiporter, CD44v and MUC1-C oncoprotein in triple-negative breast cancer cells," *Oncotarget*, 2016, 7(11):11756-11769.
International Search Report and Written Opinion issued in International Patent Application No. PCT/US2016/067412, dated May 22, 2017.
Ishimoto et al., "CD44 Variant Regulates Redox Status in Cancer Cells by Stabilizing the xCT Subunit of System xc– and thereby Promotes Tumor Growth" *Cancer Cell*, 2011, 19(3):387-400.
Ju et al., "Redox Regulation of Stem-like Cells Though the CD44v-xCT Axis in Colorectal Cancer: Mechanisms and Therapeutic Implications," *Mechanisms and Therapeutic Implications. Theranostics*, 2016, 6(8):1160-1175.

(Continued)

*Primary Examiner* — Barry A Chestnut
(74) *Attorney, Agent, or Firm* — Norton Rose Fulbright US LLP

(57) ABSTRACT

Certain embodiments are directed to composition for inducing an immune response against xCT that is directed to cancer stem cells expressing xCT.

13 Claims, 37 Drawing Sheets
Specification includes a Sequence Listing.

(56) References Cited

OTHER PUBLICATIONS

Lanzardo et al., "Immunotargeting of antigen xCT Attenuates Stem-like Cell Behavior and Metastatic Progression in Breast Cancer," *Cancer Res.*, 2016, 76(1):62-72.

Linares et al., "Oxidative stress as a mechanism underlying sulfasalazine-induced toxicity" *Expert Opin Drug Saf.*, 2011, 10(2):253-263.

Liu et al., "MicroRNA-26b is underexpressed in human breast cancer and induces cell apoptosis by targeting SLC7A11," *FEBS Letters*, 2011, 585(9):1363-1367.

Nagano et al., "Redox regulation in stem-like cancer cells by CD44 variant isoforms" *Oncogene*, 2013, 32(44):5191-5198.

Robe et al., "Early termination of ISRCTN45828668, a phase 1/2 prospective, randomized study of Sulfasalazine for the treatment of progressing malignant gliomas in adults," *BMC Cancer*, 2009, 9:372.

Shitara et al., "Subgroup analyses of the safety and efficacy of ramucirumab in Japanese and Western patients in RAINBOW: a randomized clinical trial in second-line treatment of gastric cancer," *Gastric Cancer*, 2016, 19(3):927-938.

Timmerman et al., "Glutamine Sensitivity Analysis Identifies the xCT Antiporter as a Common Triple Negative Breast Tumor Therapeutic Target," *Cancer Cell*, 2013, 24(4):450-465.

Yoshikawa et al., "xCT Inhibition Depletes CD44v-Expressing Tumor Cells That Are Resistant to EGFR-Targeted Therapy in Head and Neck Squamous Cell Carcinoma" *Cancer Res.*, 2013, 73(6):1855-1866.

Bolli, et al., "A Virus-Like-Particle Immunotherapy Targeting Epitope-Specific Anti-xCT Expressed on Cancer Stem Cell Inhibits the Progression of Metastatic Cancer in Vivo," *Oncoimmunology*, 7(3); e1408746, 2017.

Galaway & Stockley, "MS2 VirusLike Particles: A Robust, Semisynthetic Targeted Drug Delivery Platform," *Molecular Pharmaceutics*, 10(1); 59-68, 2013.

Huang, et al., "Cystine-Glutamate Transporter SLC7A11 in Cancer Chemosensitivity and Chemoresistance," *Cancer Research*, 65(16); 7446-7454, 2005.

Li, et al., "Messenger RNA Vaccine Based on Recombinant MS2 Virus-Like Particles Against Prostate Cancer," *International Journal of Cancer*, 134(7); 1683-1694, 2014.

Ruiu, et al., "Fighting Breast Cancer Stem Cells Through the Immune-Targeting of the xCT Cystine-Glutamine Antiporter," *Cancer Immunology, Immunotherapy*, 68; 131-141, 2019.

Supplementary European Search Report Issued in Corresponding EP Application No. 16876883.6, dated Jul. 19, 2019.

Wang & Yang, "Suppression of the xCT-CD44v Antiporter System Sensitizes Triple-Negative Breast Cancer Cells to Doxorubicin," *Breast Cancer Research and Treatment*, 147(1); 203-210, 2014.

\* cited by examiner

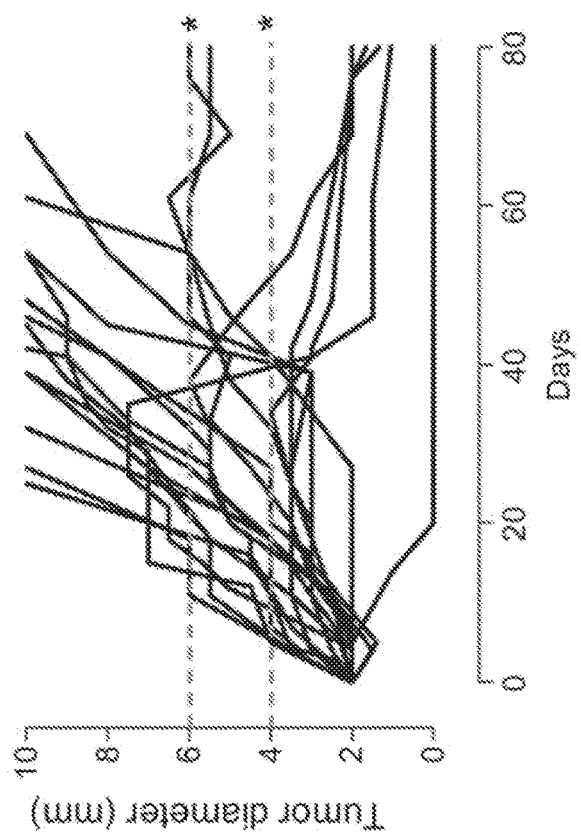
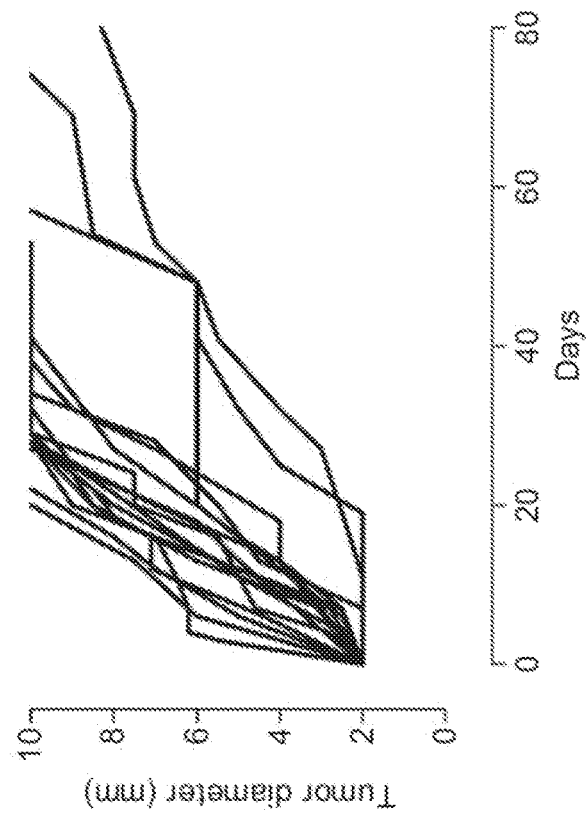
FIG. 6A
FIG. 6B

COMPOSITIONS AND METHODS RELATED TO XCT PEPTIDES

CROSS-REFERENCE TO RELATED APPLICATIONS

This application is a national phase under 35 U.S.C. § 371 of International Application No. PCT/US2016/067412, filed Dec. 18, 2016, which claims priority to and the benefit of U.S. Provisional Applications No. 62/269,181 filed Dec. 18, 2015; No. 62/330,844 filed May 2, 2016; and No. 62/357,779 filed Jul. 1, 2016. The contents of each referenced application are incorporated into the present application by reference.

BACKGROUND

Triple negative breast cancer (TNBC) is an aggressive form of breast cancer that lacks the estrogen, progesterone and HER2 receptors, and accounts for 15-20% of all breast cancers in the US. TNBC has higher rates of relapse and poorer outcomes than other forms of breast cancer and owing to the lack of targetable surface receptors, TNBC are resistant to hormonal and HER2-targeted therapies. The particularly aggressive features of TNBC may be due to the enrichment of cancer stem cells (CSC) that have the unique biological properties necessary for maintenance and spreading of the tumor and through asymmetric division, can differentiate into cancer cells that compose the tumor bulk (Magee et al., *Cancer Cell* 2012, 21(3):283-96). Due to their resistance to traditional radio- and chemo-therapies (Nagano et al., *Oncogene* 2013, 32(44):5191-8), CSC represent a reservoir for the relapse, metastatic evolution, and progression of the disease after treatment. Therefore, successful eradication of CSC represents a major barrier towards effective cancer treatments.

The ability of CSC to resist common cytotoxic therapies relies on different mechanisms, including improved detoxification ability. The cystine-glutamate antiporter protein xCT (SLC7A11) regulates cysteine intake, conversion to cysteine and subsequent glutathione synthesis, protecting cells against oxidative and chemical insults via the $p38^{MAPK}$ pathway (Chen et al., *Oncogene* 2009, 28(4):599-609; Guo et al., *Cancer Lett.* 2011, 312(1):55-61). xCT expression is highly restricted to a few normal cell types (neurons and a subset of macrophages) but elevated levels of xCT protein are observed in a high percentage of invasive mammary ductal tumors including TNBC (Lanzardo et al. *Cancer Res.* 2016, 76(1):62-72). High levels of xCT mRNA and protein correlate with significant reduction in distal metastases-free and overall survival (Briggs et al., *Cell* 2016, 166(1):126-39; Gyorffy et al., *Breast Cancer Res Treat.* 2010, 123(3):725-31). xCT expression is upregulated in breast CSC (BCSC) and other solid tumor stem cells, and several studies show that xCT physically interacts with the well-known stem cell marker, CD44 (Nagano et al., *Oncogene* 2013, 32(44):5191-8; Hasegawa et al., *Oncotarget* 2016, 7(11):11756-69; Ishimoto et al., *Cancer Cell* 2011, 19(3):387-400; Ju et al., *Mechanisms and Therapeutic Implications. Theranostics* 2016, 6(8):1160-75; Yoshikawa et al., *Cancer Res.* 2013, 73(6):1855-66). The frequency of xCT expression on a variety of CSC suggests that therapies targeting xCT may be effective for a variety of tumors with high stem cell frequencies including gastrointestinal and pancreatic cancers.

A direct role for xCT in breast cancer metastasis was shown by inhibiting xCT function with the small molecule sulfasalazine (SASP), which resulted in significant decreases in metastatic foci in animal models and reductions in the frequency of CSC (Nagano et al., *Oncogene* 2013, 32(44):5191-8; Chen et al., *Oncogene* 2009, 28(4):599-609; Guan et al., *Cancer Chemother Pharmacol.* 2009, 64(3):463-72; Timmerman et al., *Cancer Cell* 2013, 24(4):450-65). However, SASP is labile and insoluble under physiological conditions, has vast off-target effects, low bioavailability and requires high doses to inhibit xCT in vivo (Timmerman et al., *Cancer Cell* 2013, 24(4):450-65; Shitara et al., *Gastric Cancer* 2016; Linares et al., *Expert Opin Drug Saf* 2011, 10(2):253-63; Robe et al., *BMC Cancer* 2009, 9:372). Therefore, new therapeutic modalities specifically targeting xCT need to be developed for clinical use.

SUMMARY

Certain embodiments are directed to peptide and nucleic acid immunogens comprising or encoding immunogenic peptides of xCT, the functional subunit of the cysteine/glutamate antiporter system xc-, as well as antibodies that target cells expressing xCT.

Certain embodiments are directed to composition for inducing an immune response against xCT and to cancer stem cells (CSC), or providing a therapeutic antibody that binds an xCT peptide. In certain aspects VLPs or plasmids are produced that display or encode one or more xCT peptide. In certain aspects the full length xCT protein has the amino acid sequence MVRKPVVSTISKGGYLQGNVNGRLPSLGNKEPPGQEKVQLKRKVTLLRGVSIIIGTII GAGIFISPKGVLQNTGSVGMSLTIWTVCGVLSLF-GALSYAELGTTIKKSGGHYTYILE VFGPL-PAFVRVWVELLIIRPAATAVISLAFGRYILEPFFIQ-CEIPELAIKLITAVGITVVM VLNSMSVSWSARIQIFLTFCKLTAILIIIVPGVMQLIK-GQTQNFKDAFSGRDSSITRLPL AFYYGMYAYAGW-FYLNFVTEEVENPEKTIPLAICISMAIVTIGYVLT-NVAYFTTINAE ELLLSNAVAVTF SERLLGNFSLAVPIFVALSCFGSMNGGVFAVSRLFY-VASREGHLPE ILSMIHVRKHTPLPAVIVLHPLTMIM-LFSGDLDSLLNFLSFARWLFIGLAVAGLIYLRY KCP-DMHRPFKVPLFIPALFSFTCLFMVALSLYSDPFSTGIG-FVITLTGVPAYYLFIIWDK KPRWFRIMSEKITRTLQI-ILEVVPEEDKL (SEQ ID NO:1). xCT peptides can be any or nucleic acids encode any 5, 6, 7, 8, 9, 10, 11, 12, 13, 14, 15, 16, 17, 18, 19, 20, 21, 22, 23, 24, 25, 26, 27, 28, 29, or 30 consecutive amino acid segment SEQ ID NO:1. In other embodiments the xCT protein can have a variant amino acid in that the xCT protein can be 85, 90, 95, or 98% identical to the amino acid sequence provided in SEQ ID NO:1. In other aspects the xCT protein can comprise 20 30, 40, 50, 60, 70, 80, 90, 100, 150, 200, 250, 300, 350, 400, 450, 500, or 501 consecutive amino acids of SEQ ID NO:1, including all values and ranges there between, or a peptide of the same length have 85. 90. 95. 98. 99% identity to SEQ ID NO:1.

In certain aspect an immunogenic peptide can be displayed or encoded by a virus like particle (VLP) using RNA bacteriophage coat proteins displaying heterologous peptides. VLPs expression plasmids are constructed to display the extracellular domains (ECD) or other peptides of human xCT. In certain aspects ECDs or other xCT peptides can be displayed on the surface of VLPs using genetic insertion and/or chemical conjugation methods. In certain aspects the amino acid sequences of the newly verified human xCT ECDs are ECD 1 corresponding to amino acids 65-74 of SEQ ID NO:1; ECD 2 corresponding to amino acids 135-158 of SEQ ID NO:1; ECD 3 corresponding to amino acids 211-234 of SEQ ID NO:1; ECD 4 corresponding to amino acids 287-317 of SEQ ID NO:1; and ECD 6 corresponding to amino acids 444-449 of SEQ ID NO:1.

In certain aspects the VLP is a MS2, Qβ, PP7 or AP205 VLP. The different xCT ECDs can be codon optimized for expression in *E. coli* and ligated into the amino terminus (N-terminus), carboxy terminus (C-terminus), or the AB loop of a RNA bacteriophage single-chain dimer coat protein. In particular aspects the xCT ECDs or other xCT peptide can be cloned into the N-terminus of the single-chain dimer coat protein. Peptides displayed on the N-terminus are linear. As one example, the MS2 RNA bacteriophage can display 90 copies of peptide per VLP.

In another aspect the VLP is an AP205 VLP. The different xCT ECDs are codon optimized for expression in *E. coli* and ligated into the N-terminus, C-terminus, or AB loop of the AP205 single-chain dimer coat protein. In a particular aspect the peptide can be ligated into the N-terminal and C-terminal of the AP205 coat protein monomer, allowing for a linear peptide display. AP205 can display 90 copies of peptide per VLP in the loop, single-chain dimer format whereas 180 copies of xCT peptide are displayed using the termini attachment point in a monomer coat protein.

In still another aspect the VLP is a Q-beta VLP. In order to display peptides at higher valency than the 90 copies (MS2 and AP205 single-chain dimer) or 180 copies per VLP (AP205 coat protein monomer), xCT peptides can be directly conjugated to the surface of the Q-beta (Q(3) bacteriophage VLP. The xCT peptides can be synthesized with a cysteine modification on the C-terminus of the peptide. The peptides can be covalently linked to surface exposed lysine on Q-beta VLPs using SMPH chemistry, for example. This technique displays ~270-360 peptides per VLP.

In certain aspects the VLP is a Woodchuck Hepadnavirus Core-based VLP. The woodchuck hepadnavirus core-based virus-like particle (WHcAg-VLP) is used to display the xCT peptide. The WHcAG-VLP can display 270 copies of the xCT peptide per VLP in a loop conformation at one of three different display points. Codon optimized sequences of the various xCT peptides as described herein are generically inserted into the Woodchuck Hepadnavirus Core protein. In certain aspects the VLPs will be produced in *E. coli*.

Certain embodiments are directed to therapeutic monoclonal antibodies. Monoclonal antibodies (MABs) against xCT peptides including, but not limited to peptides of ECD 1, 2, 3, 4, and 6, or various combinations thereof, are produced using two different methods—(i) DNA-based vaccination or (ii) VLP-based vaccination.

The present invention further includes vaccines useful for inducing an immune response against xCT peptides or inducing an immune response to a cell expressing xCT. In certain aspects mABs are produced using DNA-based vaccination. A pVAX plasmid encoding the full-length human xCT protein or peptides thereof can be used for immunization and monoclonal antibody production. Antibodies are screened against the various xCT peptides using ELISA. Further confirmation of MABs binding to xCT peptides or proteins is performed by FACS analysis on cancer cells or on recombinant cells overexpressing xCT protein. The therapeutic effect of the various MABs can be tested in preclinical models.

Anti-xCT vaccination can induce antibodies that inhibit CSC. BALB/c mice were vaccinated with either pVAX1-xCT or pVAX1 to evaluate whether xCT is a potential target for cancer immunotherapy. No T-cell response was observed against the H-2Kd dominant mouse xCT peptide. Tumor-sphere-derived cells were stained with the sera of vaccinated mice to evaluate their humoral response, and specific antibody binding was analyzed by FACS. pVAX1-xCT vaccination induced the production of CSC-binding antibodies, which were not detectable in empty pVAX1-vaccinated mouse sera. These results were confirmed by the ability of purified IgG, from pVAX1-xCT-vaccinated mouse sera, to stain tumorspheres. These antibodies are specific for xCT, as no binding was observed in NIH/3T3 cells negative for xCT expression. pVAX1-xCT-vaccinated mice displayed reduced sphere-generation ability, a lower percentage of stem cell marker positive cells, but increased ROS content as compared with control IgG. These results suggest that anti-xCT vaccination induces antibodies targeting xCT, thus affecting self-renewal and ROS production in CSC.

MABs can be produced using VLP-based vaccination. VLPs displaying the various xCT peptides are used to produce MABs. Screening for xCT binding and therapeutic functionality is performed as described for DNA-based MAB production.

In certain aspects the peptides are defined as SPKGVLQNTG (SEQ ID NO:2), RPAATAVISLAFGRYILEPFFIQC (SEQ ID NO:3), MQLIKGQTQNFKDAFSGRDSSITR (SEQ ID NO:4), AYFTTINAEELLLSNAVAVTFSERLLGNFSL (SEQ ID NO:5), YSDPFS (SEQ ID NO:6), SPKGVLQNTGSVGMSLTIWT (SEQ ID NO:7), ILEPFFIQCEIPEL (SEQ ID NO:8), KGQTQNFKDAFSGRDSSITRLP (SEQ ID NO:9), YFTTINAEELLLSNAVAVTFSERLLG (SEQ ID NO:10), GDLDSLLN (SEQ ID NO:11), and LYSDPFST (SEQ ID NO:12. Other embodiments are directed to peptide having 3, 4, 5, 6, 7, 8, 9, 10 or more consecutive amino acids of SEQ ID NO:2, 3, 4, 5, 6, 7, 8, 9, 10, 11, or 12.

Certain embodiments are directed to an RNA-bacteriophage virus-like particle (VLP) having dimeric coat protein comprising an xCT peptide having an amino acid sequence of SEQ ID NO:2, 3, 4, 5, 6, 7, 8, 9, 10, 11, and/or 12.

A further embodiment is directed to an immunogenic composition comprising an VLP as described herein. In certain aspects the immunogenic composition comprises 1, 2, 3, 4, or more VLP displaying an xCT peptide. In certain aspect a one VLP displays 2 or more xCT peptides (i.e., a hybrid xCT RNA bacteriophage VLP). In certain aspects the xCT peptide is or comprises one or more of SEQ ID NO:2, 3, 4, 5, 6, 7, 8, 9, 10, 11, or 12.

A further embodiment is directed to an immunogenic composition comprising a nucleic acid encoding an xCT immunogen or peptide, the immunogen comprises 1, 2, 3, 4, or more xCT peptides. In certain aspects the xCT peptide is or comprises one or more of SEQ ID NO:2, 3, 4, 5, 6, 7, 8, 9, 10, 11, or 12. In certain aspect a nucleic acid encodes 2 or more xCT peptides. In certain aspects the peptide can be concatameric peptide contain multiple copies of one or more peptide sequence.

The xCT encoding nucleic acid may be administered alone, or together with peptide vaccines or an adjuvant that increases the frequency, strength, or duration of xCT immune responses.

The invention also provides a method for treating cancer or breast cancer in a patient in need of such treatment comprising administering an effective amount of xCT encoding nucleic acid in a pharmaceutically effective vehicle. In certain aspects the cancer is characterized by expression of xCT protein, or a cell that can specifically bind a monoclonal antibody that specifically binds a xCT peptide or protein as described herein.

The immunogenic or therapeutic compositions are administered in a manner compatible with the dosage formulation, and in such amount as will be prophylactically and/or therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by one or more subsequent administrations or boosters. The compositions may be given in a single dose schedule or preferably in a multiple-dose schedule. A multiple-dose schedule is one in which a primary course of administration/vaccination may be with 1-10 separate doses, followed by other doses given at subsequent time intervals required to maintain and/or reinforce the immune response, for example, at 1-4 months for a second dose and if needed, a subsequent dose(s) after several months.

The xCT VLP may be administered together with an adjuvant that increases the frequency, strength, and/or duration of xCT VLP induced immune responses. The adjuvant may include administering xCT VLPs together with at least one cytokine that can upregulate antigen induced immune responses; admixing the xCT VLP together with a TLR ligand that can upregulate antigen induced immune responses such as TLR-7, TLR-8 or TLR-9 or other ligands alone or in combination; combining the xCT VLP with at least one cytokine and with TLR ligands; and admixing with adjuvants such as montainide. The cytokine may be IL-2, GM-CSF, or a combination thereof.

The invention also provides a method for treating cancer or breast cancer in a patient in need of such treatment comprising administering an effective amount of xCT VLP in a pharmaceutically effective vehicle, which may additionally comprises an adjuvant effective to increase the frequency, strength, or duration of xCT VLP induced immune response.

Administration can be performed, for example, intravenously, orally, nasally, via implant, transmucosally, transdermally, intramuscularly, and subcutaneously. The following delivery systems, which employ a number of routinely used pharmaceutical carriers, are only representative of the many embodiments envisioned for administering the instant compositions. The manner of application may vary. Any of the conventional methods for administration of a polypeptide therapy or VLP immunogen are applicable. These are believed to include parenterally by injection and the like. The dosage of the composition will depend on the route of administration and will vary according to the size and health of the subject.

Certain embodiments are directed to methods of inducing an immune response in a subject comprising administering an xCT VLP as described herein. In certain aspects the composition is administered to a mammal, such as a human. In a further aspect the human has or is suspected of having cancer. In a further aspect the cancer comprises an xCT expressing or overexpressing cancer cell, such as a cancer stem cell.

In certain embodiments the xCT VLP is used in conjunction with other anti-cancer therapies.

The term "single-chain dimer" refers to a normally dimeric protein whose two subunits have been genetically fused into a single polypeptide chain. These proteins are a dimer of the same polypeptide chains. Single-chain coat protein dimers were produced using recombinant DNA methods by duplicating the DNA coding sequence of the coat proteins and then fusing them to one another in tail to head fashion. The result is a single polypeptide chain in which the coat protein amino acid appears twice, with the C-terminus of the upstream or first copy covalently fused to the N-terminus of the downstream or second copy. Normally (wild-type) the two subunits are associated only through noncovalent interactions between the two chains. In the single-chain dimer these noncovalent interactions are maintained, but the two subunits have additionally been covalently tethered to one another. This greatly stabilizes the folded structure of the protein and confers to it its high tolerance of peptide insertions.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

The terms "inhibiting," "reducing," or "prevention," or any variation of these terms, when used in the claims and/or the specification includes any measurable decrease or complete inhibition to achieve a desired result.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 6A-6J. Anti-xCT vaccination delays CSC-induced tumor growth in vivo. BALB/c mice were s.c. challenged with tumorspheres derived from either TUBO (A-D) or 4T1 (E-H) cells and electroporated with pVAX1 (A, C, E, and G) or pVAX1-xCT (B, D, F, and H) plasmids when their tumor reached 2 (A, B, E, and F) or 4 mm (C, D, G, and H) mean diameter. Each black line depicts the growth of a single tumor. Data were cumulated from three independent and concordant experiments. Statistically significant differences in mean time required for pVAX1-xCT group and pVAX1 group tumors to reach 4, 6, 8, or 10 mm mean diameter are indicated by dashed gray lines. I and J, analysis of the percentage of $Aldefluor^+$ cells in tumors explanted from vaccinated mice challenged s.c. with TUBO-derived tumorspheres (I) and the number of tumorspheres generated in vitro by cells from the same tumors (J).*, $P<0.05$; **, $P<0.01$, Student t test.

DESCRIPTION

Figure 1A:
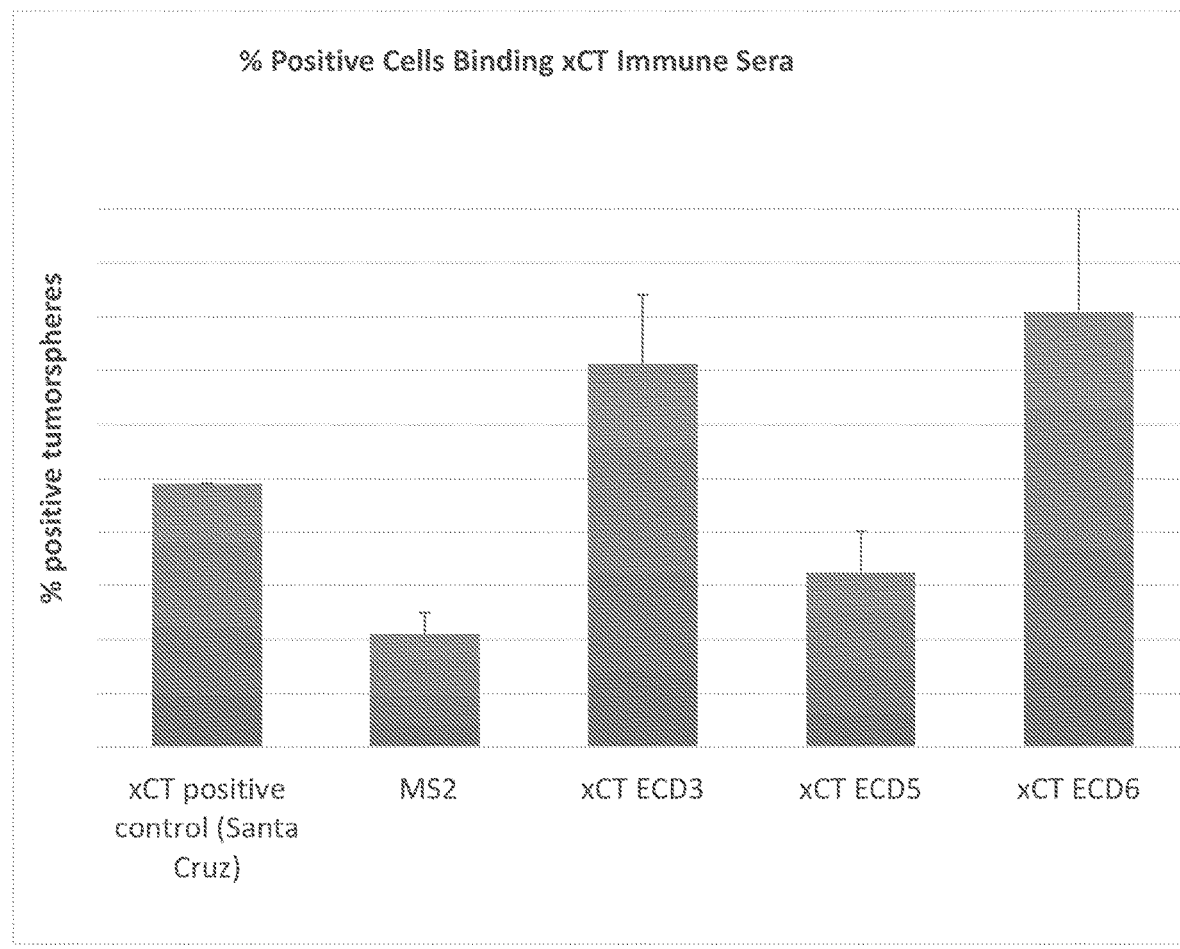
FIG. 1. xCT VLPs elicit antibodies that bind to tumorspheres. Immune sera (1:50) from xCT or control (MS2) VLP immunized mice were incubated with HCC-1806 derived tumorspheres. A FITC conjugated anti mouse IgG was used to detect sera antibodies bound to the cells. (A) FACS analysis of the percentage of tumorsphere cells that bound to the immune sera. As a positive control for xCT binding, we used a commercially available xCT polyclonal antibody. (B) Immunofluorescence analysis showing antibody binding to a tumorsphere from an xCT ECD 6 immunized mouse. Cell nuclei are stained with DAPI.

Certain cancer cells express abnormally high levels of the plasma cell membrane components of the system $x_c^-$ heterodimeric amino acid transporter specific for cystine/glutamate exchange. System $x_c^-$ imports L-cystine into the intracellular compartment of a cell, which requires L-cystine for the synthesis of glutathione (L-γ-glutamyl-L-cysteinyl-glycine, referred to herein as "GSH"), an antioxidant that is important for cell survival under hypoxic conditions, such as those that exist in a tumor environment. The structure of System $x_c^-$ imports is composed of SLC7A11, a catalytic subunit that gives the transporter its specificity for cystine, and SLC3A2, a regulatory subunit. SLC7A11 and SLC3A2 are also known in the field as xCT and 4F2hc/CD98, respectively.

Because tumor cells, and other abnormally rapidly dividing or differentiating cells require greater amounts of GSH to handle higher levels of oxidative stress, such cells more highly express system $x_c^-$ components for the importation of cystine than do normal cells under normal conditions. As such, the invention takes advantage of the increased expression of system $x_c^-$ components by hyperproliferative cells by providing a vaccine xCT peptide, that induces an immune response that targets the xCT component of target cells (e.g., cancer stem cells (CSC). VLP expression plasmids encoding a single chain dimer coat protein displaying peptides of the xCT protein and in particular extracellular domains (ECD) of human xCT were constructed. Amino acid sequences were codon optimized for expression in *E. coli* and were inserted into the AB loop of MS2. These xCT displaying VLPs were produced and included in an immunogenic composition.

I. IMMUNOGENIC COMPOSITIONS

Certain embodiments are directed to immunogenic compositions and methods. Lymphocytes, in particular "B-cells" and "T-cells" are two of the major cell types involved in the immune response of humans and other animals. While B-cells are involved in the humoral aspects of the immune response and are responsible for antibody production, T-cells are involved in the cell-mediated aspects of the immune response. However, these two lymphocyte classes work together via a complicated network of recognition factors, cytokines and other elements of the immune response.

Upon activation, T-cells can kill infected cells, while helper T-cells can activate other cells, such as B-cells and macrophages. Naïve T-cells are activated upon exposure to a specific antigen that is presented on the surface of an antigen-presenting cell (APC) in conjunction with a component of the major histocompatibility complex (MHC). The two major T-cell classes are often described based on their cell surface receptors. One class of T cell is often referred to as "CD8" ("CD8+") cells, and a second class of T cell is often referred to as "CD4" ("CD4+") cells. Despite their different functions, CD4+ and CD8+ cells do not work independently of each other. Indeed, it is known that CD8+ cells are often dependent upon CD4+ cells in mounting a response to an immunogen. However, despite recent advances in the understanding of the immune response, methods are still needed for the reliable identification of CD8+ cell epitopes that are effective, as well as means to differentiate effective epitopes from ineffective ones.

As used herein, the terms "T lymphocyte" and "T-cell," encompass any cell within the T lymphocyte lineage from T-cell precursors (including Thy1 positive cells which do not have rearranged T-cell receptor [TCR] genes) to mature T-cells (i.e., single positive for either CD4+ or CD8+, surface TCR positive cells).

As used herein, the terms "B lymphocyte" and "B-cell" encompasses any cell within the B-cell lineage from B-cell precursors, such as pre-B-cells (B220+cells which have begun to rearrange Ig heavy chain genes), to mature B-cells and plasma cells.

As used herein, "CD4+ T-cell" and "CD4 T-cell" refer to T-cells expressing CD4 on their surface, while "CD8+ T-cell" and "CD8 T-cell" refer to T-cells expressing CD8 on their surface.

As used herein, "therapeutic" vaccines are vaccines that are designed and administered to patients having cancer. Therapeutic vaccines are used to prevent and/or treat the development of disease in these affected individuals.

"Antigen presenting cells" ("APC") as used herein refers to cells of the immune system which present antigen on their surfaces. This antigen is recognizable by T-cells. Examples of antigen presenting cells are dendritic cells, interdigitating cells, activated B-cells and macrophages.

With regard to a particular amino acid or peptide sequence, an "epitope" is a set of amino acid residues that is involved in recognition by a particular immunoglobulin, or in the context of T-cells, those residues necessary for recognition by T-cell receptor proteins and/or Major Histocompatibility Complex (MHC) receptors. In an immune system setting, in vivo or in vitro, an epitope is the collective features of a molecule, such as primary, secondary, and tertiary peptide structure, and charge, that together form a site recognized by an immunoglobulin, T-cell receptor, or HLA molecule.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a subject or a donor subject. A donor subject is one in which an antibody is generated and isolated, the isolated antibody is then administered to a second subject. Treatment or therapy can be an active immune response induced by administration of immunogen.

For purposes of this specification and the accompanying claims the terms "epitope" and "antigenic determinant" are used interchangeably to refer to a site on an antigen to which B and/or T cells respond or recognize.

With regard to a particular amino acid sequence, an "paratope" is a set of amino acid residues of the antibody molecule that recognizes or is involved in binding an antigenic determinant or epitope of an antigen.

II. VIRUS-LIKE PARTICLES (VLPS)

Methods of using and producing RNA bacteriophage VLPs can be found, for example in international application PCT/US2012/044206, which is incorporated herein by reference in its entirety.

RNA Bacteriophages.

The system is based on the properties of single-strand RNA bacteriophages (see RNA Bacteriophages, in The Bacteriophages. Calendar, R L, ed. Oxford University Press. 2005). The known viruses of this group attack bacteria as diverse as *E. coli*, *Pseudomonas* and *Acinetobacter*. Each bacteriophage possesses a highly similar genome organization, replication strategy, and virion structure. In particular, the bacteriophages contain a single-stranded (+)-sense RNA genome, contain maturase, coat and replicase genes, and have small (<300 angstrom) icosahedral capsids. RNA bacteriophage include, but are not limited to MS2, Qβ, R17, SP, PP7, GA, MII, MXI, f4, CbS, Cb12r, Cb23r, 7s, and f2 RNA bacteriophages. Virus-like particles are readily produced when the RNA bacteriophage coat protein is expressed in bacteria from plasmids. Conditions for the purification of coat protein and for the reconstitution of its RNA binding activity from disaggregated virus-like particles have been established.

The single-strand RNA bacteriophages are found widely distributed in nature. Several have been characterized in great detail in terms of genome sequence, molecular biology, and capsid structure and assembly. MS2 is perhaps the best-studied member of the group. MS2 has a 3569-nucleotide single-strand RNA genome that encodes only four proteins: maturase, coat, lysis and replicase. The viral particle is comprised of 180 coat polypeptides, one molecule of maturase, and one copy of the RNA genome. Since the coat protein itself is entirely responsible for formation of the icosahedral shell, the RNA bacteriophage VLP can be produced from plasmids as the product of a single gene. Thus, in comparison to the other phages used for peptide display, RNA bacteriophage VLPs are strikingly simple. The engineering of MS2 and PP7 VLPs for peptide display and affinity selection has been described.

The present invention is directed to RNA bacteriophage virus-like particles comprising a heterologous peptide. The methods typically include producing VLPs in vitro and recovering the VLPs. In certain aspect VLPs are produced by *Eschericia coli* or *Pseudomonas aeruginosa* cells.

Coat Polypeptide Coat Protein.

The coat polypeptide is about 120 to 135 amino acids in length. Examples of coat polypeptides include, but are not limited to the MS2 coat polypeptide (see US20090054246), and PP7 coat polypeptide (see GenBank Accession P03630). In certain embodiments heterologous peptide sequences are inserted into the coat polypeptide.

The heterologous peptide is present at a location in the coat polypeptide such that the insert sequence is expressed on the outer surface of the capsid. In a particular embodiment, the heterologous peptide is inserted into the AB loop regions of one or both coat polypeptides. Examples of such locations in the AB loop include, for instance, insertion into a coat polypeptide immediately following amino acids 11-17, or amino acids 13-17 of the coat polypeptide, with amino acid 1 being the amino terminal amino acid of the coat protein. In certain aspects the heterologous peptide is inserted at a site corresponding to amino acids 11-17 or more particularly 13-16 of MS-2. In certain aspect 1, 2, 3, 4, 5, 6, 7, 8, 9, or 10 amino acids of the native coat protein can be modified to accommodate a heterologous peptide insertion.

In certain embodiments the coat polypeptide is a single-chain dimer containing an upstream (first) and downstream (second) subunit. Each subunit contains a functional coat polypeptide sequence. The heterologous peptide may be inserted into the upstream and/or downstream subunit at the sites mentioned herein. In a particular embodiment, the coat polypeptide is a single chain dimer of an MS2 coat polypeptide.

As used herein, the term "coat protein(s)" refers to the protein(s) of a bacteriophage or a RNA-phage capable of being incorporated within the capsid assembly of the bacteriophage or the RNA-phage.

Coat protein "AB-loop". The RNA phage coat proteins possess a conserved tertiary structure. The coat proteins possess a structure exemplified by that of MS2 coat protein. Each of the polypeptide chains is folded into of a number of β-strands designated by letters A through G. The β-strands A and B form a hairpin with a three-amino acid loop connecting the two strands at the top of the hairpin, where it is exposed on the surface of the VLP. Peptides inserted into the AB-loop are exposed on the surface of the VLP and are strongly immunogenic.

A "heterologous" peptide is a peptide which is an identifiable segment of a polypeptide that is not found in association with the larger polypeptide in nature and may include an xCT peptide.

The valency of a VLP refers to the number of copies of a heterologous peptide displayed on the particles. A virus particle which exhibits "low valency" of a heterologous peptide is a particle that displays from fewer than one to up to about ten or more heterologous peptides in the coat polypeptide dimers per virus particle on average. Virus particles which exhibit low valency are formed from a plurality of coat polypeptide dimers which are free of heterologous peptide (preferably, wild-type coat polypeptide) and a minority of coat polypeptide dimers which comprise heterologous peptide, thus forming a mosaic VLP.

III. THERAPEUTIC ANTIBODIES

Certain embodiments of the present invention is directed to an antibody, e.g., a monoclonal antibody, that recognizes human xCT for a cell expressing the same. The invention is also directed to a hybridoma cell line that produces the antibody, and to methods of treating cancer using the antibody. The antibody recognizes and specifically binds human xCT in its native form, which is expressed on the cellular membrane.

The term "antibody" is used herein in the broadest sense and refers generally to a molecule that contains at least one antigen binding site that immunospecifically binds to a particular antigen target of interest. The term "antibody" thus includes but is not limited to antibodies and variants thereof, fragments of antibodies and variants thereof, peptibodies and variants thereof, and antibody mimetics that mimic the structure and/or function of an antibody or a specified fragment or portion thereof, including single chain antibodies and fragments thereof. The term "antibody," thus includes full-length antibodies and/or their variants as well as fragments thereof. Binding of an antibody to a target can cause a variety of effects, such as but not limited to, it modulates, decreases, increases, antagonizes, agonizes, mitigates, alleviates, blocks, inhibits, abrogates and/or interferes with at least one target activity or binding, or with receptor activity or binding, in vitro, in situ, and/or in vivo.

The present invention, thus, encompasses antibodies capable of binding to a biological molecule (such as an antigen or receptor) or portions thereof, including but not limited to Fab, Fab' and F(ab')$_2$, facb, pFc', Fd, Fv or scFv fragments; diabodies; linear antibodies; single-chain antibody molecules; and multispecific antibodies formed from antibody fragments.

Accordingly, antibody is used in the broadest sense and specifically covers, for example, single anti-xCT monoclonal antibodies (including agonist, antagonist, and neutralizing antibodies), anti-xCT antibody compositions with polyepitopic specificity, single chain anti-xCT antibodies, and fragments of anti-xCT antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. In certain aspects a monoclonal antibody specifically binds an xCT peptide described herein.

Specific antibody fragments of the present invention include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv (WO 03/11161) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulfide bridges linking the VH and VL domains (Reiter et al., 1996, Nature Biotech. 14:1239-1245).

"Fv" is the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence xCT polypeptide" comprises a polypeptide having the same amino acid sequence as the corresponding xCT polypeptide derived from nature, e.g., SEQ ID NO:1. Such native sequence xCT polypeptides can be isolated from nature or can be produced by recombinant or synthetic means. The term "native sequence xCT polypeptide" specifically encompasses naturally occurring truncated or secreted forms of the specific xCT polypeptide (e.g., a loop or partial loop sequence), naturally-occurring variant forms (e.g., alternatively spliced forms) and naturally-occurring allelic variants of the polypeptide.

The terms "individual," "subject," and "patient," used interchangeably herein, refer to an animal, preferably a mammalian (including nonprimate and primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic, and/or physiologic effect. The effect may be therapeutic in terms of a partial or complete cure for a disease, symptom, and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

A. Monoclonal Antibodies

The anti-xCT antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the xCT polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) Immunol. 133:3001; Brodeur et al. (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against xCT or the xCT peptides described herein. The binding specificity of monoclonal antibodies produced by the hybridoma cells can be determined by inmunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures, e.g., by using oligonucleotide probes that are capable of binding specifically to genes encoding the heavy and light chains of murine antibodies. The hybridoma cells of the invention serve as a preferred source of such DNA. Once isolated, the DNA may be placed into expression vectors, which are then transfected into host cells, such as, simian COS cells, Chinese hamster ovary (CHO) cells, or myeloma cells that do not otherwise produce immunoglobulin protein, in order to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bifunctional or multifunctional antibody with non-identical antigenic binding specificities, each of which may be monovalent, bivalent, or multivalent.

The antibodies of the present invention may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof can be accomplished using routine techniques known in the art.

The anti-xCT monoclonal antibodies of the invention may be whole or an antigen-binding fragment of the antibody that binds to a xCT polypeptide, preferably a native sequence xCT polypeptide. Furthermore, in a preferred embodiment the monoclonal antibody is identified as having recognition of a xCT protein from at least one cancer cell line.

In one non-limiting embodiment the monoclonal antibody is produced by the hybridoma cell line, wherein said antibody or functional fragment thereof binds to a XCT protein and wherein said antibody or functional fragment thereof binds a CSC, neoplastic cell, or antigen thereof as said antibody or functional fragment thereof.

B. Human and Humanized Antibodies

The monoclonal antibodies of the present invention can be human or humanized to reduce the immunogenicity for use in humans. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al., European Patent EP0125023 (published Mar. 3, 2002); Taniguchi et al., European Patent EP0171496 (published May 26, 1993); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84:3439; Sun et al. (1987) Proc. Natl. Acad. Sci. USA 84:214; Better et al. (1988) Science 240:1041. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, Science 229:1202-1207 by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPIIbIIIa antibody producing hybridoma. The recombinant DNA encoding the chimeric antibody can then be cloned into an appropriate expression vector.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature 321:522; Riechmann et al. (1988) Nature 332:323; Verhoeyen et al. (1988) Science 239:1534), by substituting rodent CDRs or CDR sequences for the corresponding sequences of a human antibody. See also U.S. Pat. No. 5,225,539 and Beidler et al. 1988 J. Immunol. 141:4053. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al. J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al. J. Immunol., 147(1):86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. Bio/Technology 10:779 (1992); Lonberg et al. Nature 368:856 (1994); Morrison, Nature 368:812 (1994); Fishwild et al. Nature Biotechnology 14:845 (1996); Neuberger, Nature Biotechnology 14:826 (1996); Lonberg and Huszar, Intern. Rev. Immunol. 13:65 (1995).

C. Pharmaceutical Compositions of Antibodies

In other embodiments there is provided a pharmaceutical composition including an antibody as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of an antibody, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies is intended to include any art recognized pharmaceutically acceptable salts, including for example, organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents, for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions may further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents, and/or preservatives. Alternatively, compositions of the present invention may be formulated as a lyophilisate.

While any suitable carrier known to those of ordinary skill in the art may be employed in the compositions of this invention, the type of carrier will typically vary depending on the mode of administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation which can be formulated in such a manner as to permit a sustained release of the active ingredient. An exemplary composition may comprise antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions, or solid or powder forms suitable for reconstitution with suitable vehicles, including by way of example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers, or other known encapsulating technologies.

The pharmaceutical compositions described herein may be presented in unit-dose or multi-dose containers, such as sealed ampules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a lyophilized condition requiring only the addition of a sterile liquid carrier immediately prior to use.

D. Uses for Anti-XCT Antibodies

The anti-XCT antibodies of the invention have various utilities. In one embodiment, the anti-XCT antibodies can be immobilized on a suitable support, such as a Sephadex resin or filter paper, using methods well known in the art. The immobilized antibody then is contacted with a sample containing xCT to be bound or purified, and thereafter the support is washed with a suitable solvent that will remove substantially all the material in the sample except the xCT material bound to the immobilized antibody.

In another embodiment, provided is a method of treatment of a disease, such as cancer. The method of the invention preferably includes the step of providing an antibody or xCT antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include, for example, complement-mediated cytolysis, antibody-dependent cellular cytotoxicity (ADCC)1 modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic, chemotherapeutic, or therapeutic agents, such as radioligands or cytosolic toxins, and may also be used therapeutically to deliver the toxic or therapeutic agent directly to tumor cells.

Treatment is meant to include therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use nonmodified antibodies or antibodies conjugated with a therapeutic compound, such as a toxin or cytotoxic molecule, depending on the functionality of the antibody. Generally, when nonmodified antibodies are used, they will typically have a functional Fc region. By "functional Fc region" herein is meant a minimal sequence for effecting the biological function of Fc, such as binding to Fc receptors, particularly FcγR (e.g., Fcγ RI, FcγRII, and Fcγ RIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation.

In this regard, polyclonal antibodies, or mixtures of monoclonals will be advantageous because they will bind to different epitopes and, thus, have a higher density of Fc on the cell surface as compared to when a single monoclonal antibody is used. Of course, to enhance their effectiveness in depleting targeted cells, or where nonmodified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention may include, for example, PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state or condition of the subject, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery, half-life of the antibodies, and efficacy of the antibodies. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12:60 describes in vitro measurements of antibody dependent cellular cytoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining the LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmacological Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences, for example, in the case of a chimeric or humanized antibody. Within certain embodiments, an initial high dose of antibody is administered such that a degree of immunological tolerance to the therapeutic antibody is established. The tolerizing dose is sufficient to prevent or reduce the induction of an antibody response to repeat administration of the committed progenitor cell specific antibody.

Ranges for the tolerizing dose are, for example, between 10 mg/kg body weight to 50 mg/kg body weight, inclusive. In some embodiments, ranges for the tolerizing dose are between 20 and 40 mg/kg, inclusive. In still other embodiments, ranges for the tolerizing dose are between 20 and 25 mg/kg, inclusive.

Within these therapeutic regimens, the therapeutically effective dose of antibodies may be administered in the range of 0.1 to 10 mg/kg body weight, inclusive. In certain embodiments, therapeutically effective doses are in the range of 0.2 to 5 mg/kg body weight, inclusive. In other embodiments, therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

Antibody compositions may be formulated for any appropriate manner of administration, including for example, oral, nasal, mucosal, intravenous, intraperitoneal, intradermal, subcutaneous, and intramuscular administration.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

In another embodiment, anti-xCT antibodies may be used in diagnostic assays for xCT, e.g., detecting its expression in specific cells, tissues, or serum. Various diagnostic and prognostic assay techniques known in the art may be used, such as competitive binding assays, direct or indirect sandwich assays and immunoprecipitation assays conducted in either heterogeneous or homogeneous phases (Zola (1987) Monoclonal Antibodies: A Manual of Techniques, CRC Press, Inc. pp. 147-1581). The antibodies used in the assays can be labeled with a detectable moiety. The detectable moiety should be capable of producing, either directly or indirectly, a detectable signal. Any method known in the art for conjugating the antibody to the detectable moiety may be employed, including those methods described by Hunter et al. (1962) Nature 144:945; David et al. (1974) Biochemistry 13:1014; Pain et al. (1981) J. Immunol. Meth. 40:219; and, Nygren, J. (1982) Histochem. and Cytochem. 30:407.

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

"Immunoassay" refers to a method of detecting an analyte in a sample involving contacting the sample with an antibody that specifically binds to the analyte and detecting binding between the antibody and the analyte.

"Immunohistochemical" (abbreviated IHC) refers to specific binding agents, such as polyclonal and monoclonal antibodies, which recognize and mark antigens of interest, often by a chemical that shows that the agent has bound to the antigen of interest. An example of an IHC agent is a xCT monoclonal antibody.

The present invention relates to diagnostic assays, both quantitative and qualitative for detecting levels of xCT polypeptide in cells, tissues and bodily fluids, including determination of normal and abnormal levels. Assay techniques that can be used to determine levels of a polypeptide, such as xCT of the present invention, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to xCT, preferably a monoclonal antibody. In addition, a reporter antibody generally is prepared which binds specifically to xCT. The reporter antibody is attached to a detectable reagent such as a radioactive, fluorescent or enzymatic reagent, for example horseradish peroxidase enzyme or alkaline phosphatase.

The above tests can be carried out on samples derived from subjects' bodily fluids and tissue extracts (homogenates or solubilized tissue) such as from tissue biopsy and autopsy material. Levels of xCT, determined in cells and tissues from a patient suspected of suffering from cancer by measuring the polypeptide or by transcription levels, are compared to levels of xCT in normal or control cells or tissues. Increased levels of xCT measured in the subject as compared to levels in the same cells, tissues, or bodily fluids obtained from normal, healthy individuals are indicative of cancer. By "increased levels" it is meant an increase in measured xCT levels in a subject as compared to xCT levels in the same normal cells or tissues. Detection of increased xCT levels is useful in the diagnosis of various cancers including, but not limited to, breast cancer, pancreatic cancer, prostate cancer, melanoma, colon cancer, lung cancer, and thyroid cancer.

Further, monitoring of xCT levels in a subject diagnosed with cancer is useful in determining the onset of metastases in cancers that have not yet metastasized and in determining the stage of the cancer. For example, detection of xCT can be used in a method of monitoring cancer in a subject that has not metastasized for the onset of metastasis. In this method, a subject suffering from a cancer that is not known to have metastasized is identified. xCT levels in a sample from the subject are then measured. These measured xCT levels are then compared with levels of xCT from a normal control sample. An increase in measured xCT levels in the subject versus the normal control is associated with a cancer that has metastasized.

The stage of cancer in a subject suffering from can also be determined. In this method a subject suffering from cancer is identified. xCT levels in a sample of tissue from the patient are measured to establish a baseline xCT level for said patient. xCT levels in samples of the same tissue are then determined at subsequent time periods such as scheduled check-ups with the subject's physician. Measured xCT levels are then compared with the baseline xCT levels for the patient. In this method, an increase in measured xCT levels in the subject versus baseline xCT levels in the subject is associated with a cancer that is progressing and a decrease in measured xCT levels versus baseline xCT levels is associated with a cancer that is regressing or in remission. Increases in measured xCT levels as compared to baseline xCT levels established for the subject may also be indicative of metastases.

In one embodiment, xCT immunohistochemistry functions as an "index diagnostic" to assign risk based on the presence of xCT expression. Therefore, based on this and other parameters (e.g., size of lesion), one can determine whether or not different therapeutic modalities (i.e., chemotherapy, radiation therapy, surgery) should be used. In a related aspect, methods for monitoring progression of premalignancy into a malignant phenotype are disclosed. For example, by using serial sampling (i.e., biopsy) of the tissue and observing the state of xCT expression in the lesions, one can determine whether or not the premalignancies are progressing in a way that would indicate whether therapeutic intervention is advised or is successful.

One aspect of the invention is a method to determine the likelihood of a group of cells to become cancerous, e.g., the cells or glands become premalignancies or progress to cancerous lesions. The invention utilizes an agent, such as an antibody, that specifically binds to xCT protein to assess levels of xCT in tissue and cells. xCT expression in cells and tissue may also be assessed using nucleic acid analysis, such as selective amplification, or hybridization methods. A level of xCT above normal or control levels, indicates an increased likelihood that premalignant disease is present, i.e., that the cells or tissues are premalignant.

E. Antibody Kits

Antibody kits are provided which contain the necessary reagents to carry out the assays of the present invention. The kit may include one or more compartments, each to receive one or more containers such as: (a) a first container comprising one of the components of the present invention described above; and (b) one or more other containers comprising one or more of the following: wash reagents, reagents capable of detecting presence of the antibody or peptide.

The containers allow the efficient transfer of reagents from one compartment to another compartment such that the samples and reagents are not cross-contaminated, and the agents or solutions of each container can be added in a quantitative fashion from one compartment to another.

The kit typically contains containers that may be formed from a variety of materials, such as glass or plastic, and can include for example, bottles, vials, syringes, and test tubes. A label typically accompanies the kit, and includes any writing or recorded material, which may be in electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies of the present invention can be readily incorporated into one of the established kit formats that are well known in the art.

All patent and literature references cited in the present specification are hereby incorporated by reference in their entirety.

The following examples are offered for illustrative purposes only, and are not intended to limit the scope of the present invention in any way.

IV. ANTI-CANCER THERAPIES

An object of the present invention is to provide methods and compositions relating to a vaccine against cancer and in particular breast cancer. In certain aspect cancer cells escaping surgical removal or killing by chemotherapies are targeted. In certain aspects administration of nucleic acid of the invention causes a triggering of a human immune response that brings about the killing of human cells that produce human-xCT. In accordance with another aspect of the invention, a method of treating humans includes steps for introducing an xCT-DNA sequence into a human.

In accordance with another aspect of the invention, the use of a DNA sequence is provided for providing an antigen for the preparation of a vaccine for administration to humans to provide an immune response to the antigen in humans.

In accordance with another aspect of the invention, a method of treating cancer in humans is provided which includes the step of introducing a nucleic acid configured to express all or part of the xCT protein in a human for triggering a human immune response which produces antibodies against human-xCT.

In accordance with another aspect of the invention, a method of delivering a nucleic acid vaccine expressing an antigen into human cells is provided which includes the steps of administering a quantity of the nucleic acid vaccine to human tissue, whereby the nucleic acid vaccine expressing the antigen is delivered into cells in the human tissue.

In accordance with another aspect of the invention, the use of a vector expressing an antigen is provided for the preparation of a vaccine for administration to humans to provide an immune response against the antigen. In one respect, the vector is can be a DNA vector. In another respect, the vector can be an RNA vector.

In certain embodiments the compositions and methods described herein in can be administered in conjunction or combination with other anti-cancer therapies for the treatment of cancer. Therapeutically effective doses can be determined by one of skill in the art and will depend on the severity and course of the disease, the patient's health and response to treatment, the patient's age, weight, height, sex, previous medical history and the judgment of the treating physician.

In some methods of the invention, the cancer cell is a tumor cell. The cancer cell may be in a patient. The patient may have a solid tumor. In such cases, embodiments may further involve performing surgery on the patient, such as by resecting all or part of the tumor. xCT VLPs described herein can be administered before, during, or after an anti-cancer treatment. Anti-cancer treatments may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Anti-cancer compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, docetaxel, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

In some embodiments, the cancer that is administered the composition(s) described herein may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell. In certain aspects the cancer is breast cancer.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 xCT RNA Bacteriophage Virus-Like Particle (VLP)

VLPs expression plasmids displaying extracellular domains (ECD) of human xCT were constructed. Amino acid sequences were codon optimized for expression in *E. coli* and were inserted into the AB loop of MS2. The displayed sequences were discovered in a manuscript determining the membrane topology of human xCT (hyperlink found below; FIG. 9).

VLP displaying xCT ECD 3, 5, and 6 were produced and were used to immunize BALB/c mice. VLP displaying xCT ECD 1, 2 and 4 did not produce soluble protein in the MS2 system.

Antibody Response to xCT VLP Immunization.

Figure 1B:
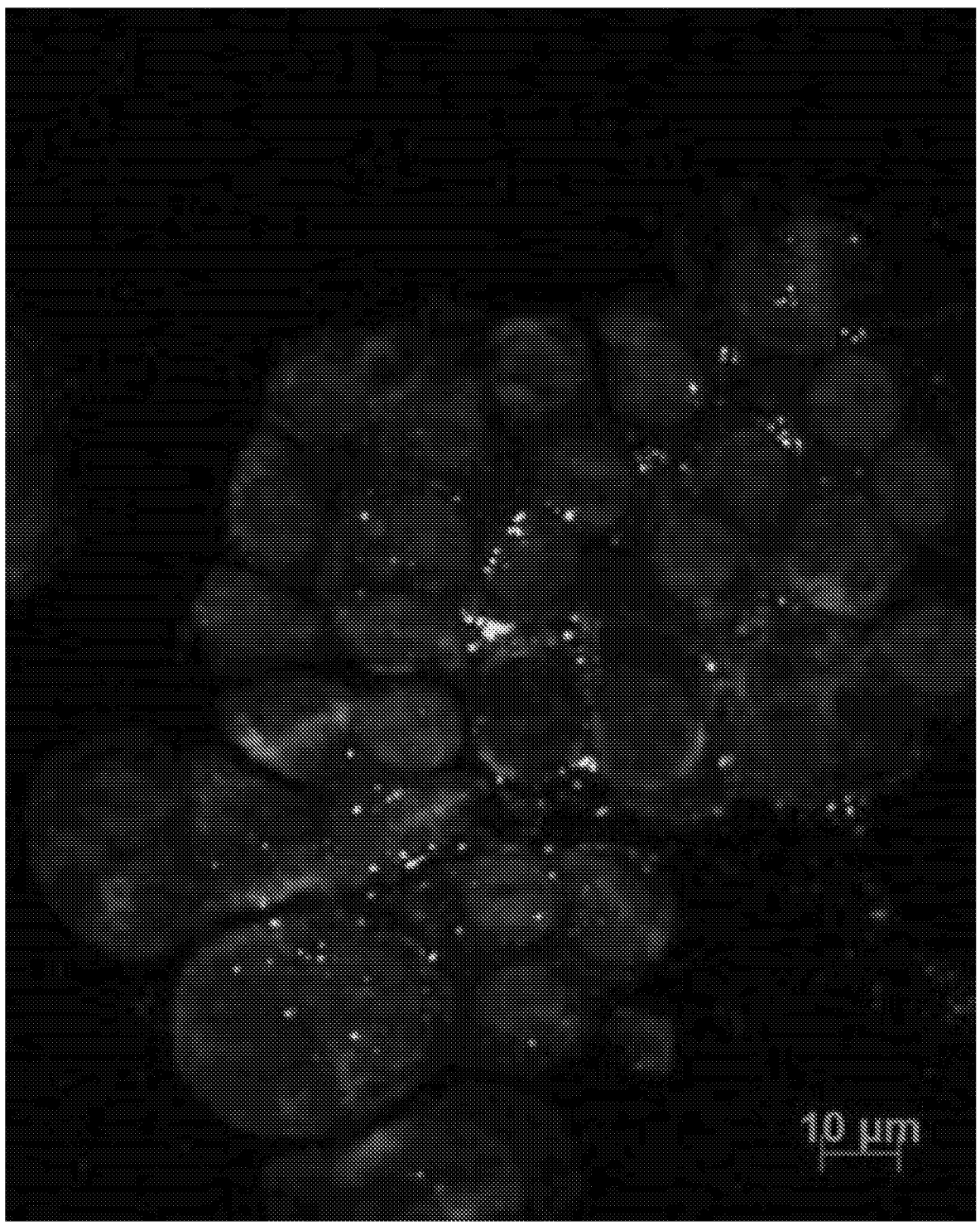

To determine if xCT VLP vaccination generated antibodies that could bind to breast cancer stem cells, sera from animals immunized with VLPs 3 times at 2 week intervals were incubated with passage 2 tumorspheres from the human cell line HCC-1806. As seen in FIG. 1, animals vaccinated with MS2 VLPs displaying ECD 3, and 6 generated antibodies against xCT that were able to bind to human breast cancer cells as well as a commercially available xCT antibody. VLPs displaying xCT ECD5 generated a lower, but detectable antibody response as measured by FACS Analysis of Breast Cancer Metastatic Spread in xCT Immunize.

Figure 2:
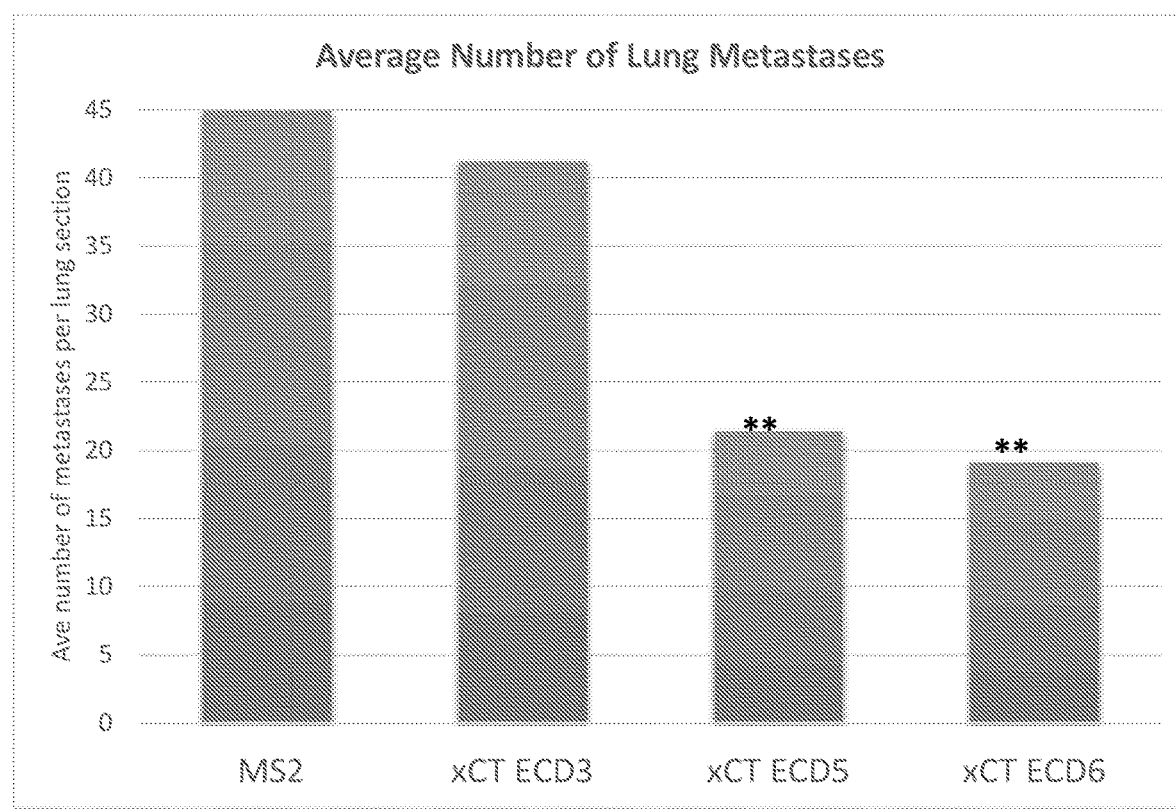
FIG. 2. Immunization with xCT VLPs significantly inhibit lung metastases. Mice immunized with xCT or MS2 control VLPs were injected (i.v) with $5 \times 10^4$ mouse tubo-derived tumorspheres. 20 days later, animals were euthanized and lungs were removed, section and the number of metastatic foci were measured. The number of mice were MS2 (n=2), xCT ECD3 (n=5), xCT ECDS (n=5) and xCT ECD6 (n=4). Metastatic lesions were counted from two lung sections per animal. Data presented is the average number of lesions per slide. Two-tailed student t test was used to determine significance. ** indicates a p-value<0.01.

Inhibition of xCT function by a DNA based vaccine inhibits the number of metastatic lesions in the lung by 40% in a well characterized breast cancer stem cell transplantation model. To investigate if xCT VLP vaccination would also inhibit metastatic disease, tumorspheres were injected into VLP immunized animals and the number of lung metastases were measured. As seen in FIG. 2, immunization with xCT VLPs displaying either ECD5 or ECD6 significantly reduced the number of metastases in the lung by ~60%. xCT VLP immunization reduced the number of lesions to a greater extent than the DNA-based xCT vaccination approach.

Example 2

Immunotargeting of Antigen xCT Attenuates Stem-Like Cell Behavior and Metastatic Progression in Breast Cancer A. Results xCT is Upregulated in Breast CSC.

To identify the transcripts associated with mouse and human mammary CSC, the transcription profile of Her2♭b murine TUBO cells, which had been cultured as an epithelial monolayer, were compared with the profiles of the first three in vitro passages of their derived tumorspheres (P1, P2, and P3) using MouseWG-6 v2.0 Illumina beadchips (GSE21451). This analysis uncovered a cluster of transcripts whose expression rose, as well as three clusters whose expression decreased from TUBO through P1 to P3 cells.

Figure 3A:
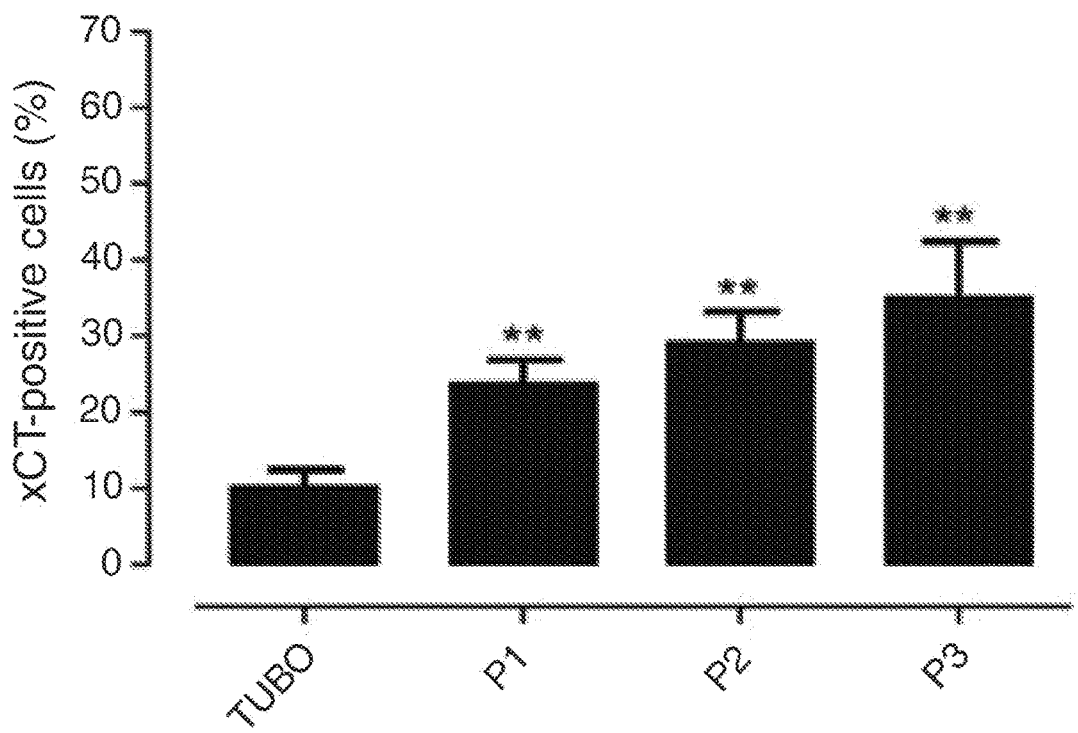
FIG. 3A-3G. xCT expression in breast CSC and tumors. (A) FACS analysis of xCT expression in TUBO cells and P1 to P3 tumorsphere passages over six independent experiments. (B) representative density plots of xCT and Sca-1 expression on TUBO and tumorspheres. Numbers show the percentage of cells in each quadrant. (C) Representative immunofluorescence staining of xCT, Sca-1, OCT4, and Thy1.1 on tumorspheres. DAPI stains the nucleus. Scale bar, 20 µm. (D) Representative density plots of xCT expression in TUBO cells stained with CD44 and CD24. (E) FACS analysis of xCT expression in HCC-1806, MDA-MB-231, and 4T1 cells and their derived tumorspheres over three independent experiments. *, $P<0.05$; , $P<0.01$; *, $P<0.001$, Student t test. (F) Immunofluorescence of xCT expression in normal breast, hyperplastic, and IDC breast carcinoma. Scale bar, 20 µm. (G) percentage of $xCT^+$ samples in normal mammary gland and in TNBC, $Her2^+$, or $ER^+/PR^+Her2^-$ breast cancer subtypes.
Figure 3B:
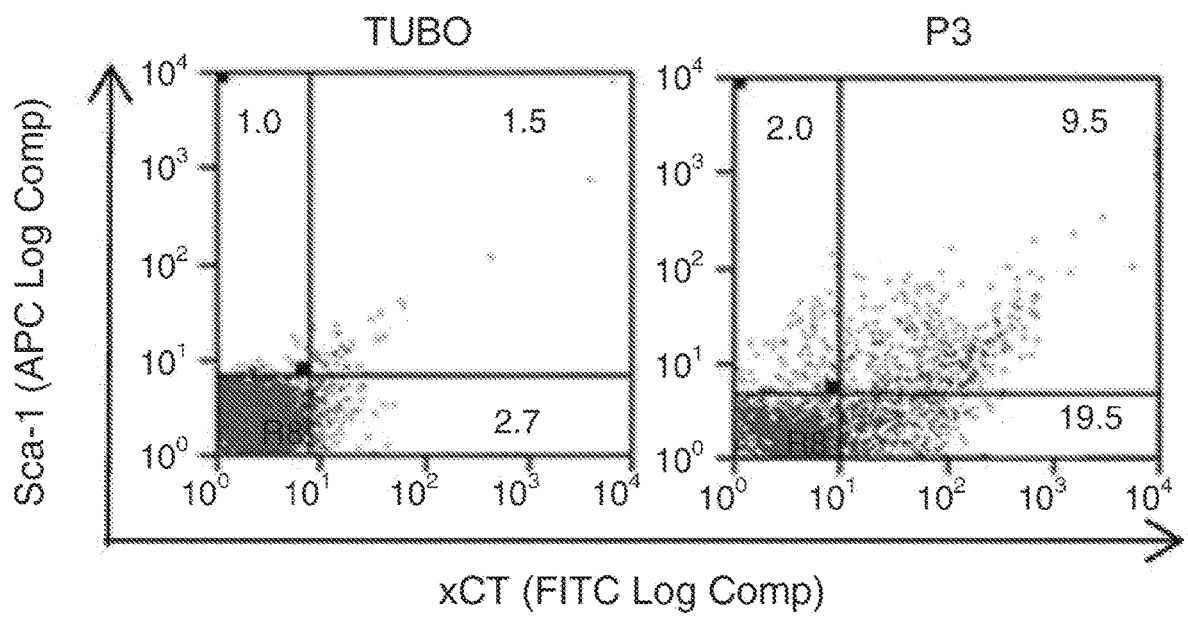
Figure 3C:
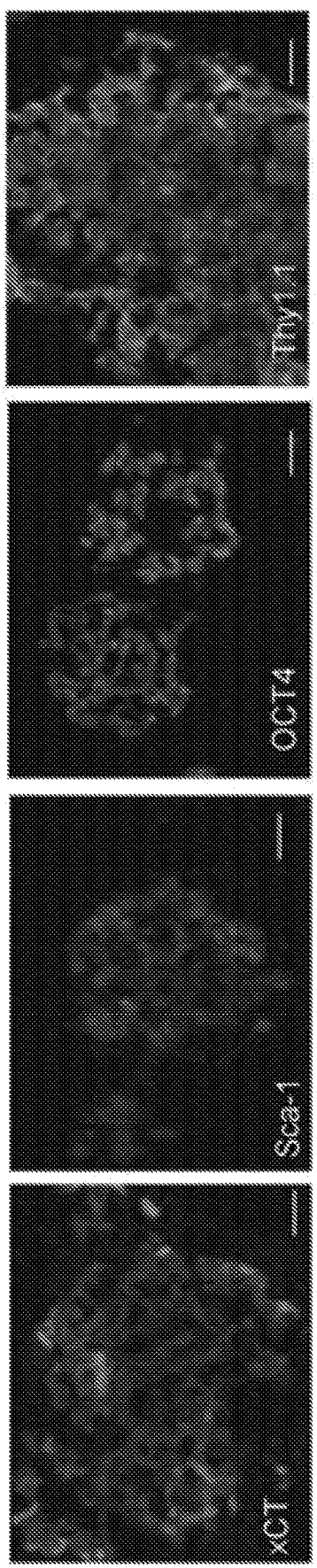
Figure 3D:
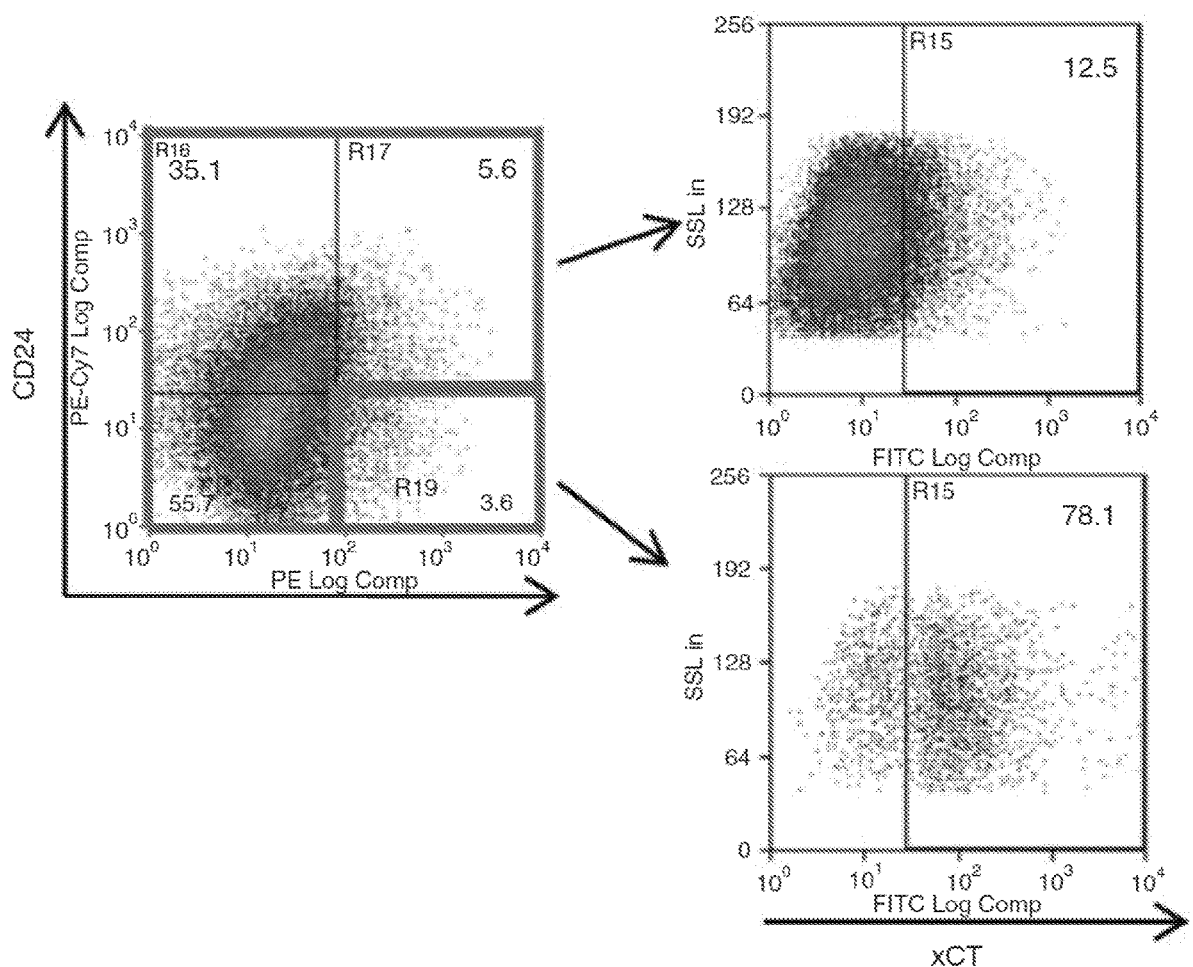
Figure 3E:
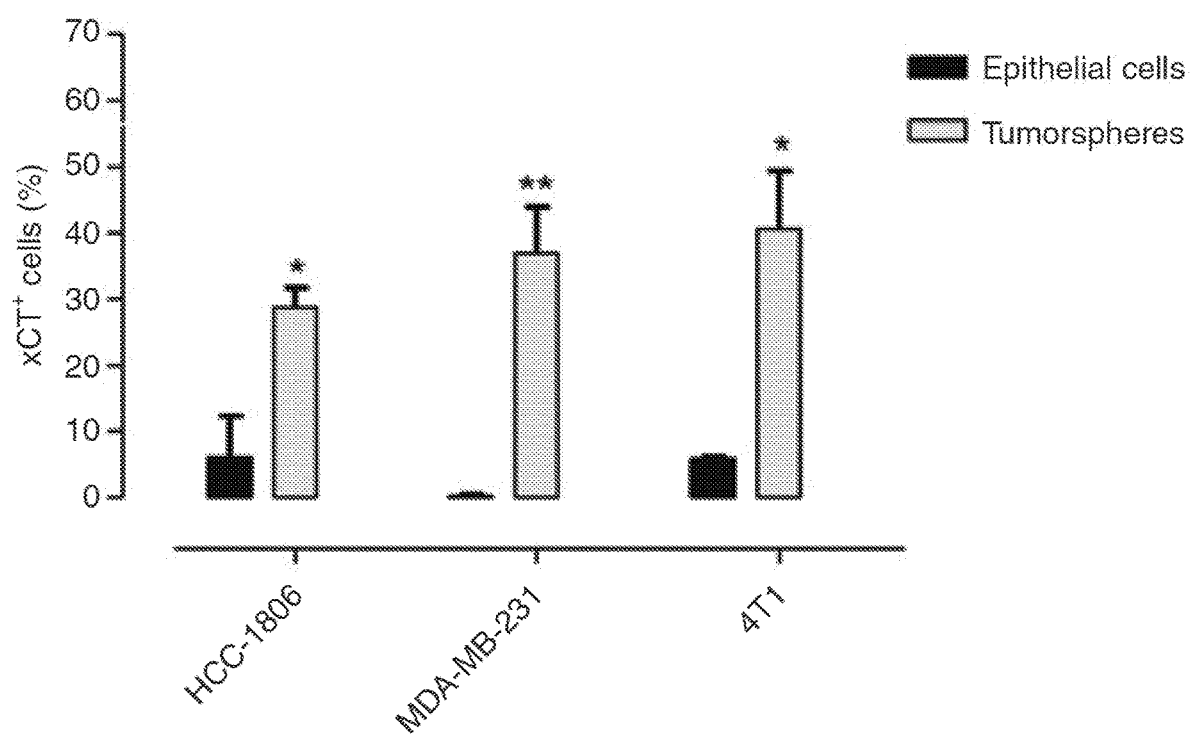
Figure 3F:
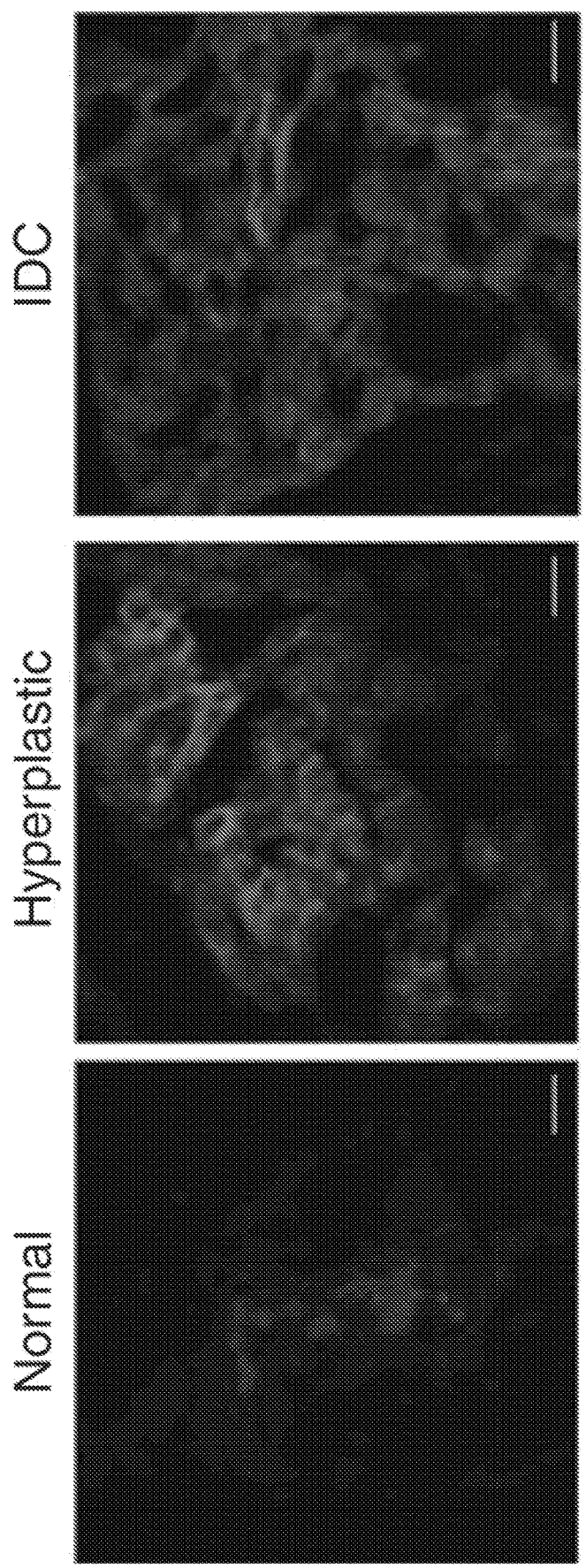
Figure 3G:
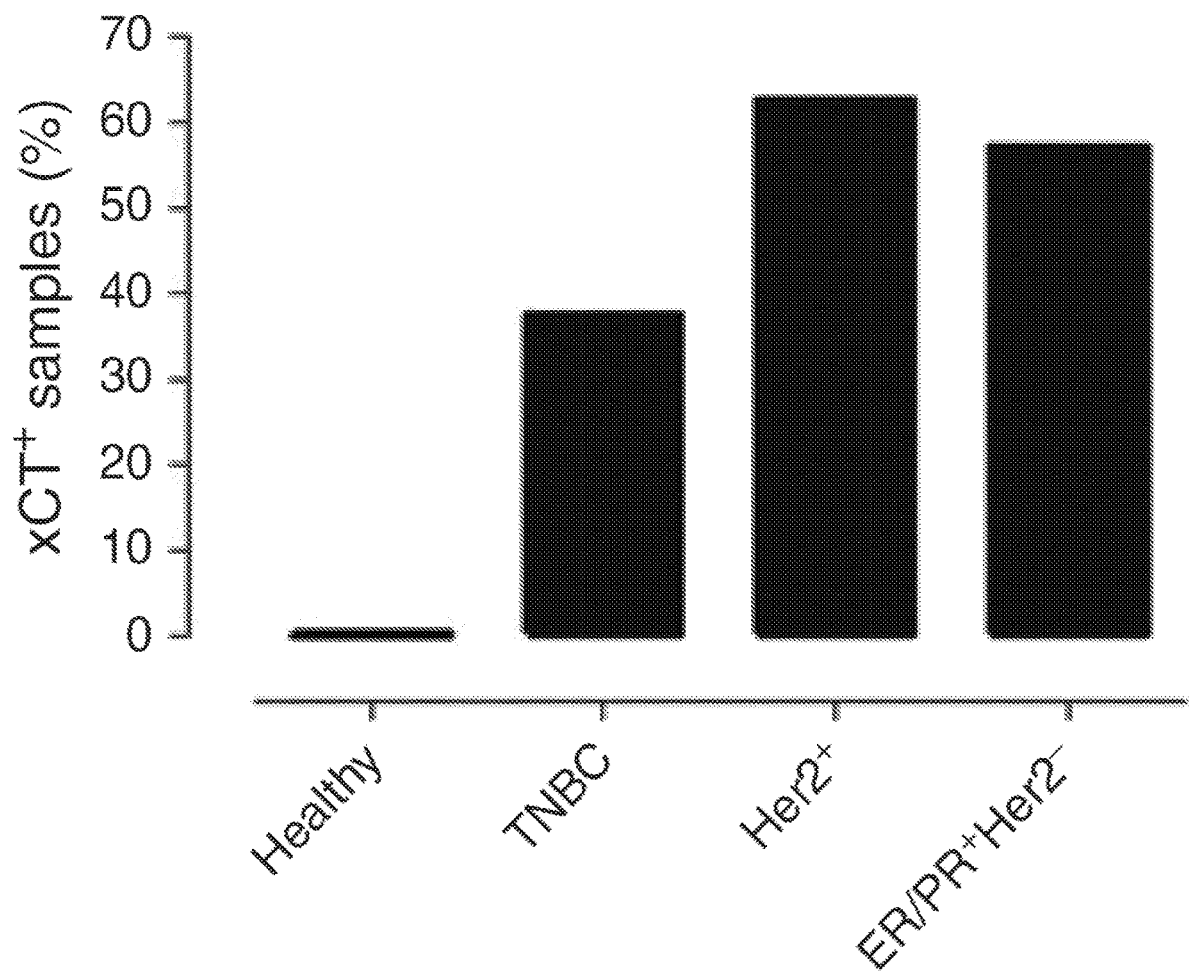

A ranking procedure was devised according to the clinical outcome of tumors expressing the transcripts that were found to increase in tumorspheres, using data from six public human breast cancer data sets. One of the genes with the best clinical outcome score was xCT (Slc7a11), whose expression increased progressively from TUBO to P3 tumorspheres, as confirmed by FACS (FIG. 3A) and qPCR analyses. Interestingly, most P3-derived cells that express the stem cell marker Sca-1 (26) are also xCT+ (FIG. 3B). The immunofluorescence analysis revealed widespread xCT positivity in tumorspheres that are essentially composed of CSC, as confirmed by Sca-1, OCT4, and Thy1.1 marker expression patterns (FIG. 3C). xCT upregulation is a feature of breast CSC and is not due to tumorsphere culture conditions, because it was also observed on the small $CD44^{high}/CD24^{low}$ CSC population present in TUBO cells (FIG. 3D). Moreover, xCT upregulation is not restricted to TUBO-derived CSC as it was also observed in tumorspheres derived from mouse (4T1) and human (HCC-1806 and MDAMB-231) triple negative breast cancer (TNBC) cell lines (FIG. 3E), suggesting that xCT may be a hallmark of breast cancer CSC.

xCT expression in the TMA of normal and neoplastic samples was evaluated to address its distribution in human cancers. xCT expression was low in normal mammary glands (FIG. 3F, left) as it was in the other normal tissues tested. By contrast, xCT was expressed at high levels in many neoplastic tissues, including hyperplastic mammary lesions and invasive ductal breast carcinomas (IDC; FIG. 3F, middle and right) displaying a pattern in which it is confined to neoplastic cells. In particular, the studies showed found xCT expression in 62% of Her2+, 57% of estrogen/progesterone receptor$^-$Her2$^-$(ER/PR$^+$Her2$^-$), and 35% of TNBC samples (FIG. 3G), suggesting that xCT may well be a commonly upregulated target in breast cancers.

xCT Downregulation Impairs Tumorsphere Generation and Alters Intracellular Redox Balance.

Figure 4A:
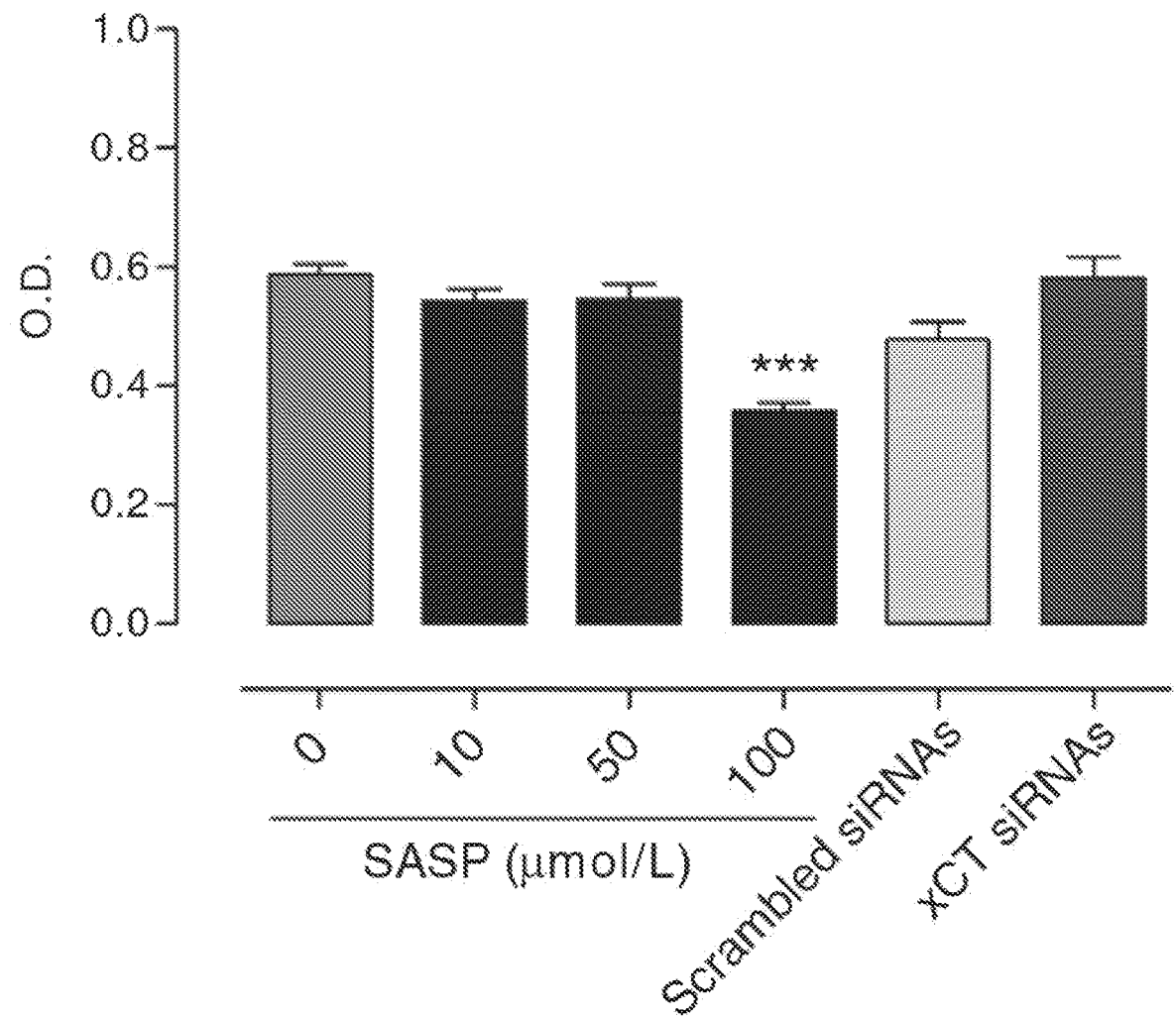
FIG. 4A-4H. xCT regulates CSC self-renewal and the intracellular redox balance. A and B, MTT assay of the cytotoxic effect exerted by scalar doses of SASP or by anti-xCT siRNAs on TUBO (A) and tumorspheres (B). (C) Sphere generation ability relative to untreated cells of tumorspheres incubated with SASP. (D) Sphere generation ability of tumorspheres incubated with siRNAs to xCT, scrambled siRNAs, or not at all shown as tumorsphere number/$10^3$ plated cells. (E) and (F) FACS analysis of xCT and CSC marker expression in spheres 24 hours after transfection with siRNAs to xCT or scrambled siRNAs. (E) histograms show xCT expression; open histograms show the background of negative control IgG stained cells from one representative experiment. (F) relative expression (%) of $xCT^+$, $Sca-1^+$, and $CD44^{high}/CD24^{low}$ cells in tumorsphere-derived cells transfected with siRNAs to xCT (black bars) compared with cells transfected with scrambled siRNAs (dashed line). G and H, GSH (G) and ROS (H) levels in TUBO cells and their derived tumorspheres after either seeding in normal conditions, transfection with siRNAs to xCT, or scrambled siRNAs over three independent experiments. *, $P<0.05$; , $P<0.01$; *, $P<0.001$, Student t test.
Figure 4B:
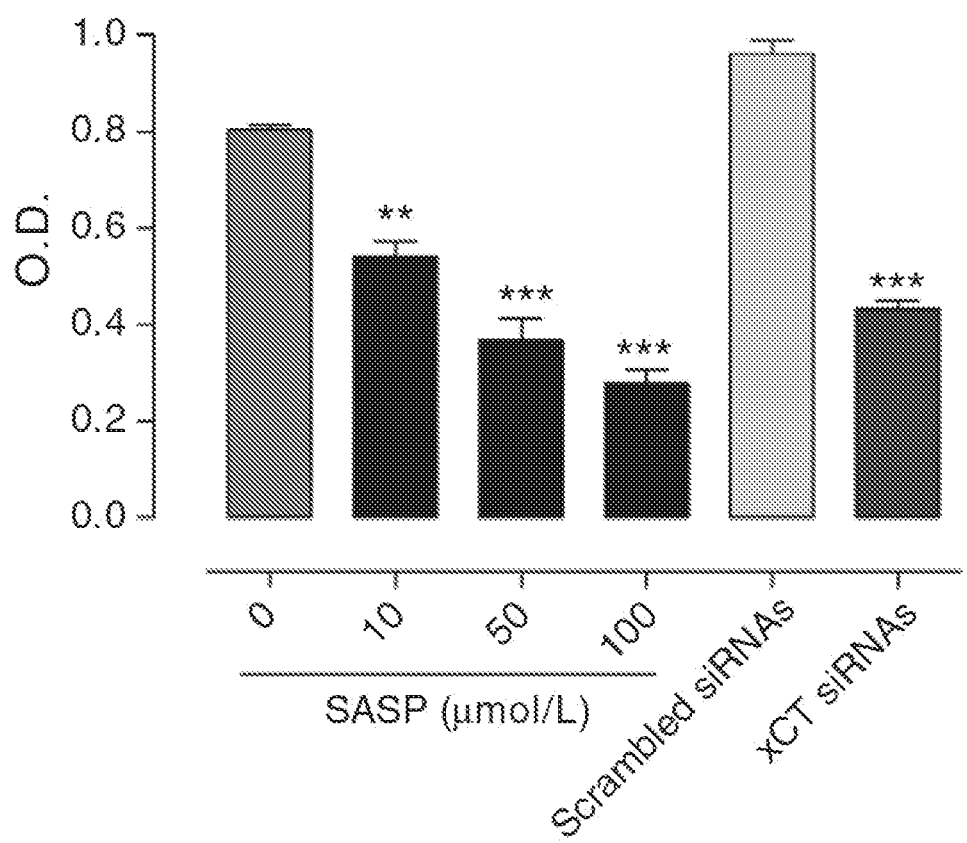
Figure 4C:
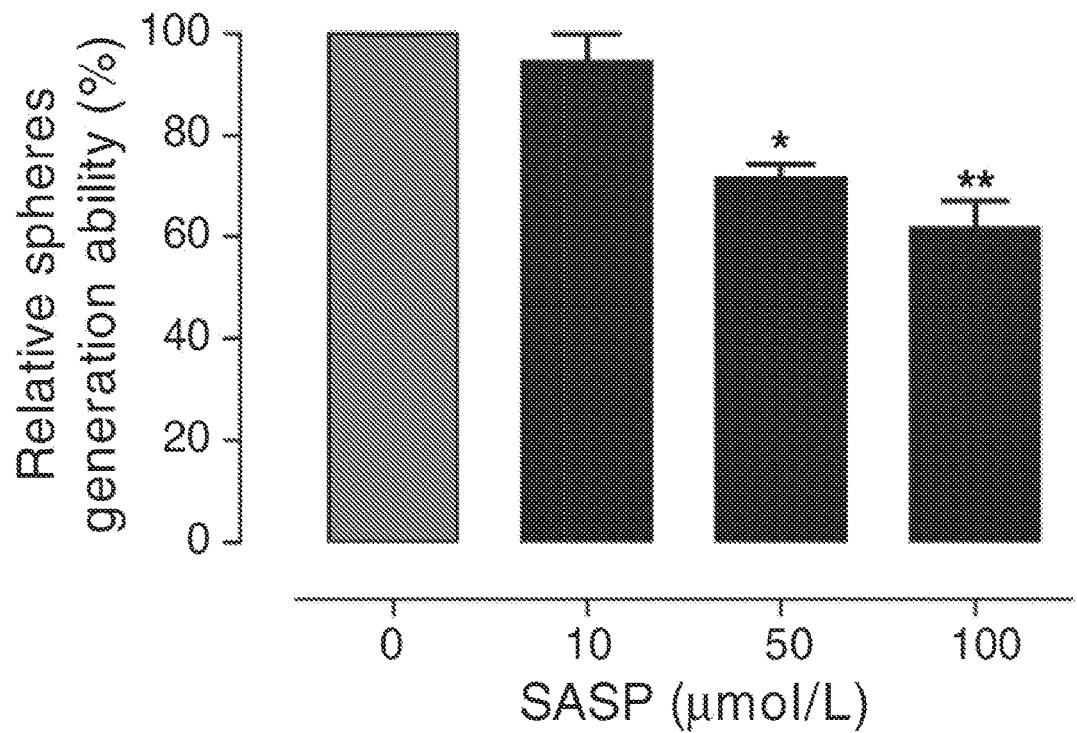
Figure 4D:
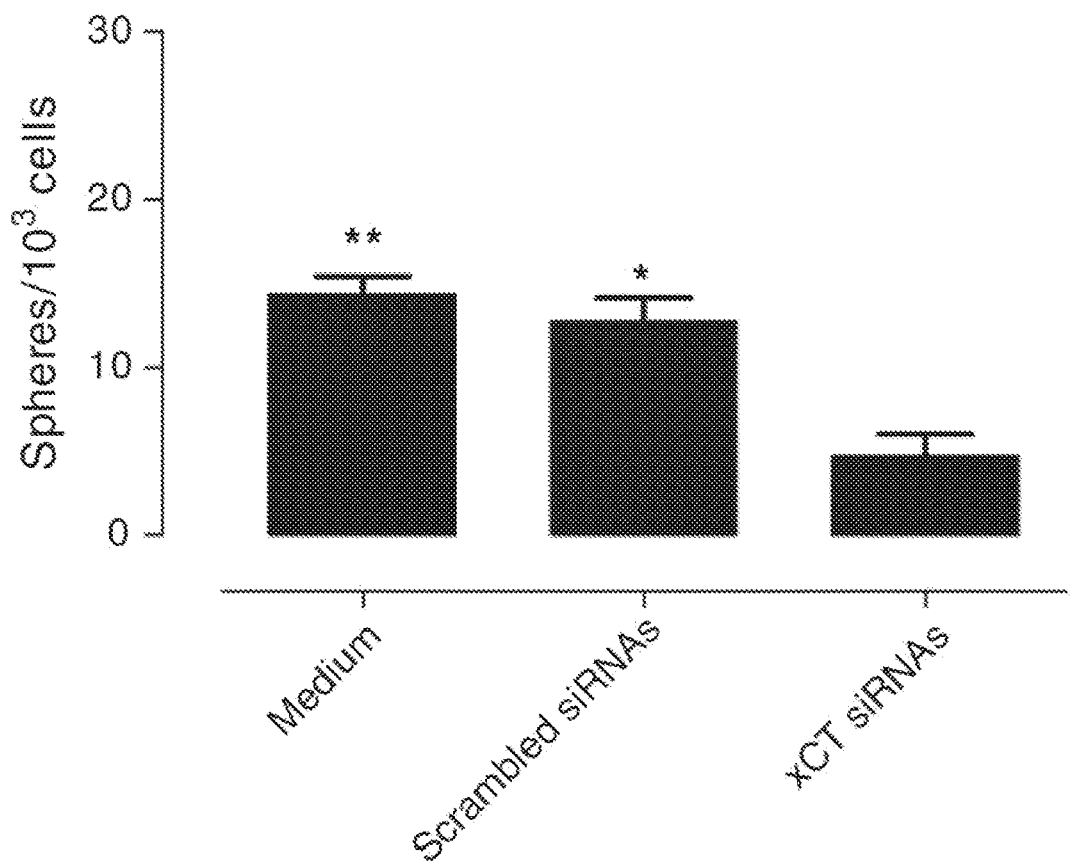
Figure 4E:
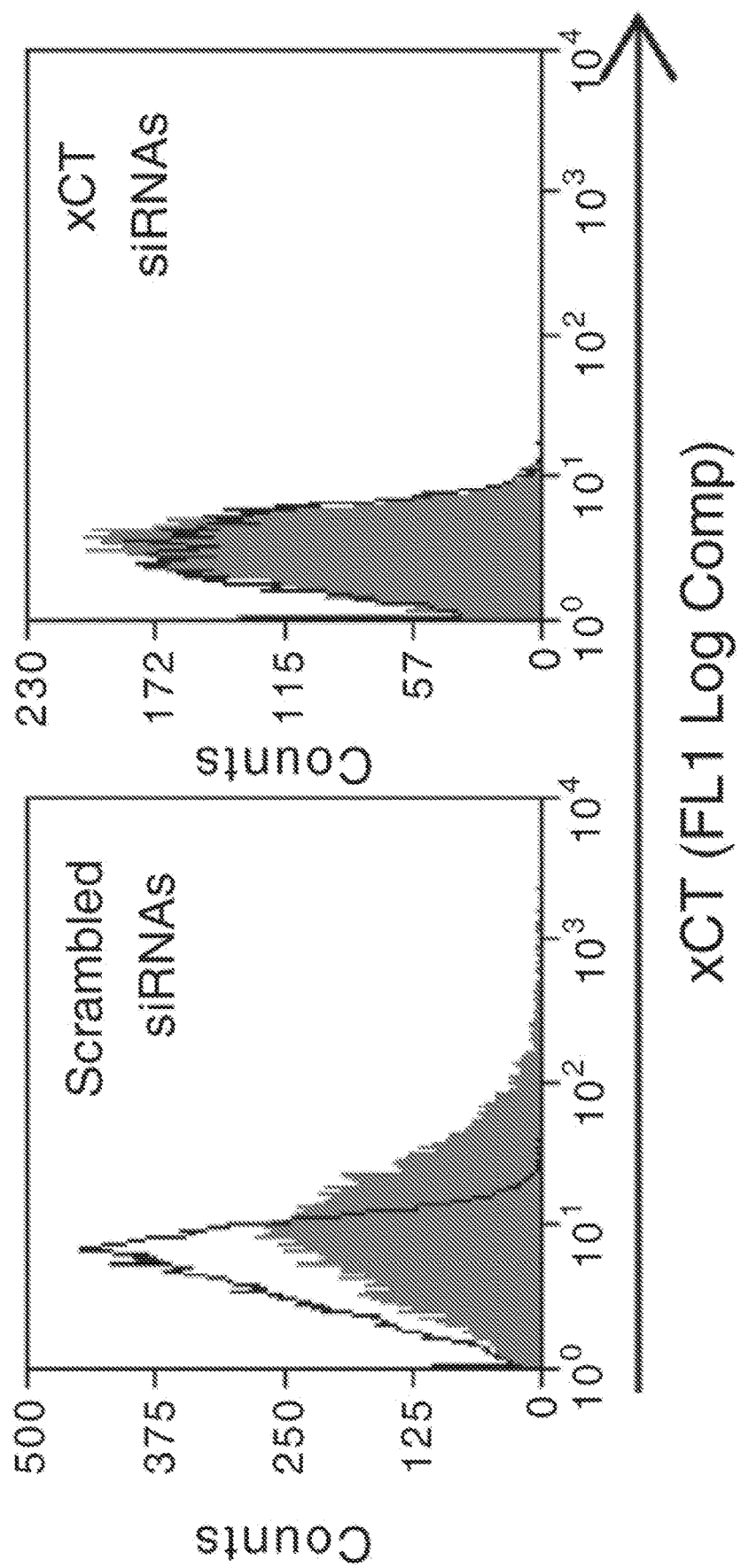
Figure 4F:
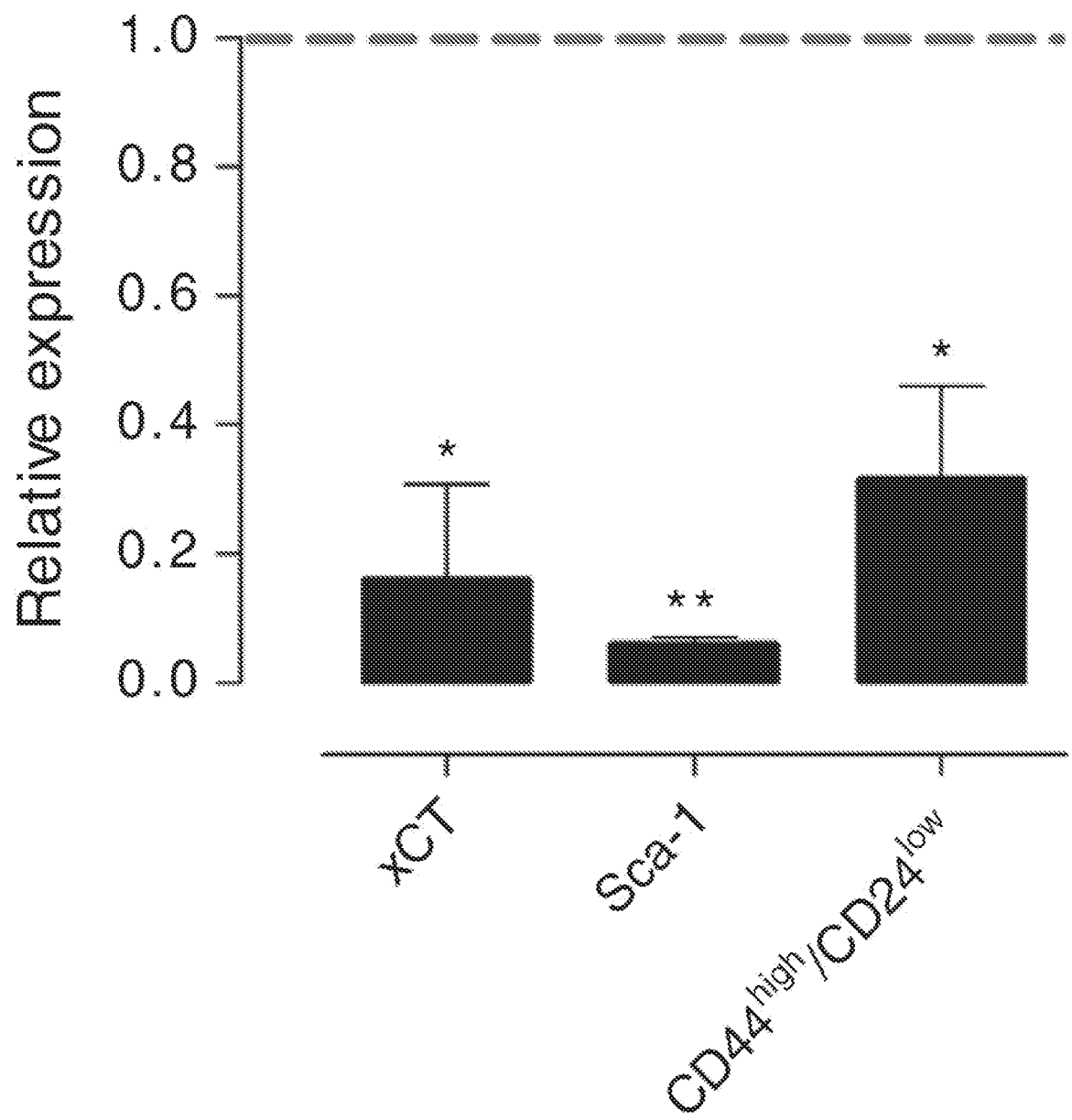

A MTT test was performed on TUBO cells and tumorspheres that had either been treated or not with scalar doses of xCT inhibitor SASP. Although SASP did not decrease TUBO cell viability, except for the highest dose (100 μmol/L; IC$_{50}$, 126.1±25.7 μmol/L; FIG. 4A), tumorsphere viability was inhibited in a dose-dependent manner (IC$_{50}$, 51.6±3.5 μmol/L; FIG. 4B), suggesting that CSC are sensitive to xCT inhibition. Similarly, xCT silencing through a pool of specific siRNAs impaired tumorspheres but not TUBO cell viability (FIGS. 4A and 4B). Moreover, SASP treatment and xCT silencing impaired tumorsphere generation (FIGS. 4C and 4D). FACS analyses performed 24 hours after siRNA transfection showed that the reduction in xCT$^+$ cells (FIGS. 4E and 4F) is accompanied by a reduction in CSC, i.e., Sca1$^+$ and CD44$^{high}$/CD24$^{low}$ cells (FIG. 4F). On the contrary, xCT overexpression increases colony generating ability, as confirmed by the higher number of colonies generated in soft agar by NIH/3T3 and HEK-293 cells transfected with xCT when compared with the corresponding cells transfected with empty plasmids. Taken together, these data suggest that xCT plays an important role in CSC maintenance and sphere generation.

Figure 4G:
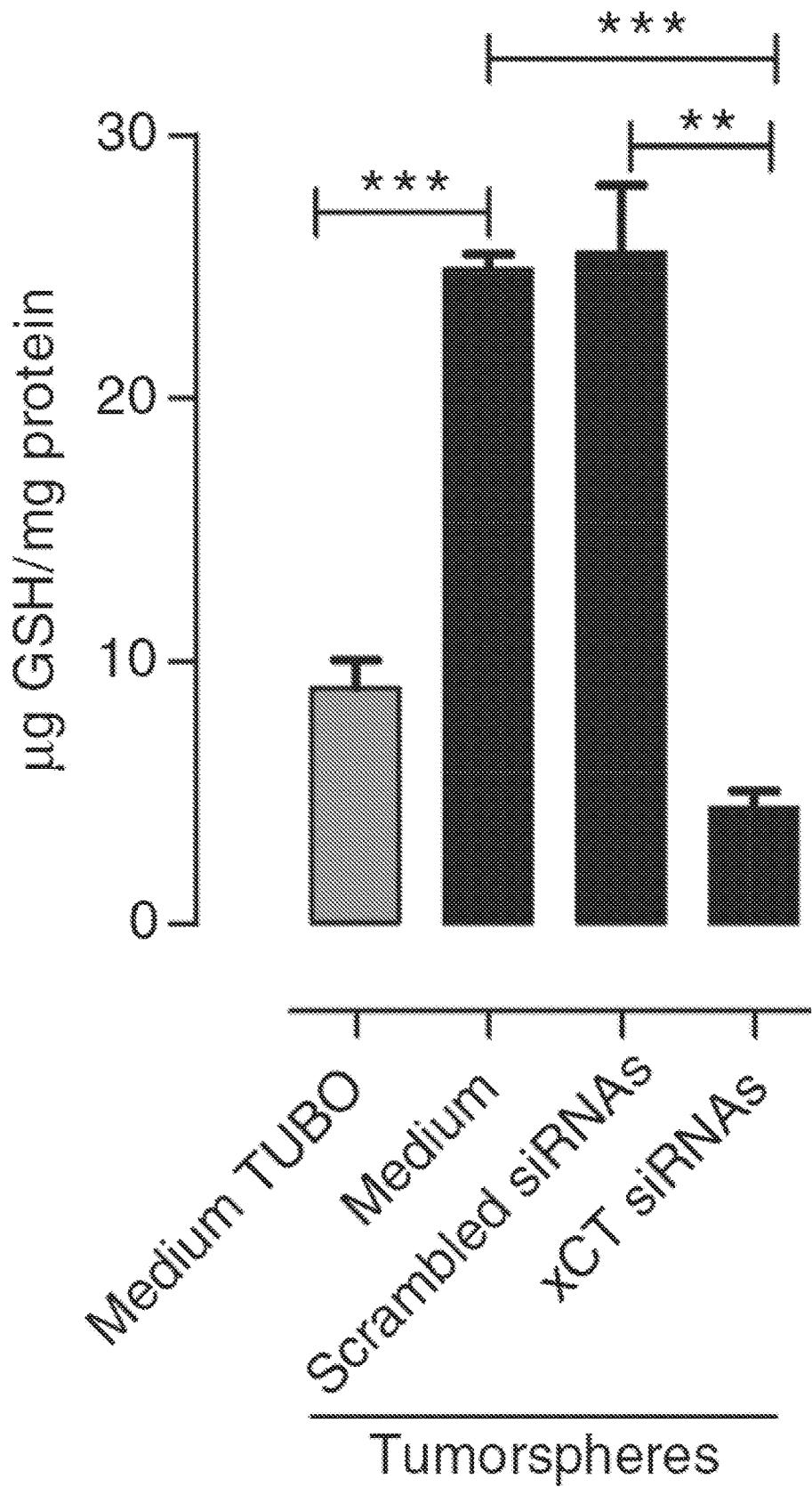
Figure 4H:
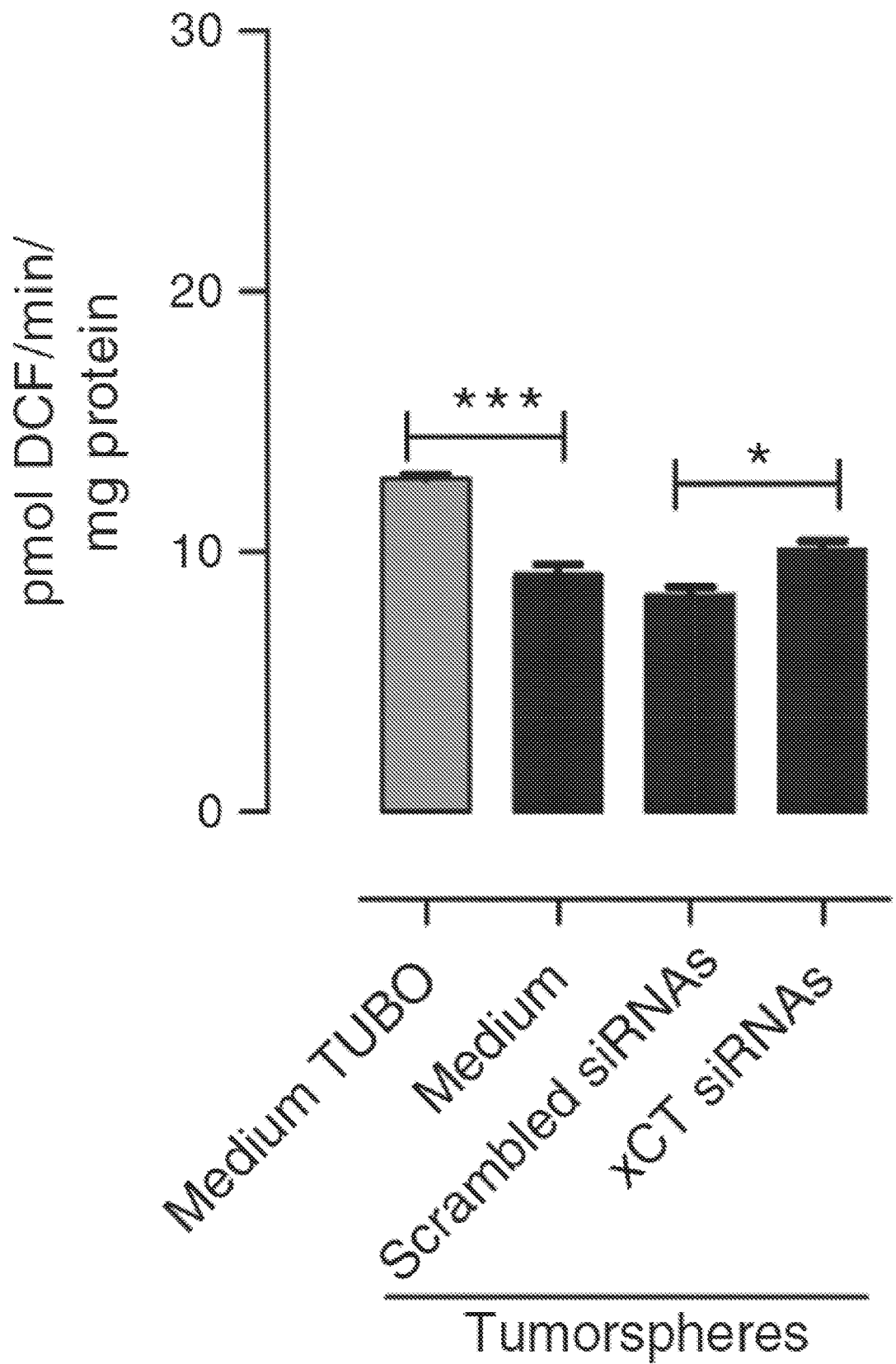

As xCT is an important determinant of redox balance, GSH and ROS levels in TUBO cells and tumorspheres were calculated. GSH amount was significantly greater in tumorspheres than in TUBO cells (FIG. 4G), whereas ROS levels were lower (FIG. 4H). xCT downregulation caused a significant decrease in GSH and an increase in ROS levels (FIGS. 4G and 4H) as compared with controls, suggesting that CSC have a higher ROS defense capability than epithelial tumor cells.

Figure 5A:
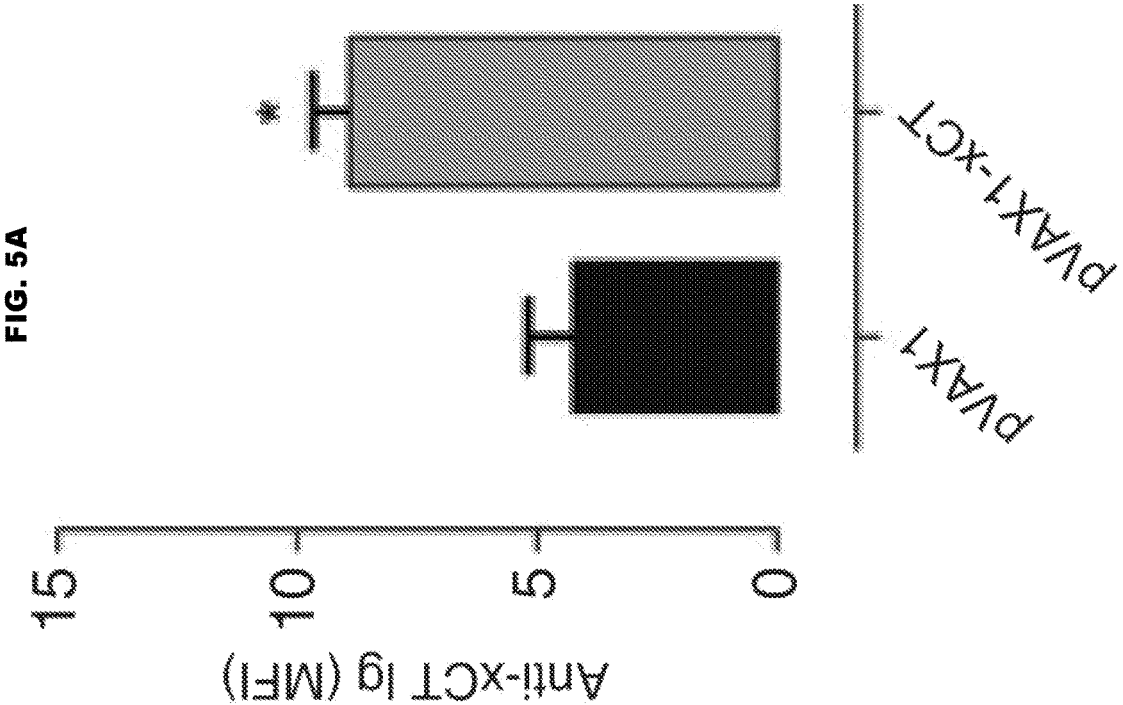
FIG. 5A-5K. Vaccine-induced antibodies target CSC and affect their self-renewal and ROS flux. A-G, TUBO-derived tumorsphere (A-C) or NIH/3T3 cell staining by antibodies present in the sera of BALB/c mice vaccinated with pVAX1 or pVAX1-xCT (E-G), analyzed by FACS. Results are reported as the mean fluorescence intensity (MFI; A and E) from 7 mice per group, the percentage of positive cells (B and F), and two representative dot plots (C and G). D and H, representative images of TUBO-tumorspheres (D) or NIH/3T3 cells stained with IgG purified from sera of mice vaccinated with pVAX1 or pVAX1-xCT (H). Scale bar, 20 µm. (I) Sphere generating ability of tumorspheres incubated for 5 days with IgG purified from the sera of mice vaccinated with pVAX1, pVAX1-xCT, or not at all. Graph shows tumorsphere number/$10^3$ plated cells. FACS analysis of CSC marker expression (J) or ROS production (K) in tumorspheres incubated for 5 days with IgG purified from the sera of vaccinated mice or not at all, reported as percentage of positive cells (D) or DCF MFI (E) from four independent experiments. *, $P<0.05$; **, $P<0.01$, Student t test.
Figure 5B:
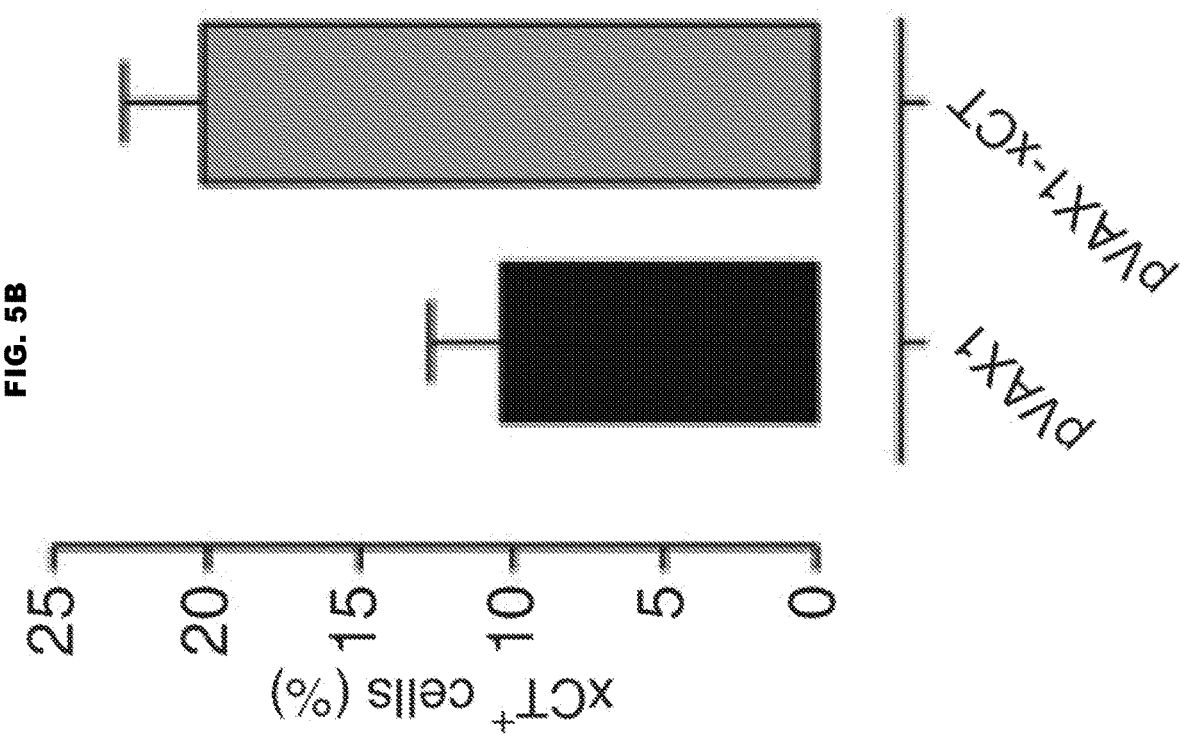
Figure 5C:
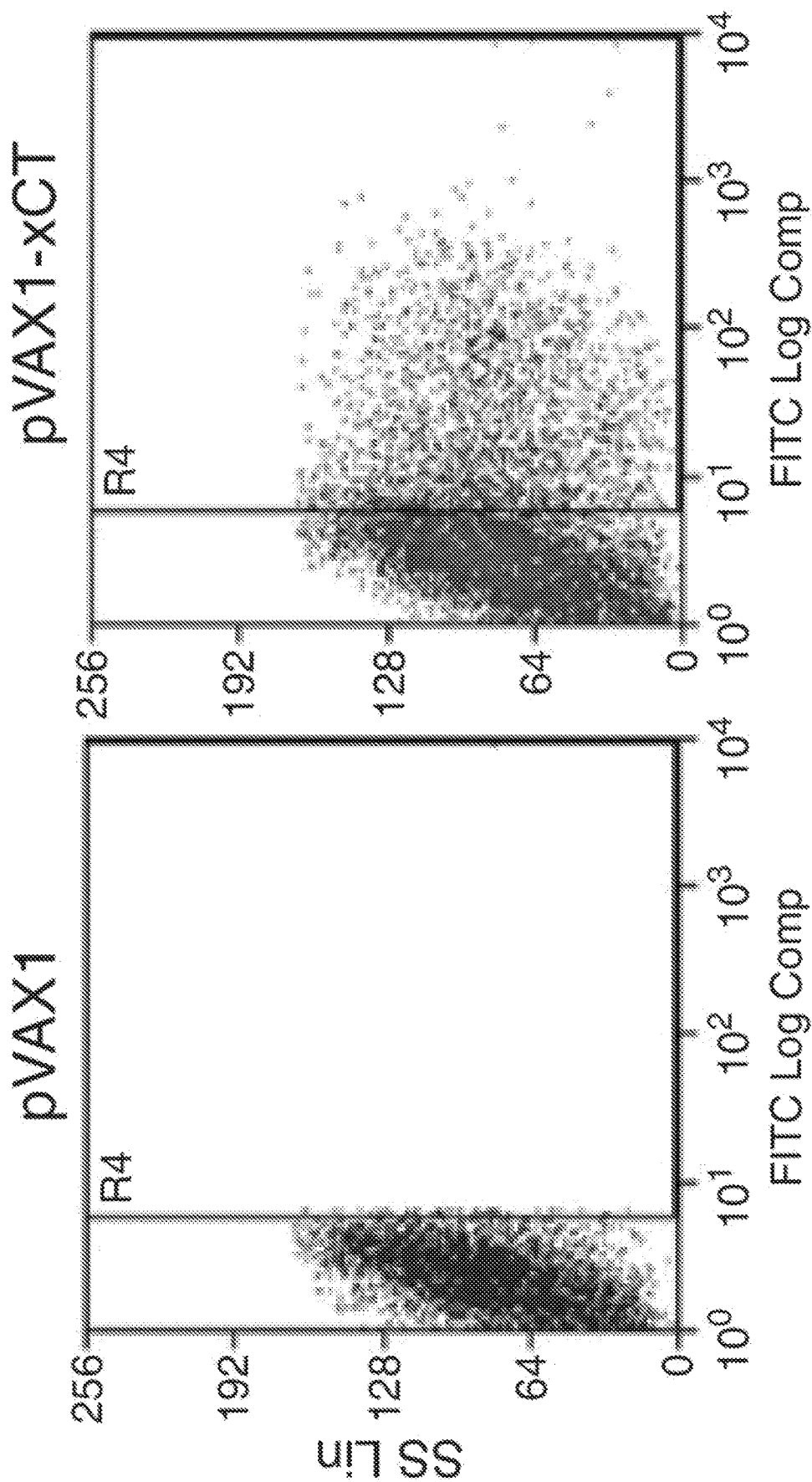
Figure 5D:
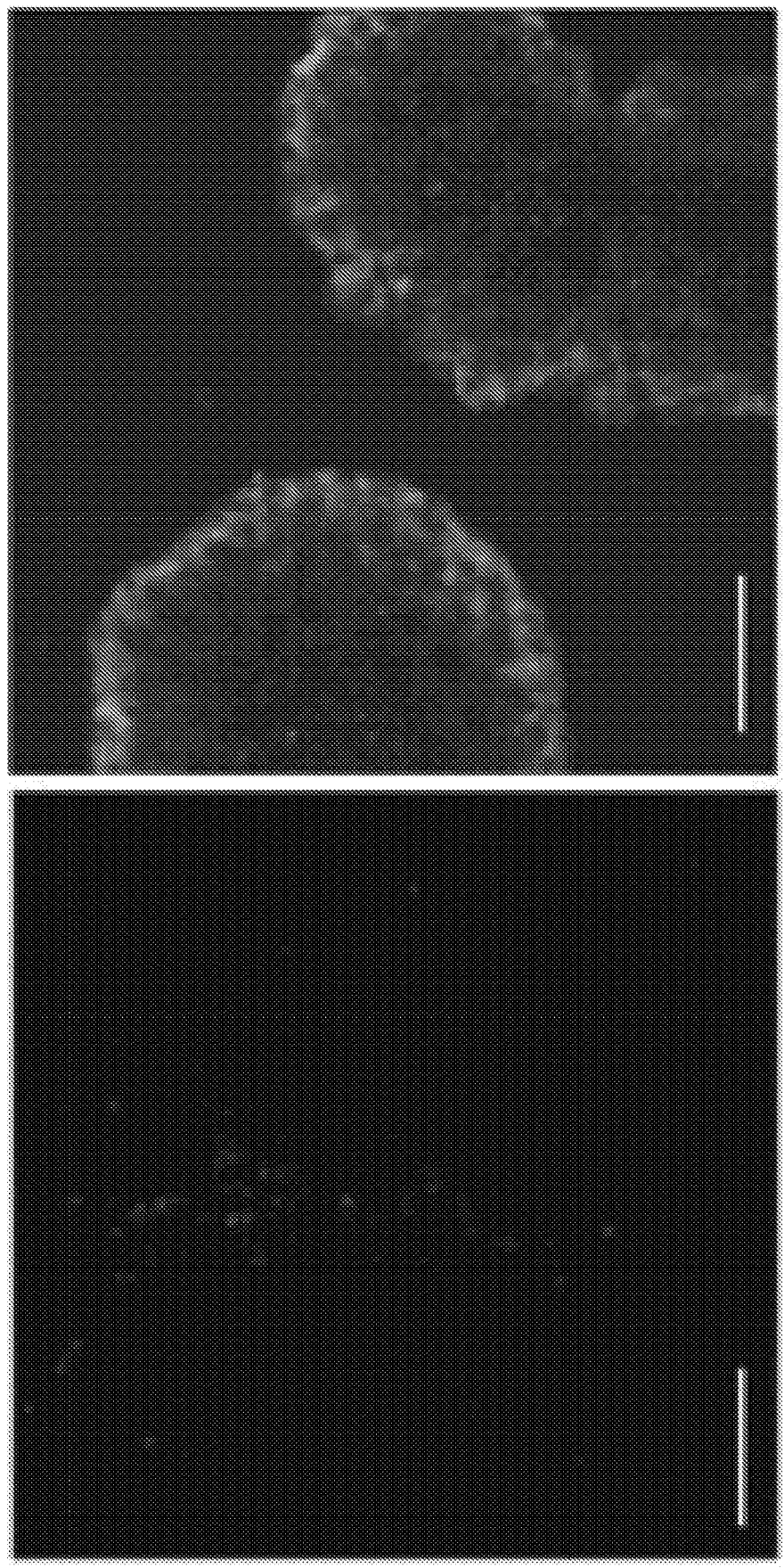
Figure 5E:
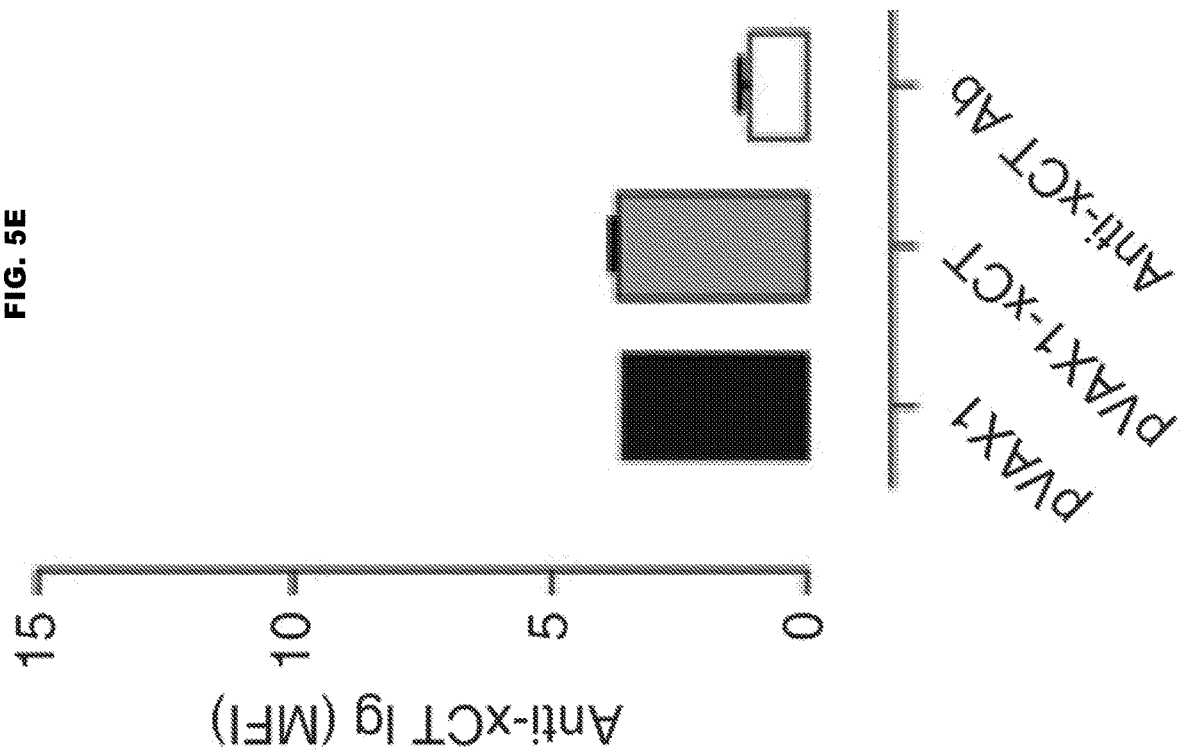
Figure 5F:
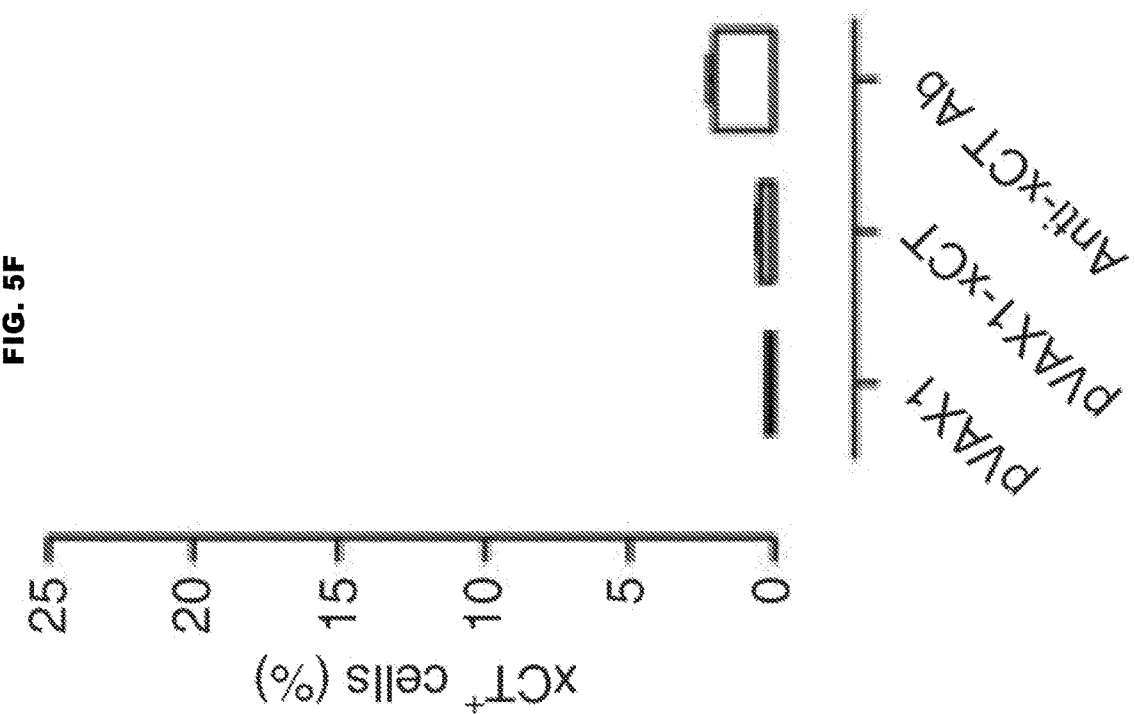
Figure 5G:
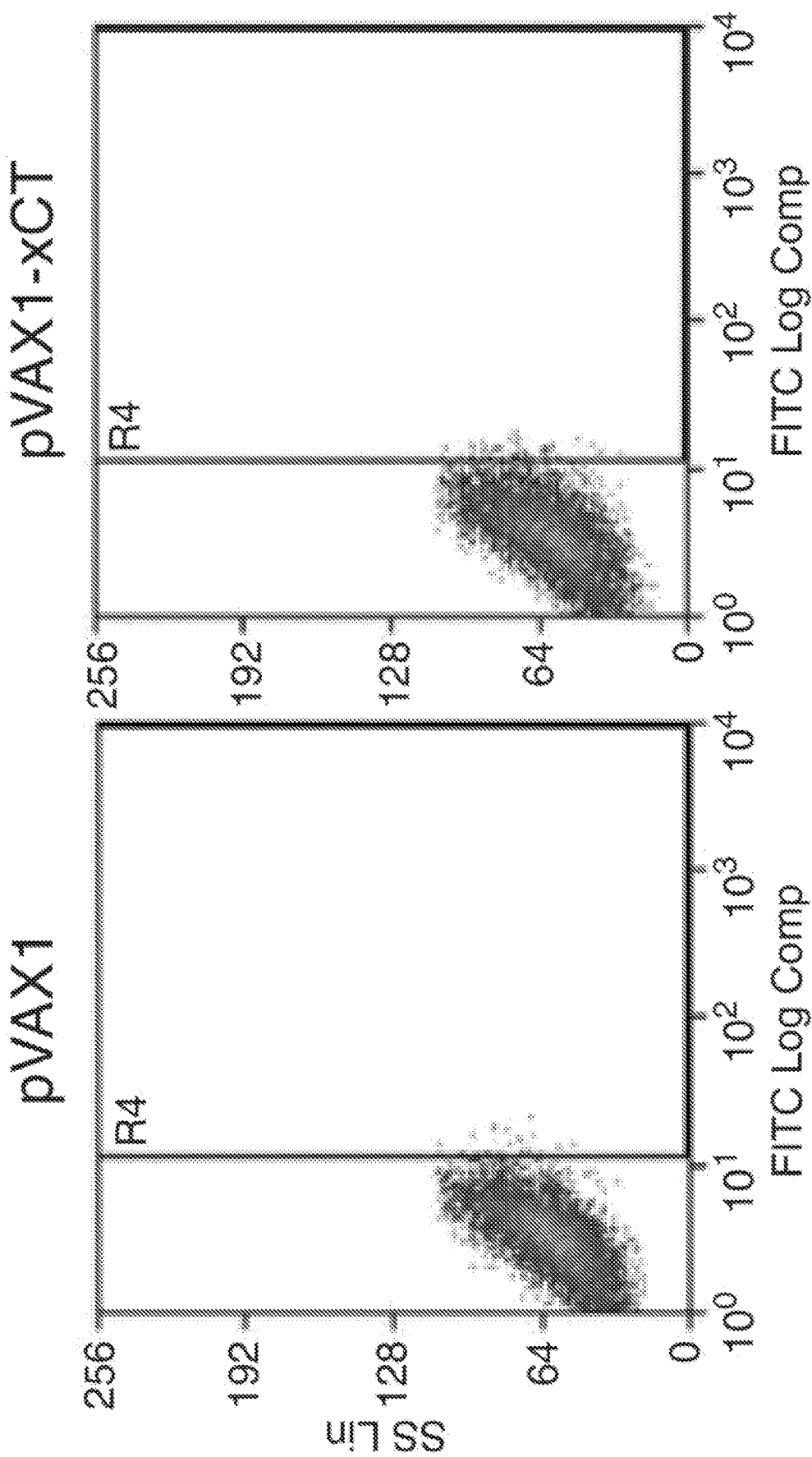
Figure 5H:
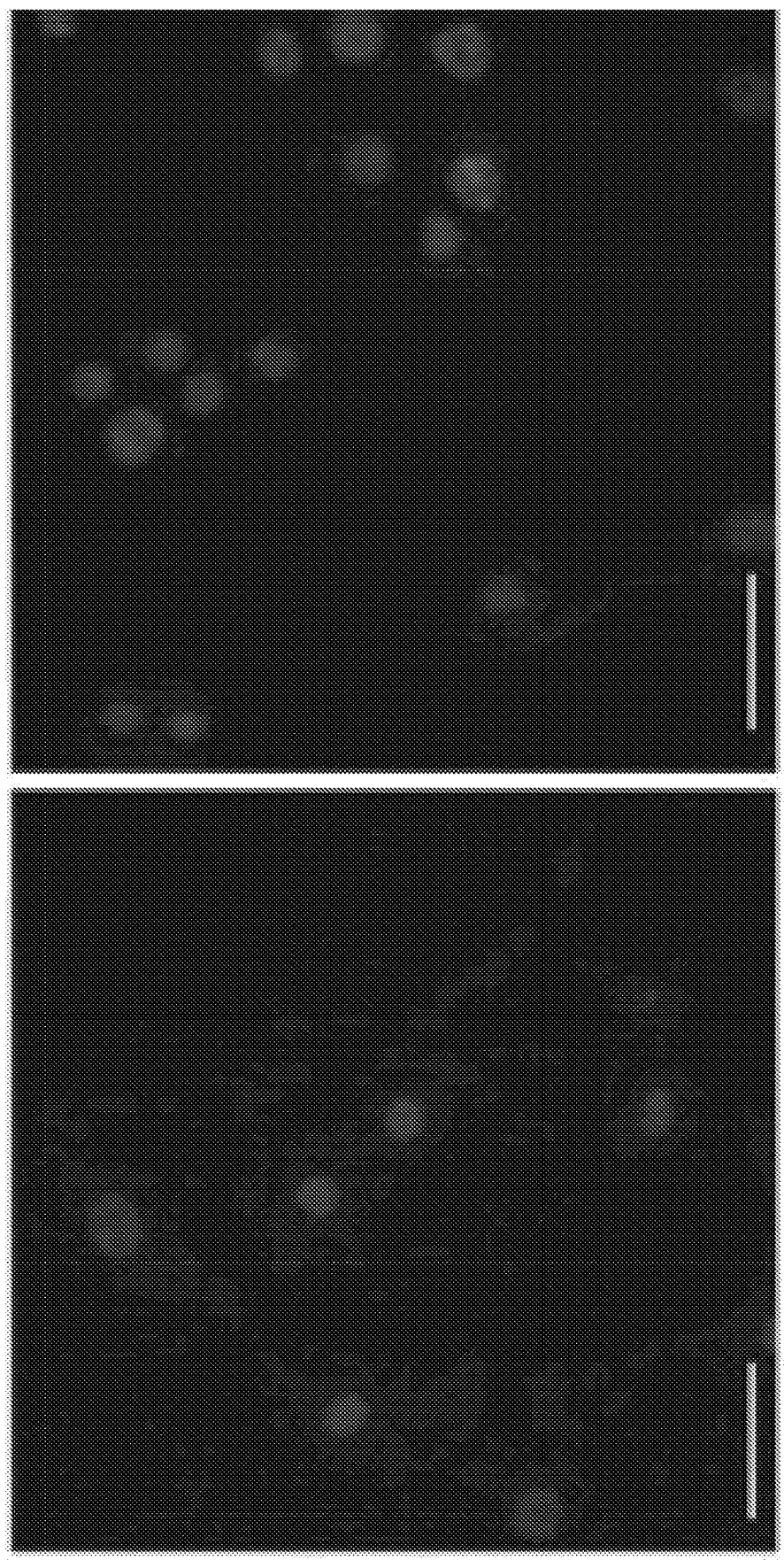
Figure 5I:
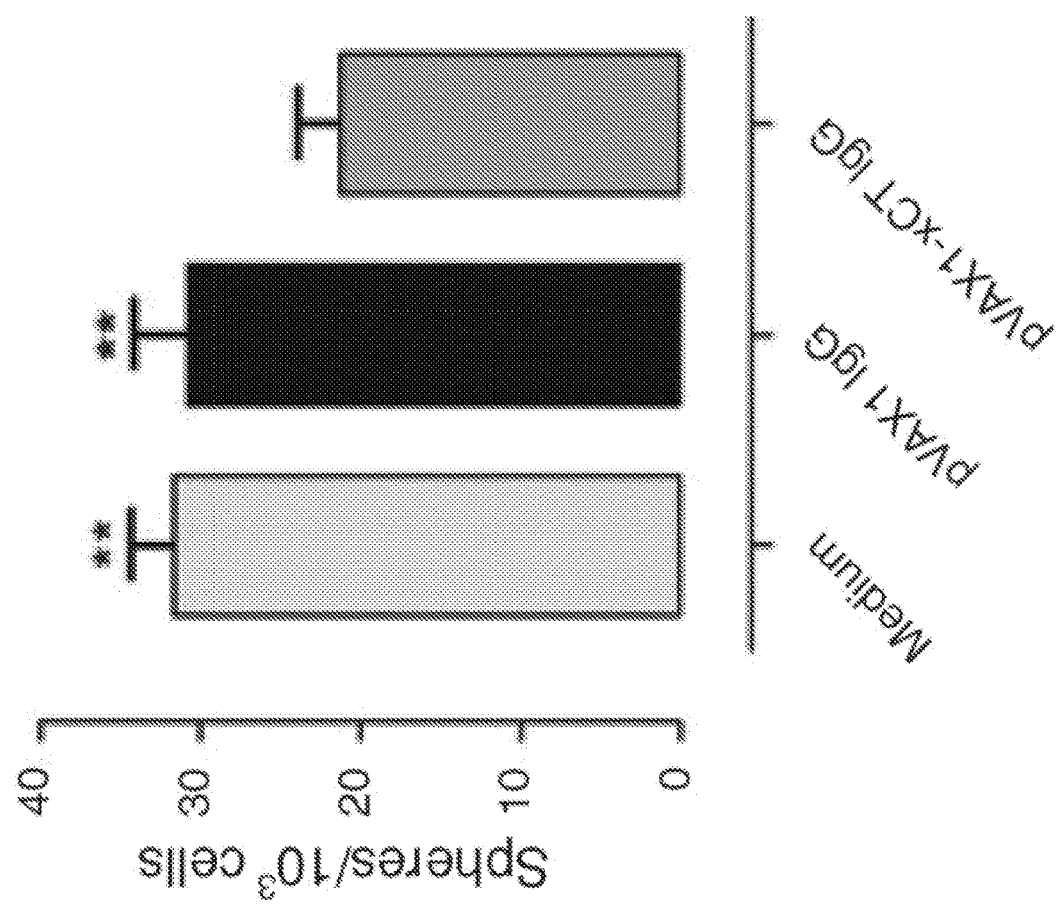
Figure 5J:
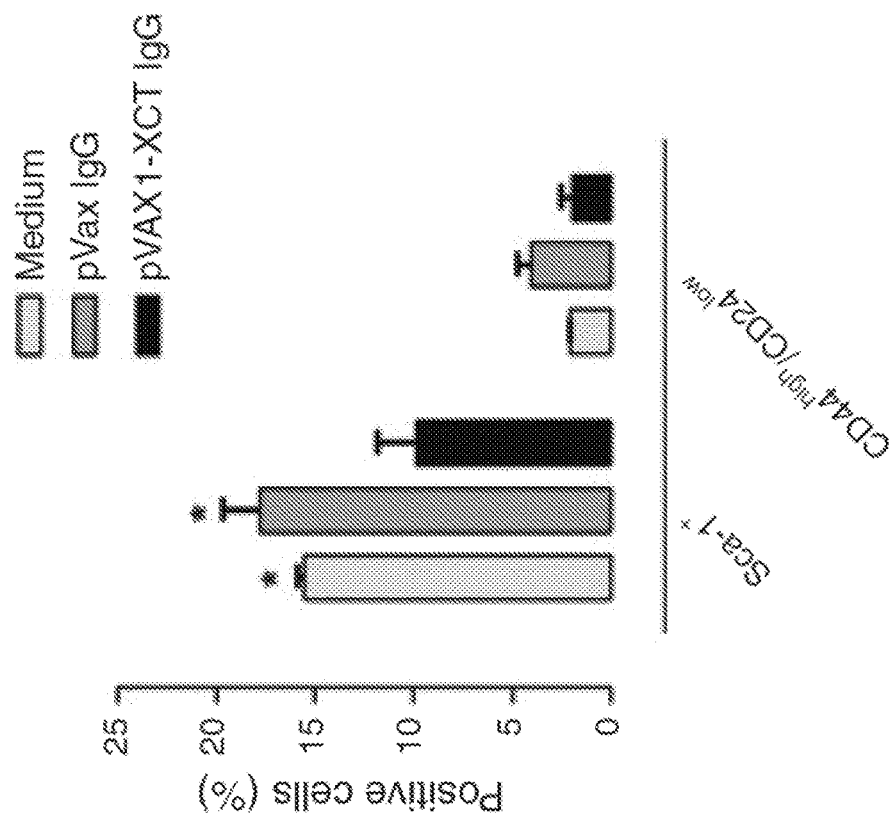
Figure 5K:
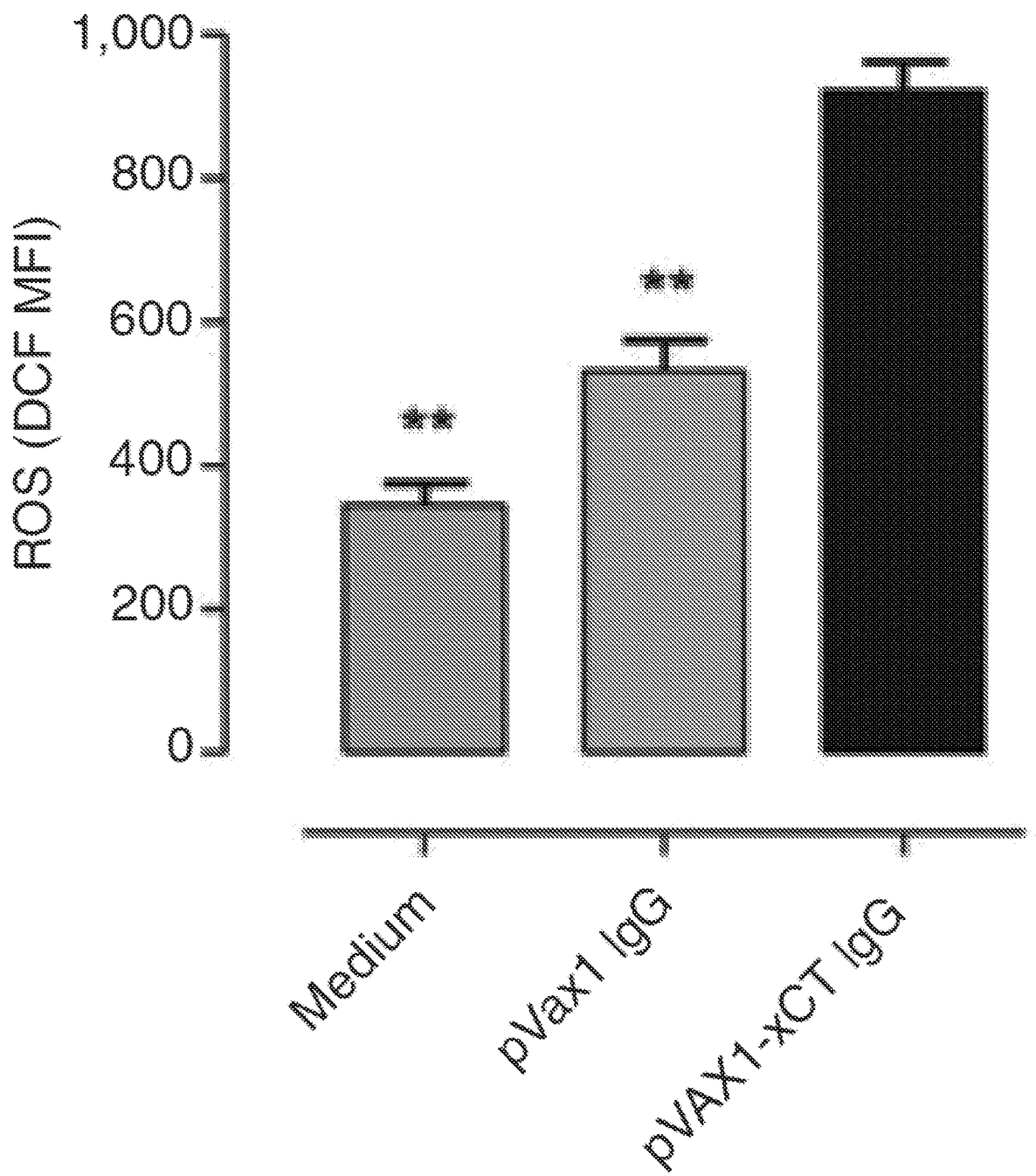

Anti-xCT vaccination induces antibodies that inhibit CSC. BALB/c mice were vaccinated with either pVAX1-xCT or pVAX1 to evaluate whether xCT is a potential target for cancer immunotherapy. No T-cell response was observed against the H-2K$^d$ dominant mouse xCT peptide. Tumorsphere-derived cells were stained with the sera of vaccinated mice to evaluate their humoral response, and specific antibody binding was analyzed by FACS. pVAX1-xCT vaccination induced the production of CSC-binding antibodies, which were not detectable in empty pVAX1-vaccinated mouse sera (FIG. 5A-5C). These results were confirmed by the ability of purified IgG, from pVAX1-xCT-vaccinated mouse sera, to stain tumorspheres (FIG. 5D). These antibodies are specific for xCT, as no binding was observed in NIH/3T3 cells negative for xCT expression (FIG. 5E-5H). Of note, TUBO cells incubated with IgG purified from pVAX1-xCT-vaccinated mice displayed reduced sphere-generation ability (FIG. 5I), a lower percentage of stem cell marker positive cells (FIG. 5J), but increased ROS content as compared with control IgG (FIG. 5K).

These results suggest that anti-xCT vaccination induces antibodies targeting xCT, thus affecting self-renewal and ROS production in CSC.

Anti-xCT Vaccination Slows In Vivo Breast Tumor Growth.

Figure 6D:
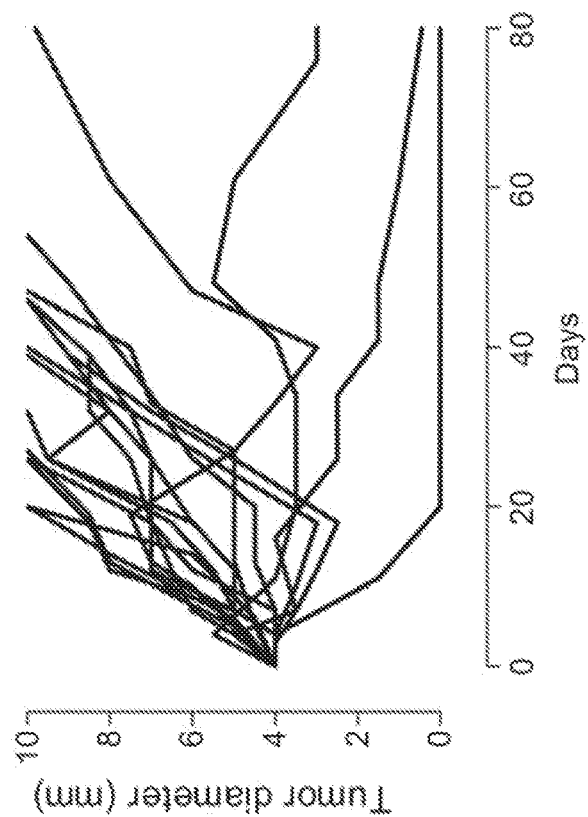
Figure 6C:
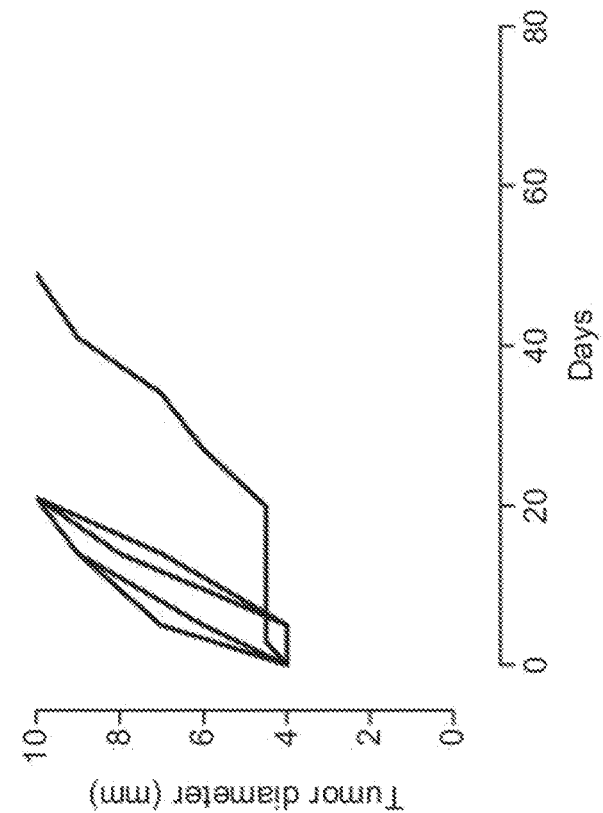
Figure 6F:
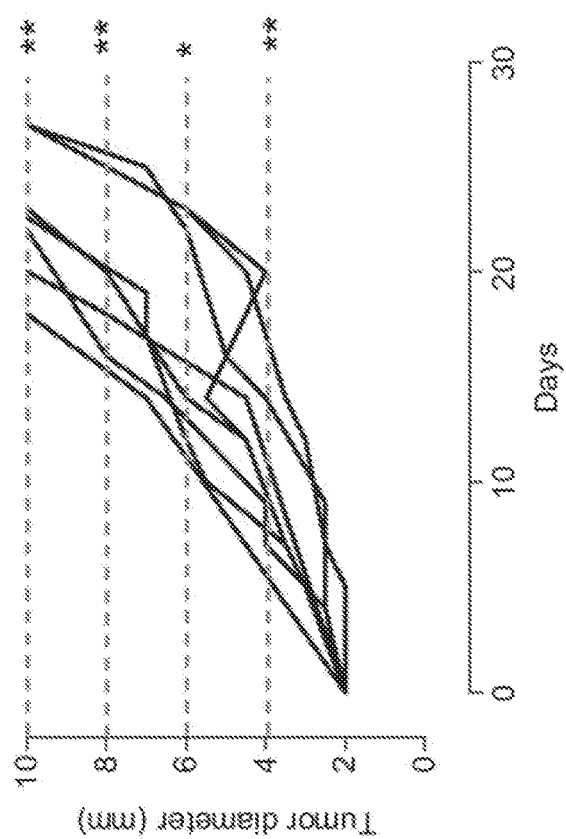
Figure 6E:
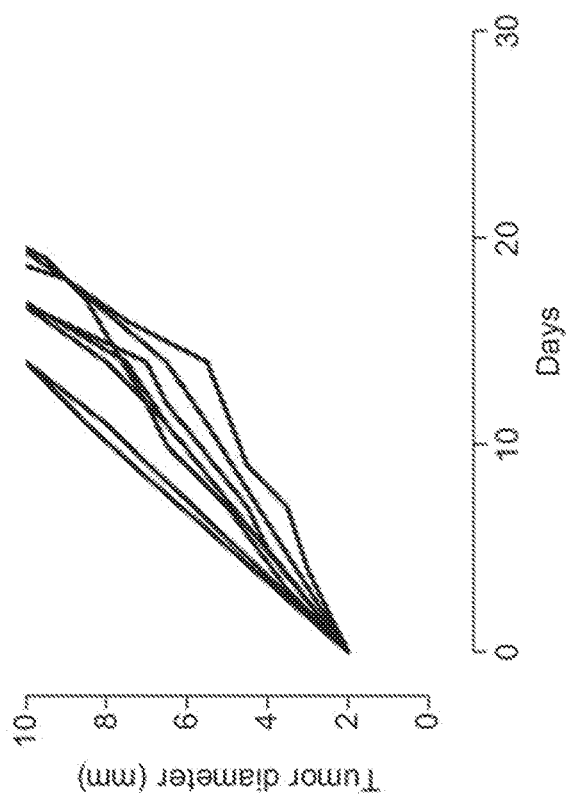
Figure 6H:
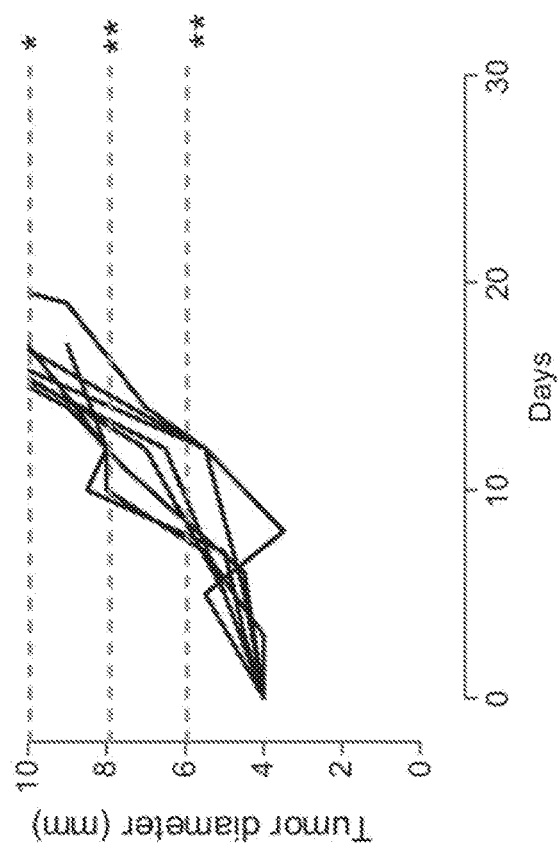
Figure 6G:
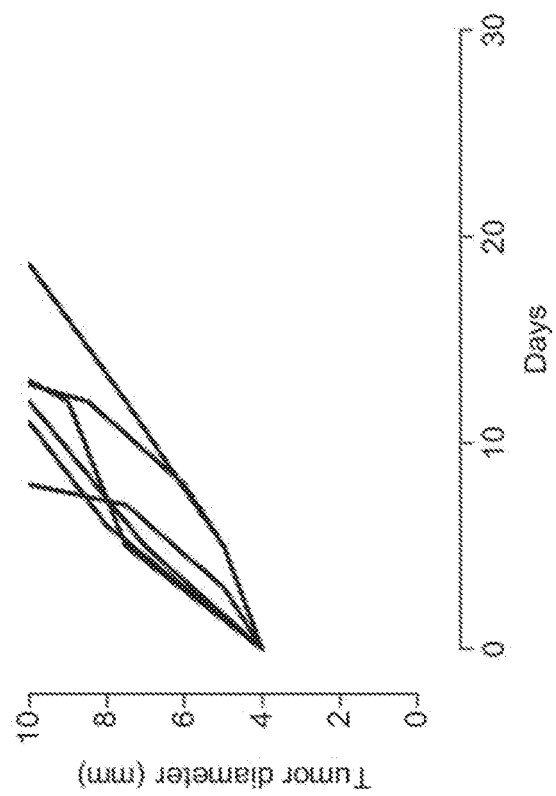

TUBO-derived tumorspheres were s.c. implanted into BALB/c mice that were vaccinated when tumors reached 2 or 4 mm mean diameter to evaluate whether xCT immune-targeting hinders breast cancer growth (FIG. 6A-6D). Tumors grew progressively in the pVAX1 group of 2 mm vaccinated mice (FIG. 6A), although tumors regressed in 23.8% of pVAX1-xCT-vaccinated mice (FIG. 6B). Tumor growth kinetics were slower in the latter group than in the pVAX1 group, as proven by the significantly shorter time required for tumors to reach 4 or 6 mm mean diameter (20.7±2.7 and 30.7±3.6 days in pVAX1-xCT-vaccinated mice vs. 12.9±2 and 20.8±2.5 days in control mice). Anti-xCT vaccination also induced tumor regression in 16% of mice that were treated when their tumors measured 4 mm mean diameter (FIG. 6D), while all tumors in the pVAX1 group reached 10 mm mean diameter in less than 60 days (FIG. 6C). The efficacy of anti-xCT vaccination was then evaluated against 2 or 4 mm mean diameter tumors obtained when 4T1 tumorsphere-derived cells were injected s.c. (FIG. 6E-6H). In 2 mm tumor-vaccinated mice, tumors grew rapidly in pVAX1 group (FIG. 6E), while tumor growth kinetics were generally slower and the time required for the tumors to reach 4, 6, 8, or 10 mm mean diameter was significantly longer in the pVAX1-xCT-vaccinated group (10.4±1.3; 15.6±1.6; 20.4±1.3; 23.4±1.2 days in pVAX1-xCT-vaccinated mice vs. 4.9±0.5; 10±1.1; 14.6±1.0; 17.4±0.8 days in control mice). Similarly, the 4 mm tumor-vaccinated group displayed slower tumor growth in pVAX1-xCT-vaccinated mice (FIGS. 6E and 6H), and the time required for the tumors to reach 6, 8, or 10 mm mean diameter was significantly longer (9.2±0.9; 13.1±0.9; 17.0±0.5 days in pVAX1-xCT-vaccinated mice vs. 5.2±0.9; 8.8±1.0; 13.0±1.6 days in control mice), indicating that xCT immunotherapy may be beneficial in various breast cancer subtypes.

Figure 6I:
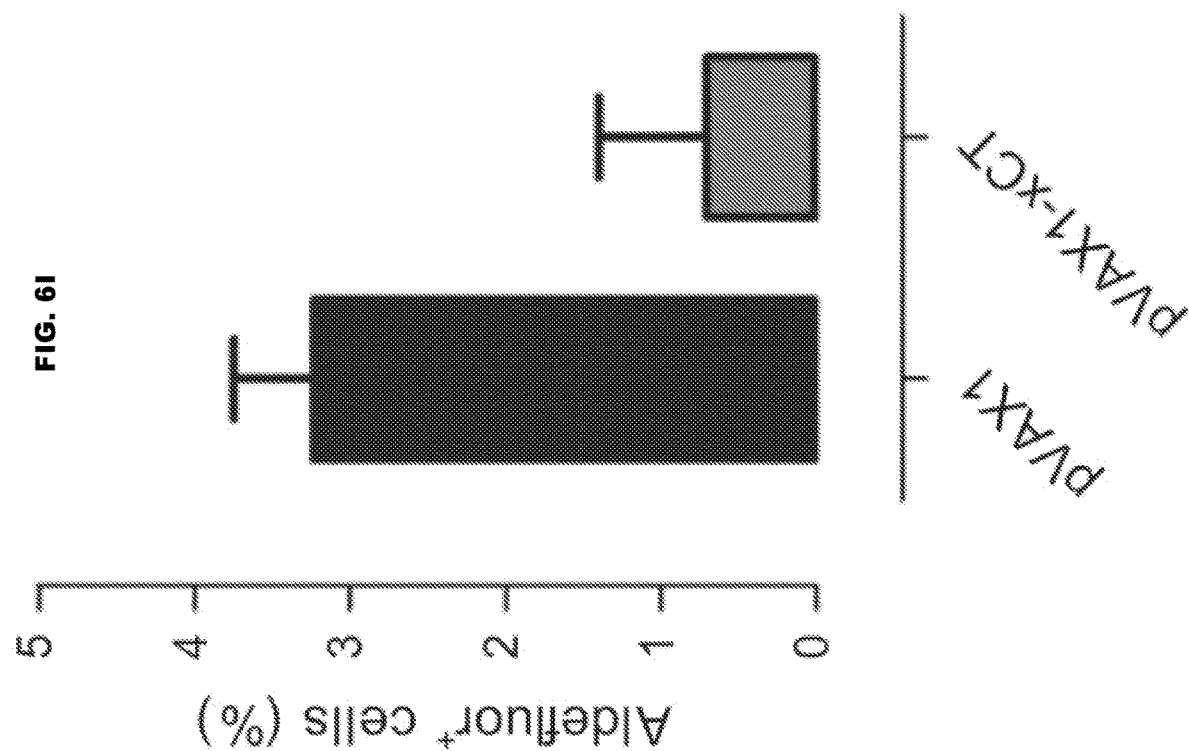
Figure 6J:
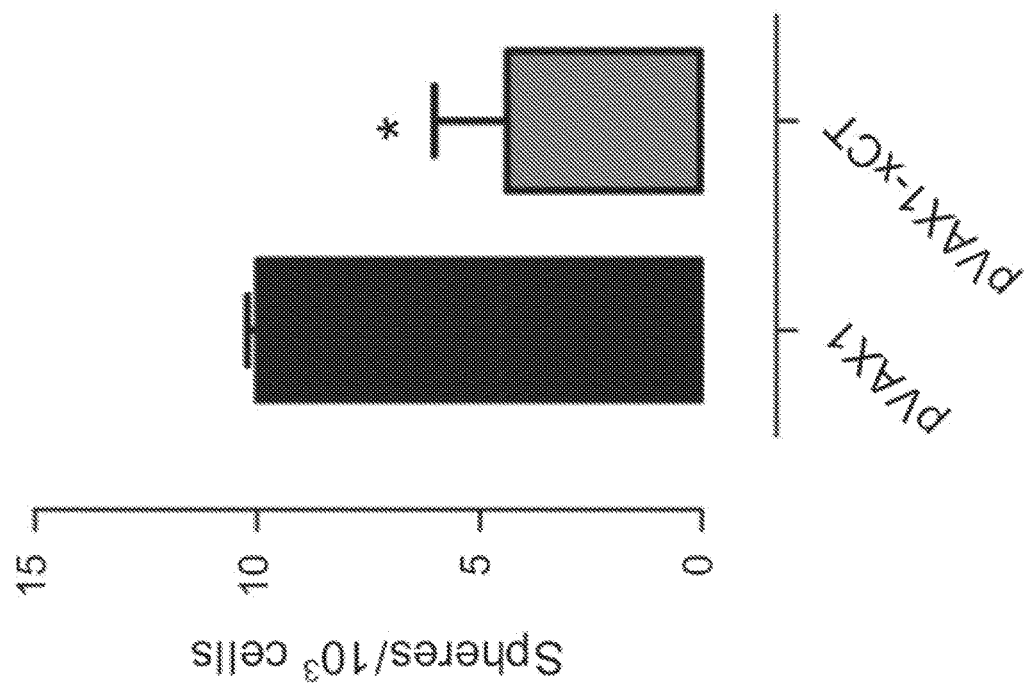

Tumor remission in vaccinated mice might be due to a reduction of CSC frequency as a consequence of the treatment, as suggested by the decrease in the percentage of Aldefluor$^+$ cells in regressing tumors from mice vaccinated with pVAX1-xCT plasmid (FIG. 6I). Moreover, the cells composing the tumor mass had a significantly decreased tumorsphere forming ability (FIG. 6J) when compared with cells derived from tumors grown in pVAX1-vaccinated mice.

Anti-xCT Vaccination Prevents Lung Metastasis Formation.

Figure 7B:
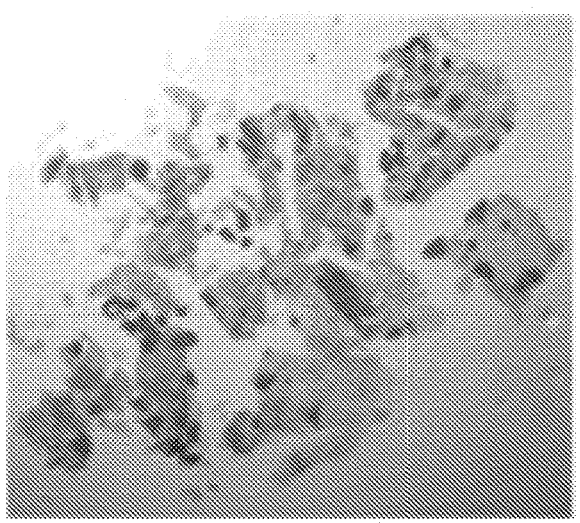
FIG. 7A-7H. Anti-xCT vaccination reduces CSC-generated lung metastasis formation. BALB/c (A, B, E, and H) and BALB-µIgKO (C and D) mice were vaccinated with either pVAX1 or pVAX1-xCT plasmids before tumorspheres injection (A, C, and E) or when mice had 2 mm mean diameter tumor (G). Number of lung metastases in mice challenged i.v. with TUBO- (A and C) or s.c. with 4T1-derived tumorspheres (E and G) and enumerated 20 days later (A and C) or when the primary tumor reached 10 mm mean diameter (E and G). B, D, F, and H, representative images of lung metastases after H&E staining. , $P<0.01$; *, $P<0.001$, Student t test.
Figure 7A:
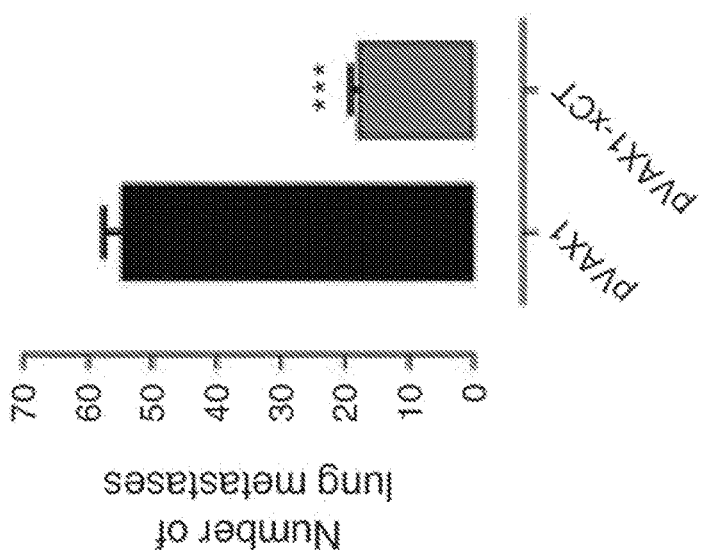
Figure 7D:
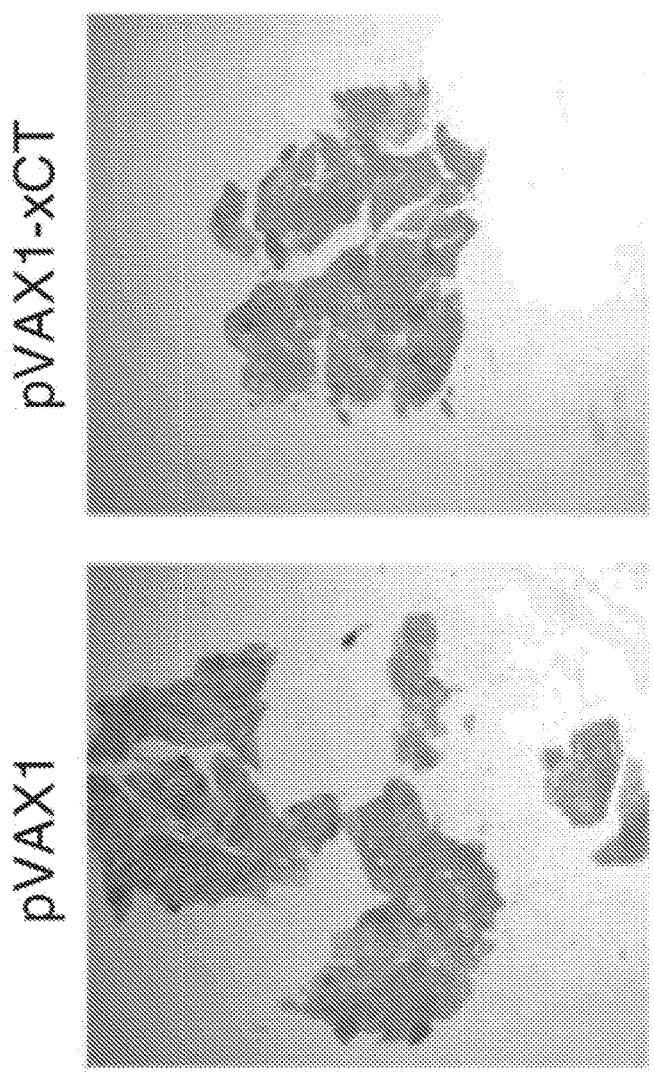
Figure 7C:
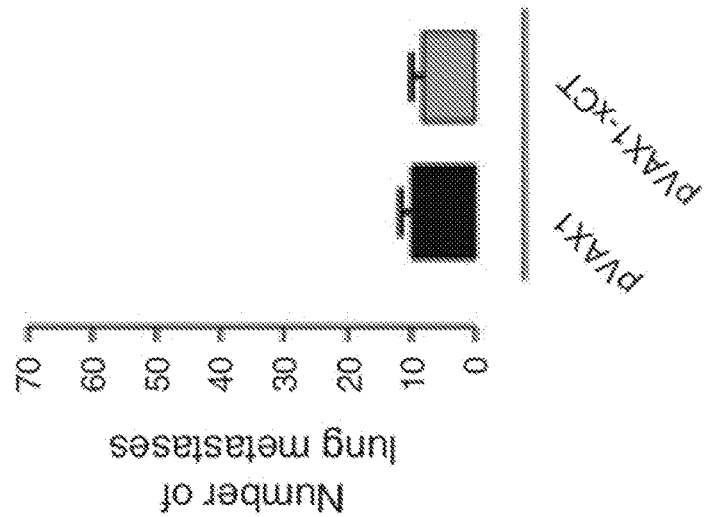

BALB/c mice were vaccinated with pVAX1 or pVAX1-xCT plasmids and i.v. injected with TUBO-derived tumorspheres to evaluate the effects of anti-xCT vaccination on lung metastasis formation. Metastasis number was significantly reduced after pVAX1-xCT vaccination, as shown in FIGS. 7A and 7B. This antimetastatic effect is dependent on the specific antibodies elicited by anti-xCT vaccination, because no effect was observed vaccinating BALB-μIg KO mice i.v. injected with TUBO-derived tumorspheres (FIGS. 7C and 7D).

Figure 7F:
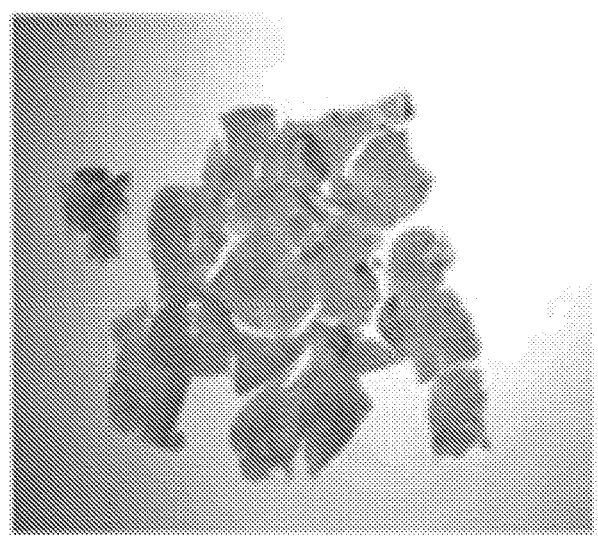
Figure 7E:
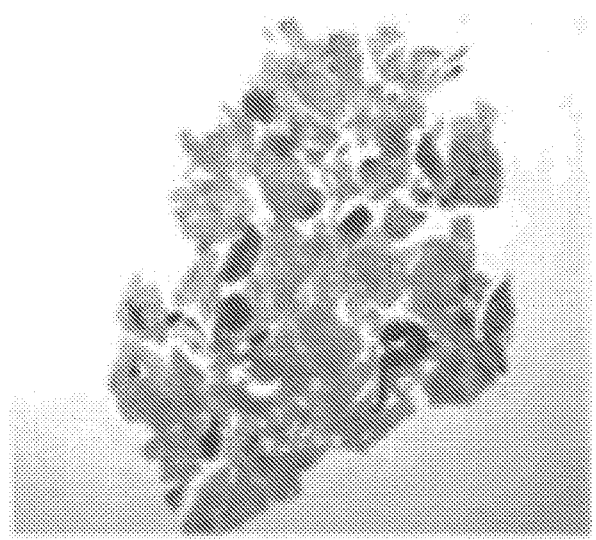
Figure 7E:
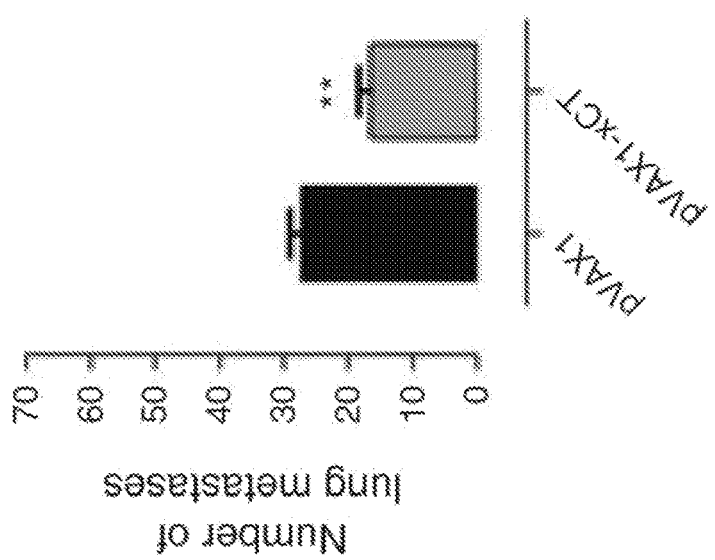
Figure 7H:
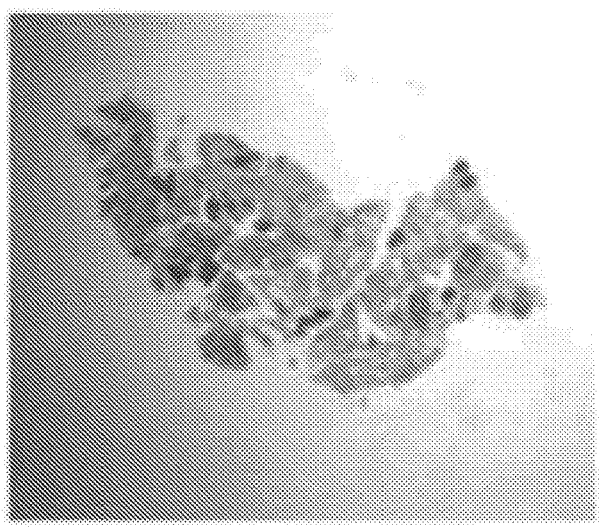
Figure 7G:
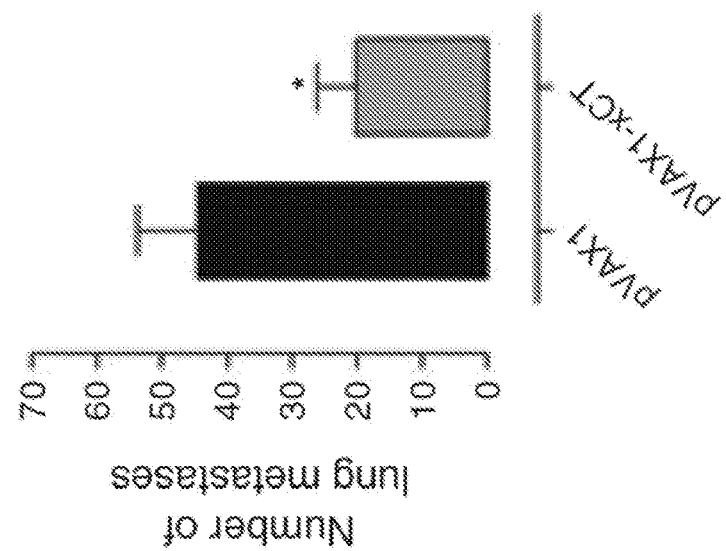

Anti-xCT vaccination was also able to reduce the number of spontaneous metastases generated from the s.c. injection of 4T1-derived tumorspheres, either when vaccination was performed before tumorsphere injection (FIGS. 7E and 7F) or when mice already had a 2-mm mean diameter tumor (FIGS. 7G and 7H).

Altogether, these findings suggest that anti-xCT vaccination interferes with CSC metastatic properties both in a preventive and therapeutic setting. This antimetastatic activity is due to CSC immunotargeting, because no effect was observed in xCT vaccinated mice injected with differentiated tumor cells or in mice vaccinated against Her3 and injected with TUBO-derived tumorspheres. In this model Her3 is not a CSC-specific antigen, because it is equally expressed on TUBO cells and tumorspheres.

Anti-xCT Vaccination Enhances the Effect of Doxorubicin.

Figure 8A:
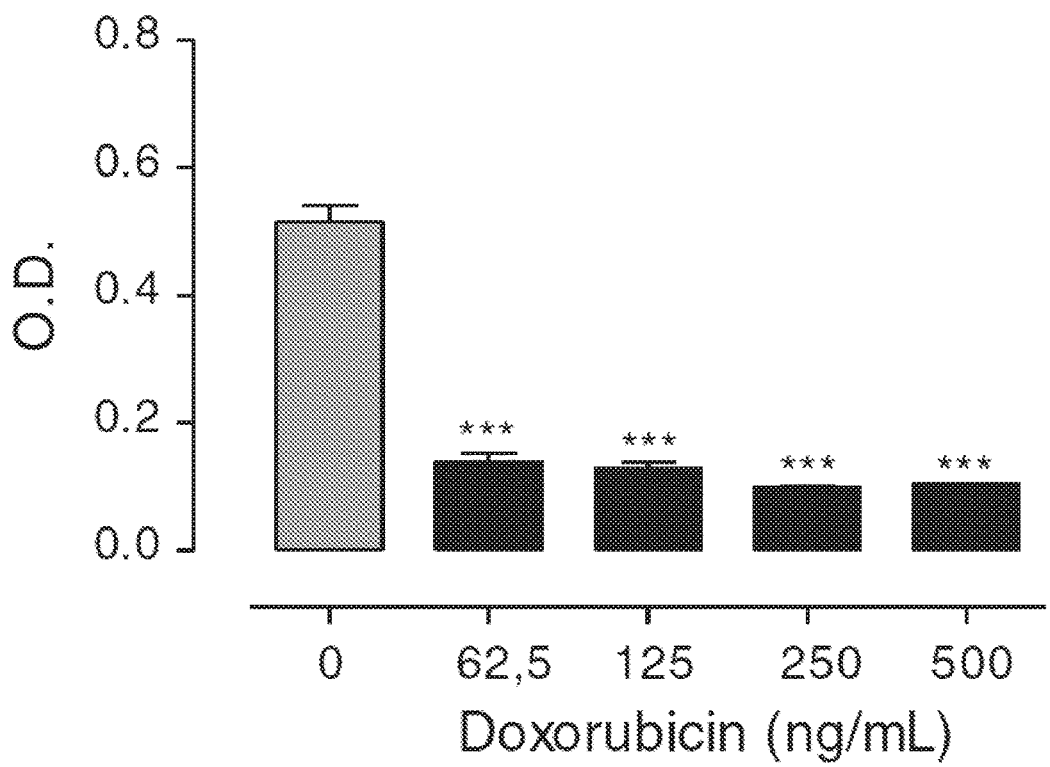
FIG. 8A-8F. Anti-xCT vaccination enhances the effect of doxorubicin in vivo. A and B, MTT assay of the cytotoxic effect exerted by incubation with scalar doses of doxorubicin in TUBO (A) and tumorspheres (B). (C) number of lung metastases in mice challenged i.v. with TUBO-derived tumorspheres and either vaccinated or not with pVAX1 and pVAX1-xCT plasmids alone or in combination with doxorubicin administration. (D-F) Tumor growth curves of BALB/c mice s.c. injected with TUBO-derived tumorspheres and treated with doxorubicin in combination with pVAX1 (E) or pVAX1-xCT (F) vaccination when their tumors reached 2 mm mean diameter. Treatments were repeated the week later. Each black line depicts the growth of a single tumor. *, $P<0.05$; , $P<0.01$; *, $P<0.001$, Student t test.
Figure 8B:
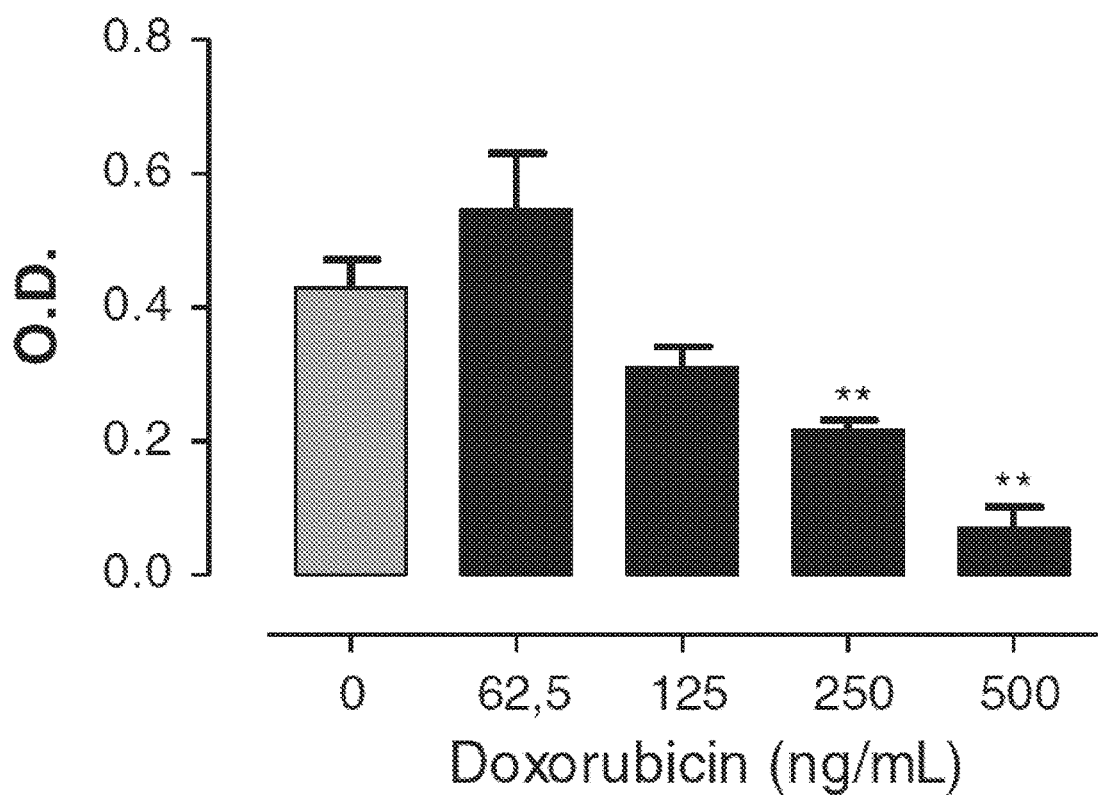
Figure 8C:
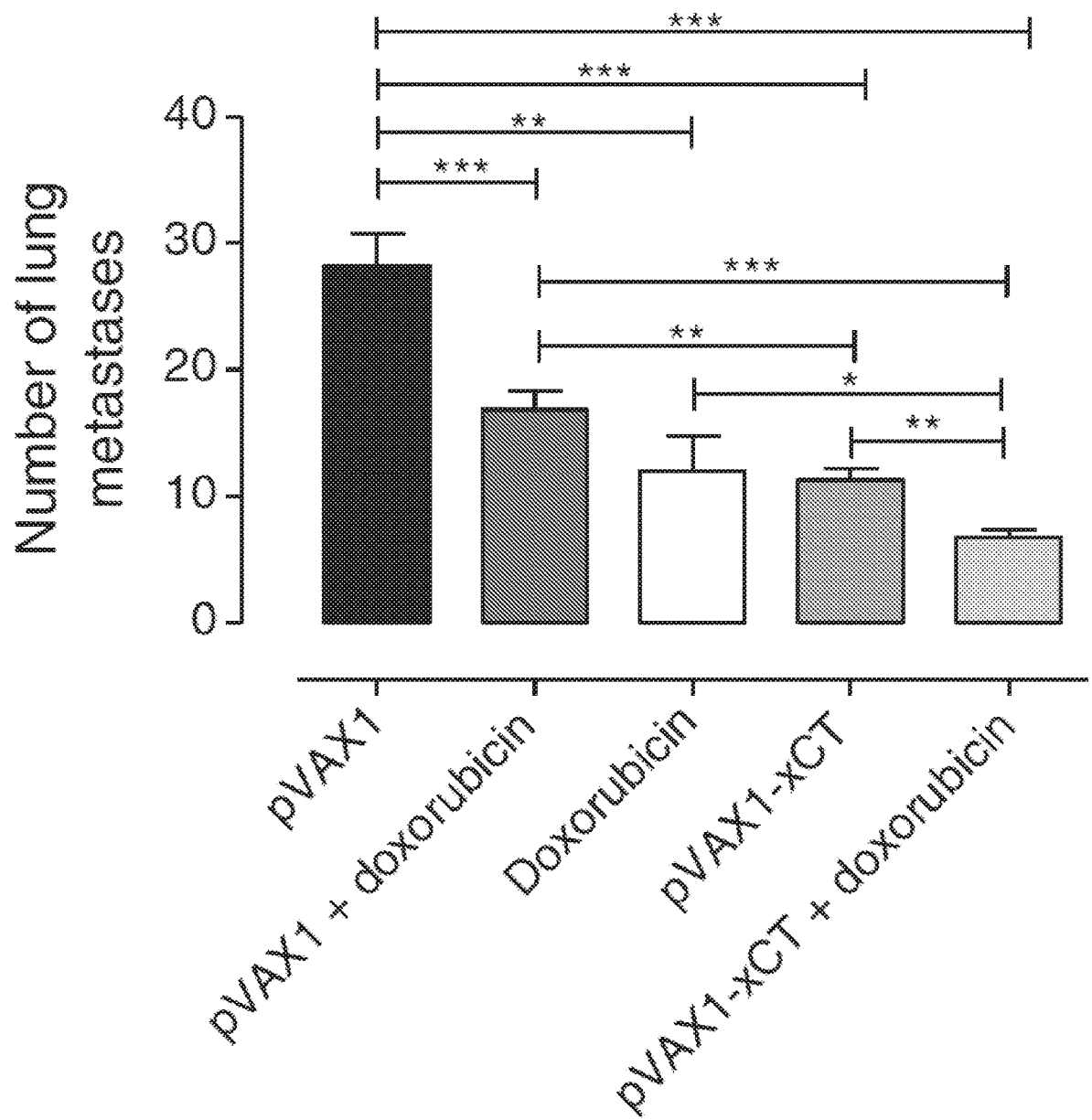

In accordance with CSC resistance to chemotherapy, TUBO cells display a higher sensitivity to doxorubicin than tumorspheres (FIGS. 8A and 8B). Because xCT is involved in maintaining the intracellular redox balance, thus counteracting the effects of ROS-generating cytotoxic drugs, it is likely that targeting xCT could increase CSC chemosensitivity. In order to explore this hypothesis in vivo, unvaccinated, pVAX1-xCT, and pVAX1-vaccinated mice were i.v. injected with TUBO-derived tumorspheres and either treated with doxorubicin or not. As shown in FIG. 8C, pVAX1-xCT determined a decrease in the number of lung metastases compared with the control and doxorubicin-treated mice and the combination of vaccination and doxorubicin significantly improved the activity of individual treatments.

Figure 8D:
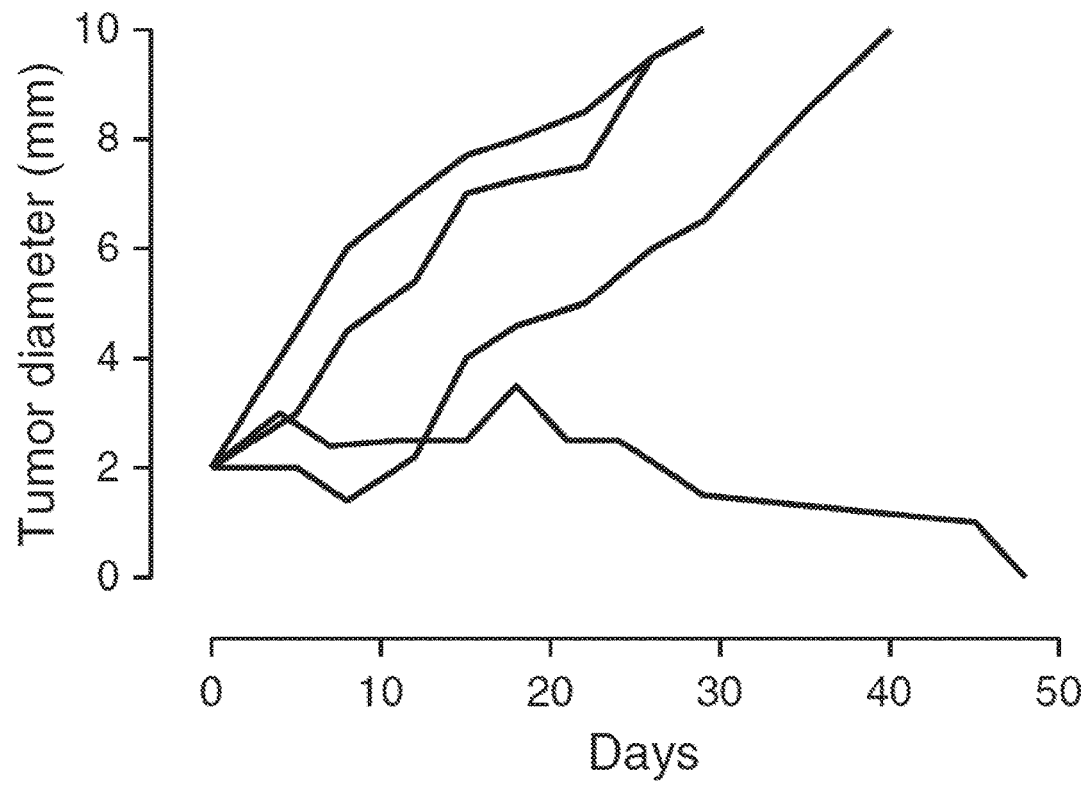
Figure 8E:
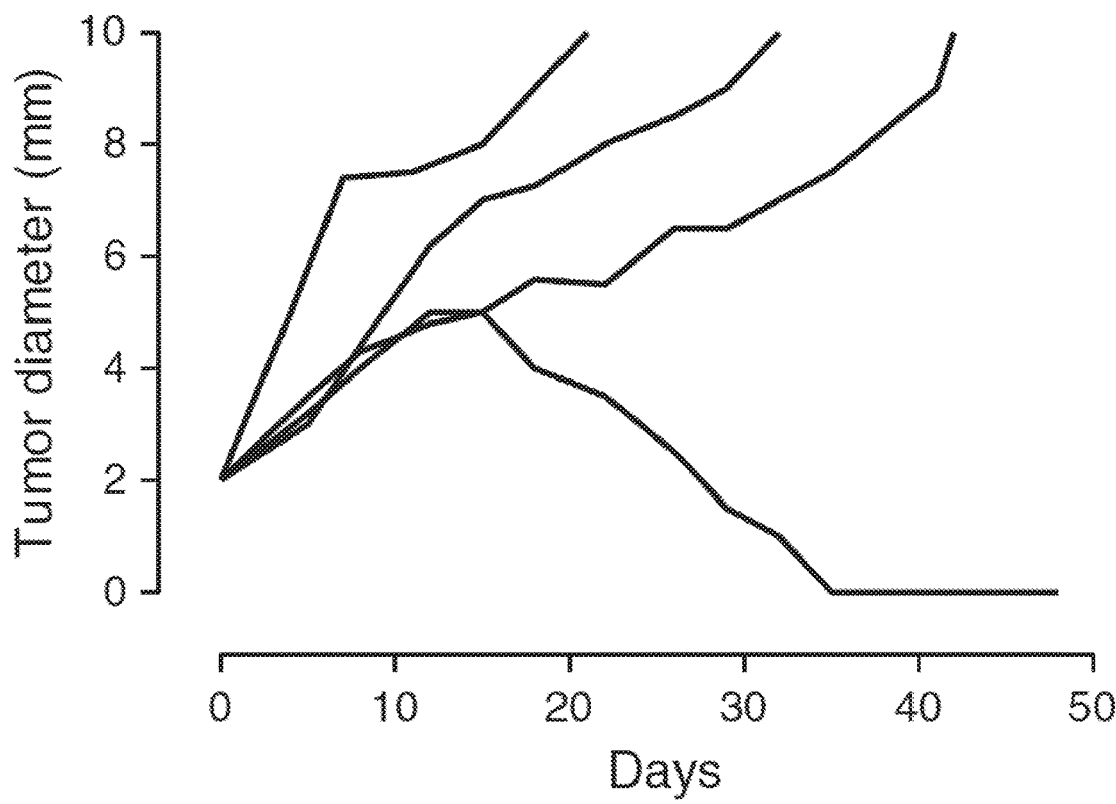
Figure 8F:
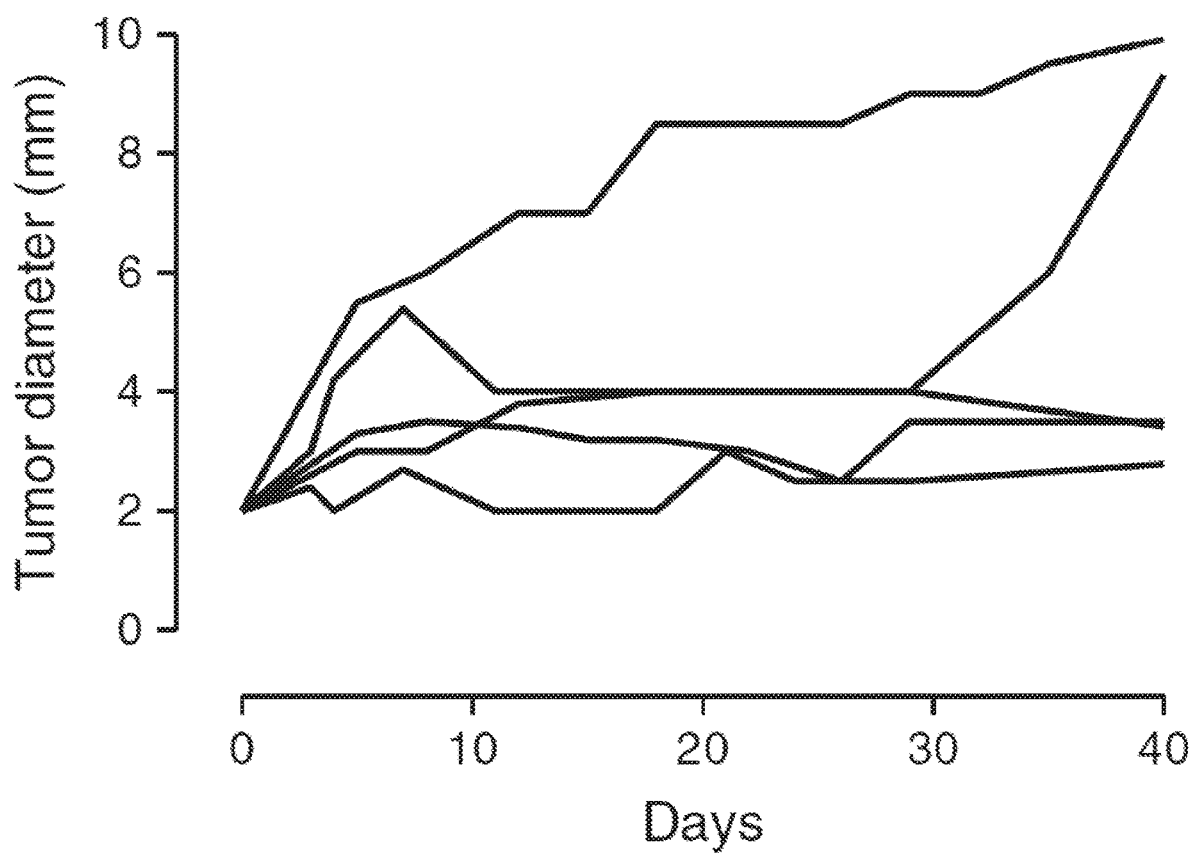

Similar results were observed in mice challenged with s.c. injection of TUBO-derived tumorspheres and subjected to vaccination and chemotherapy when tumors reached 2 mm mean diameter. The tumor regressed in 25% of mice treated with doxorubicin alone (FIG. 8D) or in combination with pVAX1 plasmid (FIG. 8E), although the combination of doxorubicin and anti-xCT vaccination stopped tumor progression in 60% of mice (FIG. 8F). All together, these data suggest that anti-xCT vaccination may well be an efficient adjuvant treatment for chemotherapy both in a preventive and in a therapeutic setting.

B. Material and Methods

Cell and tumorsphere cultures. MDA-MB-231, HCC-1806, and 4T1 cells were purchased from the ATCC (LGC Standards) and cultured. NIH/3T3 cells were cultured. Cells were passaged in for fewer than 6 months after their resuscitation. TUBO cells and tumorspheres were generated. Human cell lines were tested utilizing short tandem repeat profiling.

Facs Analysis.

Cells and tumorspheres were stained with AlexaFluor647-anti-Sca-1, PE-anti-CD44, and PE/Cy7-anti-CD24 (Biolegend), and with goat anti-xCT (Santa Cruz Biotechnology) antibodies followed by rabbit FITC-anti-goat Ig (Dako), or with Aldefluor kit (StemCell Technologies). To quantify anti-xCT antibody titers, tumorsphere-derived and NIH/3T3 cells were incubated with sera of vaccinated mice and subsequently with rabbit FITC-anti-mouse Ig (Dako). Cells were stained with 2',7'-dihydrochlorofluorescein diacetate (DHCF-DA, Sigma-Aldrich). All samples were analyzed on a CyAnADP Flow Cytometer, using the Summit 4.3 software (Beckman Coulter).

Fluorescent Microscopy.

Tumor microarrays (TMA; Biochain # T8234700-2, lot # B406087, and Biochain # T6235086-5, lot # B112136) of normal or tumor human tissues were blocked in 3% $H_2O_2$ (Sigma-Aldrich), followed by 1% BSA, and then incubated with anti-xCT or isotype-matched control antibodies (Abcam). The signal was amplified and sections were fixed in 1% formaldehyde (Sigma-Aldrich), counterstained with DAPI (Sigma-Aldrich), and mounted in Mowiol (Calbiochem). Images were acquired using a confocal microscope LSM700 and Zen software 7.0.0.285 (Zeiss). Slides were scanned on a slide scanner (Hamamatsu Nanozoomer 2.0RS) using the Calopix software. $xCT^-$ cell percentage was defined by quantifying blue (nuclei) and red (xCT) surface areas and calculated as the ratio of xCT expression (i.e., xCT stained surface/$xCT^+$ nuclei surface).

Tumorspheres were cytospun to glass slides, fixed in 4% formaldehyde and then incubated with rabbit anti-OCT4 (Abcam), rat PE-anti-Sca-1 (Santa Cruz Biotechnology), mouse APC/eFluor780-anti-Thy1.1 (eBioscience), or the matched isotype control antibodies. Cytospun tumorspheres or NIH/3T3 cultured on glass coverslips were stained with IgG purified from immunized mice sera and then with rabbit AlexaFluor488-antimouse or goat Texas red-anti-rabbit secondary antibodies (Life Technologies). Images were acquired on the ApoTome system and AxioVision Release4.8 software (Zeiss).

In Vitro Cytotoxicity.

Twenty-four hours after TUBO cells and tumorspheres seeding in 96-well plates, scalar doses of doxorubicin or sulfasalazine (SASP; Sigma-Aldrich) were added and incubated at 37° C. for 72 hours. Cytotoxicity was evaluated with MTT using the Cell Proliferation Kit I (Roche Diagnostics).

RNA Interference.

xCT downregulation in tumorspheres was performed using a pool of specific siRNAs, or scrambled siRNAs (Invitrogen Corp.).

SASP Effects on Tumorsphere Formation.

Dissociated tumorspheres were cultured with scalar doses of SASP or its diluent DMSO (Sigma-Aldrich), and the total number of tumorspheres/well was counted 5 days later.

Measurement of ROS and GSH.

ROS amount was analyzed as 2',7'-dichlorofluorescin (DCF) formation in cells incubated with 5 µtmol/L DHCF-DA for 20 minutes at 37° C. using the Luminescence Spectrometer LS 55 (Perkin-Elmer), quantified using a DCF standard curve, and expressed as pmol DCF formed/min/mg protein. GSH content was assessed by determining nonprotein sulphydryl content and calculated using a GSH standard curve. Results are expressed as mg GSH/mg of cellular proteins.

Plasmids.

The cDNA sequence for mouse xCT (NM_011990.2), in the pDream2.1 plasmid (GenScript), was cloned in a pVAX1 (Invitrogen) plasmid (pVAX1-xCT), sequenced (BMR Genomics), and produced with EndoFree Plasmid Giga Kits (Qiagen Inc.).

Immune Sera Effect on Tumorsphere Formation.

Serum IgG from vaccinated mice were purified using the Melon Gel Purification Kit (Thermo Scientific) and incubated with tumorsphere-derived cells. After 5 days, spheres were counted and analyzed for CSC markers expression and ROS production by FACS.

In Vivo Treatments.

Female 6- to 8-week-old wild-type (Charles River Laboratories) and Ig µ-chain gene knocked out (BALB-µIgKO) BALB/c mice were maintained at the Molecular Biotechnology Center, University of Torin, and treated in accordance with the University Ethical Committee and European guidelines under Directive 2010/63. Vaccination, performed either before or after tumor challenge, consisted of two intramuscular electroporations at 2 weeks interval, of pVAX1 or pVAX1-xCT plasmids.

Primary s.c. tumors were induced by injecting $1 \times 10^4$ TUBO or 4T1 tumorsphere-derived cells. Some tumors were explanted and tumorspheres. Lung metastases were induced either by injecting i.v. $5 \times 10^4$ TUBO tumorsphere-derived cells or by injecting s.c. $1 \times 10^4$ 4T1 tumorsphere-derived cells. In the latter case, lungs were removed when s.c. tumors reached 10 mm mean diameter. Micrometastases were counted on a Nikon SMZ1000 stereomicroscope (Mager Scientific).

Doxorubicin treatment consisted of the i.v. administration of a total dose of 10 mg/Kg either in a single injection or in two administration at a week interval.

Statistical Analysis.

Differences in latency, sphere formation, protein expression, GSH, and ROS levels and metastasis number were evaluated using a Student t test. Data are shown as the mean±SEM unless otherwise stated. Values of P<0.05 were considered statistically significant.

The invention claimed is:

1. An RNA-bacteriophage virus-like particle (VLP) comprising a single chain dimeric coat protein having an xCT peptide insertion, wherein the xCT peptide has an amino acid sequence of KGQTQNFKDAFSGRDSSITRLP (SEQ. ID NO:9), GDLDSLLN (SEQ. ID NO:11) and/or LYSDPFST (SEQ. ID NO:12).

2. An immunogenic composition comprising an RNA bacteriophage VLP displaying an xCT peptide, wherein the xCT peptide has an amino acid sequence of KGQTQNFKDAFSGRDSSITRLP (SEQ. ID NO:9), GDLDSLLN (SEQ. ID NO:11), and/or LYSDPFST (SEQ. ID NO:12).

3. A method of inducing an immune response in a subject comprising administering a composition of claim 1.

4. The method of claim 3, wherein the subject is a human.

5. The method of claim 3, wherein the subject has cancer.

6. The method of claim 5, wherein the cancer expresses xCT.

7. The method of claim 5, wherein the cancer is breast cancer.

8. A vaccine vector comprising a nucleic acid encoding the RNA-bacteriophage virus-like particle (VLP) of claim 1.

9. A method of treating cancer comprising administering the vaccine vector or claim 8.

10. The method of claim 9, wherein the subject is a human.

11. The method of claim 9, wherein the subject has cancer.

12. The method of claim 11, wherein the cancer expresses xCT.

13. The method of claim 11, wherein the cancer is breast cancer.

* * * * *

SEQUENCE LISTING

<160> NUMBER OF SEQ ID NOS: 12

<210> SEQ ID NO 1
<211> LENGTH: 501
<212> TYPE: PRT
<213> ORGANISM: Homo sapiens

<400> SEQUENCE: 1

```
Met Val Arg Lys Pro Val Val Ser Thr Ile Ser Lys Gly Gly Tyr Leu
1               5                   10                  15

Gln Gly Asn Val Asn Gly Arg Leu Pro Ser Leu Gly Asn Lys Glu Pro
                20                  25                  30

Pro Gly Gln Glu Lys Val Gln Leu Lys Arg Lys Val Thr Leu Leu Arg
            35                  40                  45

Gly Val Ser Ile Ile Ile Gly Thr Ile Ile Gly Ala Gly Ile Phe Ile
        50                  55                  60

Ser Pro Lys Gly Val Leu Gln Asn Thr Gly Ser Val Gly Met Ser Leu
65                  70                  75                  80

Thr Ile Trp Thr Val Cys Gly Val Leu Ser Leu Phe Gly Ala Leu Ser
                85                  90                  95

Tyr Ala Glu Leu Gly Thr Thr Ile Lys Lys Ser Gly Gly His Tyr Thr
                100                 105                 110

Tyr Ile Leu Glu Val Phe Gly Pro Leu Pro Ala Phe Val Arg Val Trp
            115                 120                 125

Val Glu Leu Leu Ile Ile Arg Pro Ala Ala Thr Ala Val Ile Ser Leu
        130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Ile Thr Ala Val Gly Ile Thr Val Val
                165                 170                 175

Met Val Leu Asn Ser Met Ser Val Ser Trp Ser Ala Arg Ile Gln Ile
                180                 185                 190

Phe Leu Thr Phe Cys Lys Leu Thr Ala Ile Leu Ile Ile Ile Val Pro
            195                 200                 205

Gly Val Met Gln Leu Ile Lys Gly Gln Thr Gln Asn Phe Lys Asp Ala
        210                 215                 220

Phe Ser Gly Arg Asp Ser Ser Ile Thr Arg Leu Pro Leu Ala Phe Tyr
225                 230                 235                 240

Tyr Gly Met Tyr Ala Tyr Ala Gly Trp Phe Tyr Leu Asn Phe Val Thr
                245                 250                 255

Glu Glu Val Glu Asn Pro Glu Lys Thr Ile Pro Leu Ala Ile Cys Ile
                260                 265                 270

Ser Met Ala Ile Val Thr Ile Gly Tyr Val Leu Thr Asn Val Ala Tyr
            275                 280                 285

Phe Thr Thr Ile Asn Ala Glu Glu Leu Leu Leu Ser Asn Ala Val Ala
        290                 295                 300

Val Thr Phe Ser Glu Arg Leu Leu Gly Asn Phe Ser Leu Ala Val Pro
305                 310                 315                 320

Ile Phe Val Ala Leu Ser Cys Phe Gly Ser Met Asn Gly Gly Val Phe
                325                 330                 335
```

```
Ala Val Ser Arg Leu Phe Tyr Val Ala Ser Arg Glu Gly His Leu Pro
            340                 345                 350

Glu Ile Leu Ser Met Ile His Val Arg Lys His Thr Pro Leu Pro Ala
            355                 360                 365

Val Ile Val Leu His Pro Leu Thr Met Ile Met Leu Phe Ser Gly Asp
        370                 375                 380

Leu Asp Ser Leu Leu Asn Phe Leu Ser Phe Ala Arg Trp Leu Phe Ile
385                 390                 395                 400

Gly Leu Ala Val Ala Gly Leu Ile Tyr Leu Arg Tyr Lys Cys Pro Asp
                405                 410                 415

Met His Arg Pro Phe Lys Val Pro Leu Phe Ile Pro Ala Leu Phe Ser
            420                 425                 430

Phe Thr Cys Leu Phe Met Val Ala Leu Ser Leu Tyr Ser Asp Pro Phe
        435                 440                 445

Ser Thr Gly Ile Gly Phe Val Ile Thr Leu Thr Gly Val Pro Ala Tyr
        450                 455                 460

Tyr Leu Phe Ile Ile Trp Asp Lys Lys Pro Arg Trp Phe Arg Ile Met
465                 470                 475                 480

Ser Glu Lys Ile Thr Arg Thr Leu Gln Ile Ile Leu Glu Val Val Pro
                485                 490                 495

Glu Glu Asp Lys Leu
            500

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Ser Pro Lys Gly Val Leu Gln Asn Thr Gly
1               5                   10

<210> SEQ ID NO 3
<211> LENGTH: 24
<212> TYPE: PRT
<213> ORGANISM: Artificial Sequence
<220> FEATURE:
<223> OTHER INFORMATION: synthetic peptide

<400> SEQUENCE: 3

Arg Pro Ala Ala Thr Ala Val Ile Ser Leu Ala Phe Gly Arg Tyr Ile
1               5                   10                  15

Leu Glu Pro Phe Phe Ile Gln Cys
            20

<210> SEQ ID NO 4
<211> LENGTH: 24
<212> TYPE: PRT
<213> ORGANISM: Artificial Sequence
<220> FEATURE:
<223> OTHER INFORMATION: synthetic peptide

<400> SEQUENCE: 4

Met Gln Leu Ile Lys Gly Gln Thr Gln Asn Phe Lys Asp Ala Phe Ser
1               5                   10                  15

Gly Arg Asp Ser Ser Ile Thr Arg
            20
```

```
<210> SEQ ID NO 5
<211> LENGTH: 31
<212> TYPE: PRT
<213> ORGANISM: Artificial Sequence
<220> FEATURE:
<223> OTHER INFORMATION: synthetic peptide

<400> SEQUENCE: 5

Ala Tyr Phe Thr Thr Ile Asn Ala Glu Glu Leu Leu Leu Ser Asn Ala
1               5                   10                  15

Val Ala Val Thr Phe Ser Glu Arg Leu Leu Gly Asn Phe Ser Leu
            20                  25                  30

<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Tyr Ser Asp Pro Phe Ser
1               5

<210> SEQ ID NO 7
<211> LENGTH: 20
<212> TYPE: PRT
<213> ORGANISM: Artificial Sequence
<220> FEATURE:
<223> OTHER INFORMATION: synthetic peptide

<400> SEQUENCE: 7

Ser Pro Lys Gly Val Leu Gln Asn Thr Gly Ser Val Gly Met Ser Leu
1               5                   10                  15

Thr Ile Trp Thr
            20

<210> SEQ ID NO 8
<211> LENGTH: 14
<212> TYPE: PRT
<213> ORGANISM: Artificial Sequence
<220> FEATURE:
<223> OTHER INFORMATION: synthetic peptide

<400> SEQUENCE: 8

Ile Leu Glu Pro Phe Phe Ile Gln Cys Glu Ile Pro Glu Leu
1               5                   10

<210> SEQ ID NO 9
<211> LENGTH: 22
<212> TYPE: PRT
<213> ORGANISM: Artificial Sequence
<220> FEATURE:
<223> OTHER INFORMATION: synthetic peptide

<400> SEQUENCE: 9

Lys Gly Gln Thr Gln Asn Phe Lys Asp Ala Phe Ser Gly Arg Asp Ser
1               5                   10                  15

Ser Ile Thr Arg Leu Pro
            20

<210> SEQ ID NO 10
<211> LENGTH: 26
<212> TYPE: PRT
<213> ORGANISM: Artificial Sequence
```

```
<220> FEATURE:
<223> OTHER INFORMATION: synthetic peptide

<400> SEQUENCE: 10

Tyr Phe Thr Thr Ile Asn Ala Glu Glu Leu Leu Leu Ser Asn Ala Val
1               5                   10                  15

Ala Val Thr Phe Ser Glu Arg Leu Leu Gly
            20                  25

<210> SEQ ID NO 11
<211> LENGTH: 8
<212> TYPE: PRT
<213> ORGANISM: Artificial Sequence
<220> FEATURE:
<223> OTHER INFORMATION: synthetic peptide

<400> SEQUENCE: 11

Gly Asp Leu Asp Ser Leu Leu Asn
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic peptide

<400> SEQUENCE: 12

Leu Tyr Ser Asp Pro Phe Ser Thr
1               5
```